(12) United States Patent
Altenbach et al.

(10) Patent No.: US 6,503,935 B1
(45) Date of Patent: Jan. 7, 2003

(54) IMIDAZOLES AND RELATED COMPOUNDS AS $\alpha_{1A}$ AGONISTS

(75) Inventors: Robert J. Altenbach, Chicago, IL (US); Michael D. Meyer, Lake Villa, IL (US); James F. Kerwin, Jr., Grayslake, IL (US); Mark W. Holladay, Tucson, AZ (US); Albert Khilevich, Buffalo Grove, IL (US); Teodozyj Kolasa, Lake Villa, IL (US); Jeffrey Rohde, Evanston, IL (US); William A. Carroll, Evanston, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/364,901

(22) Filed: Jul. 29, 1999

Related U.S. Application Data

(63) Continuation-in-part of application No. 09/130,799, filed on Aug. 7, 1998, now abandoned.

(51) Int. Cl.[7] .................... A61K 31/425; A61K 31/415; C07D 277/30; C07D 233/66
(52) U.S. Cl. ................. 514/365; 514/397; 514/400; 548/204; 548/336.5; 548/342.1
(58) Field of Search ............... 548/204, 311.4, 548/338.1, 336.5, 342.1; 514/365, 397, 400

(56) References Cited

U.S. PATENT DOCUMENTS

| | | | |
|---|---|---|---|
| 4,320,148 A | 3/1982 | DeMarinis | 424/230 |
| 4,443,466 A | 4/1984 | Karjalainen et al. | 424/274 |
| 4,507,315 A | 3/1985 | Ashton et al. | 514/396 |
| 4,634,705 A | 1/1987 | DeBernardis et al. | 514/256 |
| 4,764,622 A | 8/1988 | Claussen et al. | 548/159 |
| 4,813,998 A | 3/1989 | Van Lommen et al. | 548/311.4 X |
| 5,043,447 A | 8/1991 | Pascal et al. | 544/370 |
| 5,073,566 A | 12/1991 | Lifer et al. | 514/385 |
| 5,296,609 A | 3/1994 | McCort et al. | 548/325.1 |
| 5,312,936 A | 5/1994 | Lifer et al. | 548/253 |
| 5,378,847 A | 1/1995 | McCort et al. | 544/370 |
| 5,571,925 A | 11/1996 | Lifer et al. | 548/267.6 |
| 5,578,616 A | 11/1996 | Asianian et al. | 514/341 |
| 5,610,174 A | 3/1997 | Craig et al. | 514/401 |
| 5,616,601 A | 4/1997 | Khanna et al. | 514/399 |
| 5,658,938 A | 8/1997 | Geerts et al. | 514/400 |
| 5,756,528 A | 5/1998 | Anthony et al. | 514/399 |
| 5,952,362 A | 9/1999 | Cournoyer et al. | 514/398 |

FOREIGN PATENT DOCUMENTS

| | | |
|---|---|---|
| EP | 0257171 | 3/1988 |
| EP | 0363789 | 4/1990 |
| EP | 0585014 | 3/1994 |
| EP | 0717037 | 6/1996 |
| EP | 0887346 | 12/1998 |
| FR | 2768054 | 3/1999 |
| FR | 2768055 | 3/1999 |
| GB | 2071655 | 9/1981 |
| WO | 9501967 | 1/1995 |
| WO | 9514007 | 5/1995 |
| WO | 9632939 | 10/1996 |
| WO | 9638143 | 12/1996 |
| WO | 9729092 | 8/1997 |
| WO | 9736876 | 10/1997 |
| WO | 9740017 | 10/1997 |
| WO | 9833496 | 8/1998 |
| WO | 9846572 | 10/1998 |
| WO | 9905115 | 2/1999 |
| WO | 00-07997 | 2/2000 |

OTHER PUBLICATIONS

Zhang, X., et al., "Medetomidine Analogs as $\alpha_2$–Adrenergic Ligands. #. Synthesis and Biological Evaluation of a New Series of Medetomidine Analogs and Their Potential Binding Interactions with as $\alpha_2$–Adrenoceptors Involving a "Methyl Pocket"", *J. Med. Chem.*, 40:3014–3024 (1997).
Patent Abstracts of Japan, vol. 1999, No. 5, (May 31, 1999), JP 11 049771 A (Mitsui Chem Inc.), Feb. 23, 1999, abstract.

*Primary Examiner*—Deborah C. Lambkin
(74) *Attorney, Agent, or Firm*—Michael J. Ward

(57) ABSTRACT

Compounds having formula I:

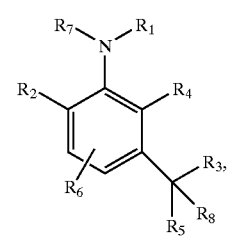

are useful in treating diseases prevented by or ameliorated with $\alpha_{1A}$ agonists. Also disclosed are $\alpha_{1A}$ agonist compositions and a method of activating $\alpha_1$ adrenoceptors in a mammal.

6 Claims, 1 Drawing Sheet

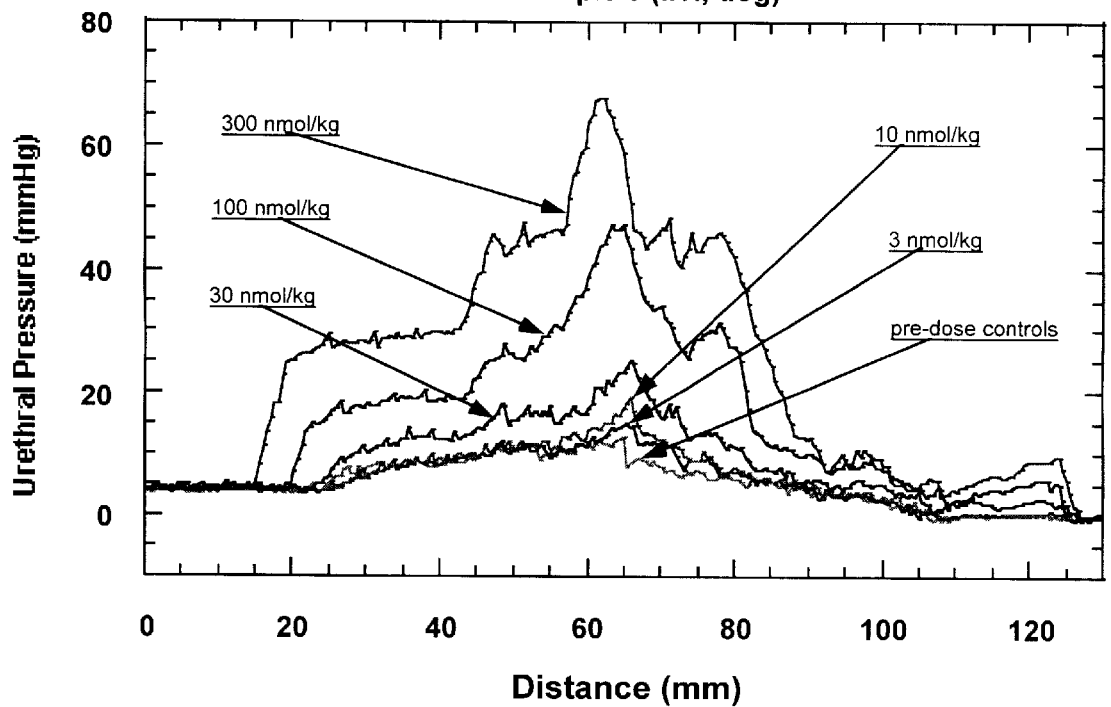
Figure 1: Urethral Pressure Profile (UPP) of Example 8 (i.v., dog)

IMIDAZOLES AND RELATED COMPOUNDS AS $\alpha_{1A}$ AGONISTS

This application is a continuation-in-part of U.S. application Ser. No. 09/130,799, filed Aug. 7, 1998, abandoned, incorporated herein by reference.

TECHNICAL FIELD

This invention relates to compounds which are $\alpha_{1A}$ agonists, pharmaceutical compositions containing these compounds, and methods of treatment using these compounds.

BACKGROUND OF THE INVENTION

The $\alpha_1$ adrenoceptor plays a part in the sympathetic maintenance of smooth muscle tone and $\alpha_1$-adrenergic agonists are known to increase muscle tone in the lower urinary tract (Testa, R. Eur. J. Pharmacol. (1993) 249, 307–315). Phenylpropanolamine (Cummings, J. M. Drugs of Today (1996) 32, 609–614) and midodrine are $\alpha_1$ agonists which have been used for the treatment of urinary incontinence. These agents act by stimulating the $\alpha_1$ receptors present in the urethra and bladder neck (trigone) leading to an increase in intraurethral pressure. However, these agents suffer from cardiovascular related side effects (Taniguchi, N. Eur. J. Pharmacol. (1996) 318, 117–122). Thus an agent that is effective in the treatment of urinary incontinence without cardiovascular side effects is needed.

At least 3 subtypes of the $\alpha_1$ adrenoceptor ($\alpha_{1A}$, $\alpha_{1B}$, and $\alpha_{1D}$) have been identified via pharmacological techniques. The corresponding molecular clones ($\alpha_{1a}$, $\alpha_{1b}$, $\alpha_{1d}$) have been identified (Hancock, A. H. Drug Development Research (1996) 39, 54–107). Studies have shown that the $\alpha_{1A}$ receptor is present in the lower urinary tract (Testa, R. Eur. J. Pharmacol. (1993) 249, 307–315). The $\alpha_{1A}$ subtype has been shown to be the predominant subtype in the urethra (Takahashi, H. Neurourol. Urodyn. (1996), 15, 342–343).

Urinary stress incontinence is the involuntary loss of urine due to a stress such as coughing, sneezing, bending or lifting heavy objects. This condition may occur due to a weakening in the ability of the urethra to constrict. Selective stimulation of the $\alpha_{1A}$ receptor can result in the contraction of the bladder neck (trigone) and urethra leading to an increase in urethral pressure with reduced blood pressure effects. The compounds of the present invention are selective $\alpha_{1A}$ agonists which may preferentially increase intraurethral pressure relative to nonselective $\alpha_1$ agonists such as midodrine and phenylpropanolamine. Therefore, these agents may be useful for the treatment of urinary incontinence.

FR 2768054-A1 and FR 2768055-A1 disclose a series of sulfonamides and sulfonanilides as agents which constrict trigonal smooth muscle and are claimed to be useful for the treatment of ejaculation disorders, especially retrograde ejaculation or aspermia. The compounds of the present invention may be also usefull for the treatment of ejaculatory disorders.

The compounds of the present invention may be useful for the treatment of nasal decongestion (Proctor Pharmac. Ther. B. (1976) 2, 493–509) and septic shock (Cole, L. Blood Purif (1997) 15, 309–318).

EP 0717037 A1 discloses a group of 4-(1,2,3,4-tetrahydro-1-naphthalenyl)-1H-imidazoles that are claimed as $\alpha_2$ agonists and $\alpha_1$ antagonists for the treatment of ischemia and hypertension. Imidazole compounds that are $\alpha_2$-adrenergic ligands are disclosed in (Zhang, et. al. J. Med. Chem (1997) 40, 3014–4024). The compounds of the present invention are structurally and pharmacologically distinct from EP 0717037 A1 and Zhang, et. Al.

WO 99/05115 discloses a group of substituted imidazole derivatives that are claimed as $H_3$ (histamine-3) receptor ligands potentially useful as sedatives, as sleep regulators, as anticonvulsants, as regulators of hypothalamo-hypophyseal secretion, as antidepressants, as modulators of cerebral circulation, in the treatment of asthma, in the treatment of irritable bowel syndrome and as tools in the study of the role of histamine.

EP 0887346 A2 discloses a group of 4-imidazole derivatives of phenyl-alkylsulfonamides as $\alpha_{1A/1L}$ adrenoceptor agonists for the treatment of urinary incontinence and nasal decongestion.

SUMMARY OF THE INVENTION

In its principle embodiment, the present invention discloses compounds having formula I:

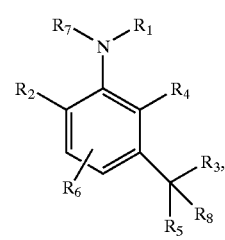

or a pharmaceutically acceptable salt, amide, ester, or prodrug thereof, wherein $R_1$ is selected from the group consisting of —S(O)$_2$R$_9$ and —C(O)R$_{10}$;

$R_9$ is selected from the group consisting of alkenyl, alkyl, alkynyl, aryl, arylalkenyl, arylalkyl, cycloalkyl, cycloalkylalkyl, haloalkyl, heterocycle, and —NZ$_1$Z$_2$ wherein Z$_1$ and Z$_2$ are independently selected from the group consisting of hydrogen, alkyl, alkylcarbonyl, aryl, arylalkyl, and formyl;

$R_{10}$ is selected from the group consisting of alkenyl, alkoxy, alkyl, alkynyl, aryl, arylalkyl, cycloalkyl, cycloalkylalkyl, haloalkyl, and —NZ$_1$Z$_2$;

$R_2$ is selected from the group consisting of hydrogen, alkenyl, alkoxy, alkyl, halo, haloalkyl, and hydroxy;

$R_3$ is selected from the group consisting of hydrogen, alkenyloxy, alkyl, alkoxy, alkoxyalkyl, alkynyloxy, arylalkyl, cycloalkylalkyl, haloalkyl, and hydroxy;

$R_4$ is selected from the group consisting of hydrogen, alkyl, alkoxy, haloalkyl, and hydroxy; or $R_3$ and $R_4$ together with the carbon atoms to which they are attached form a 5-, 6-, or 7-membered carbocyclic ring; or $R_3$ and $R_4$ together with the carbon atoms to which they are attached form a 5- or 6-membered ring containing 1 heteroatom selected from the group consisting of O, NR$_{11}$, and S(O)$_n$;

$R_{11}$ is selected from the group consisting of hydrogen, alkenyl, alkoxycarbonyl, alkyl, alkylcarbonyl, alkynyl, arylalkyl, formyl, —C(O)NZ$_1$Z$_2$, and —SO$_2$NZ$_1$Z$_2$;

n is 0–2;

$R_5$ is selected from the group consisting of imidazol-4-yl, imidazol-5-yl, pyrazole, oxazole, isoxazole, thiazole, isothiazole, oxadiazole, triazole, thiadiazole, pyridine, pyrimidine, pyrazine, and pyridazine optionally substituted with 1 or 2 substituents independently selected from the group consisting of alkenyl, alkoxy, alkoxycarbonyl, alkyl, alkylcarbonyl, alkylcarbonyloxy, alkynyl, arylalkoxycarbonyl, cycloalkyl, cycloalkylalkyl, hydroxy, lower alkoxy, lower alkyl, —NZ$_1$Z$_2$, (NZ$_1$Z$_2$)alkyl, —C(O)NZ$_1$Z$_2$, and —SO$_2$NZ$_1$Z$_2$;

R$_6$ is selected from the group consisting of hydrogen, alkoxy, alkyl, halo, haloalkyl, and hydroxy;

R$_7$ is selected from the group consisting of hydrogen, alkenyl, alkyl, alkynyl, aryl, arylalkyl, cycloalkyl, cycloalkylalkyl, and haloalkyl; and R$_8$ is selected from the group consisting of hydrogen and alkyl; or R$_3$ and R$_8$ together with the carbon atom to which they are attached form a 3-, 4-, 5-, or 6-membered carbocyclic ring; or R$_3$ and R$_8$ together form

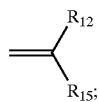

R$_{12}$ and R$_{15}$ are independently selected from the group consisting of hydrogen, alkoxy, alkyl, aryl, arylalkyl, cycloalkyl, and cycloalkylalkyl; or R$_{12}$ and R$_{15}$ together with the carbon atom to which they are attached form a 3-, 4-, 5-, 6-, or 7-membered carbocyclic ring; or R$_{12}$ and R$_4$ together with the carbon atoms to which they are attached form a 5-, 6-, or 7-membered carbocyclic ring;

provided that when R$_{12}$ and R$_4$ together with the carbon atoms to which they are attached form a 5-, 6-, or 7-membered carbocyclic ring then R$_{15}$ is hydrogen; or R$_{12}$ and R$_4$ together with the carbon atoms to which they are attached form a 5- or 6-membered ring containing 1 heteroatom selected from the group consisting of O, NR$_{11}$, and S(O)$_n$;

provided that when R$_{12}$ and R$_4$ together with the carbon atoms to which they are attached form a 5- or 6-membered ring containing 1 heteroatom selected from the group consisting of O, NR$_{11}$, and S(O)$_n$, then R$_{15}$ is hydrogen.

Another embodiment of the present invention relates to pharmaceutical compositions comprising a therapeutically effective amount of a compound of formula I–X or a pharmaceutically acceptable salt, ester, amide, or prodrug thereof in combination with a pharmaceutically acceptable carrier.

Another embodiment of the invention relates to a method of treating ejaculatory dysfunction including, but not limited, to retrograde ejaculation comprising administering a therapeutically effective amount of a compound of formula I–X or a pharmaceutically acceptable salt, ester, amide, or prodrug thereof Yet another embodiment of the invention relates to a method urinary incontinence comprising administering a therapeutically effective amount of a compound of formula I–X or a pharmaceutically acceptable salt, ester, amide, or prodrug thereof.

BRIEF DESCRIPTION OF THE DRAWING

FIG. 1 is a display of the wrethal pressure.

DETAILED DESCRIPTION OF THE INVENTION

All patents, patent applications, and literature references cited in the specification are herein incorporated by reference in their entirety. In the case of inconsistencies, the present disclosure, including definitions, will prevail.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

In its principle embodiment, the present invention discloses compounds having formula I:

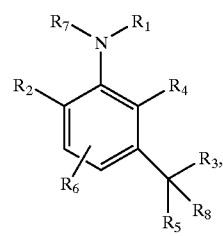

or a pharmaceutically acceptable salt, amide, ester, or prodrug thereof, wherein R$_1$ is selected from the group consisting of —S(O)$_2$R$_9$ and —C(O)R$_{10}$;

R$_9$ is selected from the group consisting of alkenyl, alkyl, alkynyl, aryl, arylalkenyl, arylalkyl, cycloalkyl, cycloalkylalkyl, haloalkyl, heterocycle, and —NZ$_1$Z$_2$ wherein Z$_1$ and Z$_2$ are independently selected from the group consisting of hydrogen, alkyl, alkylcarbonyl, aryl, arylalkyl, and formyl;

R$_{10}$ is selected from the group consisting of alkenyl, alkoxy, alkyl, alkynyl, aryl, arylalkyl, cycloalkyl, cycloalkylalkyl, haloalkyl, and —NZ$_1$Z$_2$;

R$_2$ is selected from the group consisting of hydrogen, alkenyl, alkoxy, alkyl, halo, haloalkyl, and hydroxy;

R$_3$ is selected from the group consisting of hydrogen, alkenyloxy, alkyl, alkoxy, alkoxyalkyl, alkynyloxy, arylalkyl, cycloalkylalkyl, haloalkyl, and hydroxy;

R$_4$ is selected from the group consisting of hydrogen, alkyl, alkoxy, haloalkyl, and hydroxy; or R$_3$ and R$_4$ together with the carbon atoms to which they are attached form a 5-, 6-, or 7-membered carbocyclic ring; or R$_3$ and R$_4$ together with the carbon atoms to which they are attached form a 5- or 6-membered ring containing 1 heteroatom selected from the group consisting of O, NR$_{11}$, and S(O)$_n$;

R$_{11}$ is selected from the group consisting of hydrogen, alkenyl, alkoxycarbonyl, alkyl, alkylcarbonyl, alkynyl, arylalkyl, formyl, —C(O)NZ$_1$Z$_2$, and —SO$_2$NZ$_1$Z$_2$;

n is 0–2;

R$_5$ is selected from the group consisting of imidazol-4-yl, imidazol-5-yl, pyrazole, oxazole, isoxazole, thiazole, isothiazole, oxadiazole, triazole, thiadiazole, pyridine, pyrimidine, pyrazine, and pyridazine optionally substituted with 1 or 2 substituents independently selected from the group consisting of alkenyl, alkoxy, alkoxycarbonyl, alkyl, alkylcarbonyl, alkylcarbonyloxy, alkynyl, arylalkoxycarbonyl, cycloalkyl, cycloalkylalkyl, hydroxy, lower alkoxy, lower alkyl, —$NZ_1Z_2$, $NZ_1Z_2$)alkyl, —$C(O)NZ_1Z_2$, and —$SO_2NZ_1Z_2$;

$R_6$ is selected from the group consisting of hydrogen, alkoxy, alkyl, halo, haloalkyl, and hydroxy;

$R_7$ is selected from the group consisting of hydrogen, alkenyl, alkyl, alkynyl, aryl, arylalkyl, cycloalkyl, cycloalkylalkyl, and haloalkyl; and $R_8$ is selected from the group consisting of hydrogen and alkyl; or $R_3$ and $R_8$ together with the carbon atom to which they are attached form a 3-, 4-, 5-, or 6-membered carbocyclic ring; or $R_3$ and $R_8$ together form

$R_{12}$ and $R_{15}$ are independently selected from the group consisting of hydrogen, alkoxy, alkyl, aryl, arylalkyl, cycloalkyl, and cycloalkylalkyl; or $R_{12}$ and $R_{15}$ together with the carbon atom to which they are attached form a 3-, 4-, 5-, 6-, or 7-membered carbocyclic ring; or $R_{12}$ and $R_4$ together with the carbon atoms to which they are attached form a 5-, 6-, or 7-membered carbocyclic ring;

provided that when $R_{12}$ and $R_4$ together with the carbon atoms to which they are attached form a 5-, 6-, or 7-membered carbocyclic ring then $R_{15}$ is hydrogen; or $R_{12}$ and $R_4$ together with the carbon atoms to which they are attached form a 5- or 6-membered ring containing 1 heteroatom selected from the group consisting of O, $NR_{11}$, and $S(O)_n$;

provided that when $R_{12}$ and $R_4$ together with the carbon atoms to which they are attached form a 5- or 6-membered ring containing 1 heteroatom selected from the group consisting of O, $NR_{11}$, and $S(O)_n$ then $R_{15}$ is hydrogen.

In another embodiment of the present invention, compounds have formula I wherein, $R_1$ is —$S(O)_2R_9$; $R_9$ is selected from lower alkyl, aryl, arylalkenyl, arylalkyl, cycloalkyl, lower haloalkyl, and heterocycle; $R_2$ is selected from hydrogen, lower alkoxy, lower alkyl, halo, lower haloalkyl, and hydroxy; $R_3$ is selected from hydrogen, lower alkyl, lower alkoxy, and hydroxy; $R_4$ is selected from hydrogen and lower alkyl; or $R_3$ and $R_4$ form a 5-, 6-, or 7-membered carbocyclic ring; or $R_3$ and $R_4$ form a 6-membered ring to containing 1 heteroatom which is O; $R_5$ is selected from imidazol-4-yl, imidazol-5-yl, oxazole, and thiazole optionally substituted with 1 or 2 substituents selected from lower alkyl and —$NZ_1Z_2$; $R_6$ is selected from hydrogen, lower alkoxy, lower alkyl, halo, and hydroxy; $R_7$ is selected from hydrogen and lower alkyl; $R_8$ is selected from hydrogen and lower alkyl; or $R_3$ and $R_8$ together form

wherein one of $R_{12}$ and $R_{15}$ is hydrogen and the other is selected from hydrogen, alkoxy, alkyl, aryl, arylalkyl, cycloalkyl, and cycloalkylalkyl; or $R_{12}$ and $R_{15}$ form a 3-, 4-, 5-, 6-, or 7-membered carbocyclic ring; or $R_{12}$ and $R_4$ form a 6-membered carbocyclic ring, provided that when $R_{12}$ and $R_4$ form a 6-membered carbocyclic ring then $R_{15}$ is hydrogen.

In another embodiment of the present invention, compounds have formula I wherein, $R_1$ is —$S(O)_2R_9$; $R_9$ is selected from lower alkyl, aryl, arylalkenyl, arylalkyl, cycloalkyl, lower haloalkyl, and heterocycle wherein aryl is phenyl optionally substituted with 1 or 2 substituents selected from lower alkoxy, lower alkyl, and halo; $R_2$ is selected from hydrogen, lower alkoxy, lower alkyl, halo, lower haloalkyl, and hydroxy; $R_3$ is selected from hydrogen, lower alkyl, lower alkoxy, and hydroxy; $R_4$ is selected from hydrogen and lower alkyl; or $R_3$ and $R_4$ form a 5-, 6-, or 7-membered carbocyclic ring; or $R_3$ and $R_4$ form a 6-membered ring containing 1 heteroatom which is O; $R_5$ is selected from imidazol-4-yl and imidazol-5-yl optionally substituted with 1 or 2 substituents selected from lower alkyl and —$NZ_1Z_2$; $R_6$ is selected from hydrogen, lower alkoxy, lower alkyl, halo, and hydroxy; $R_7$ is selected from hydrogen and lower alkyl; $R_8$ is selected from hydrogen and lower alkyl; or $R_3$ and $R_8$ together form

wherein one of $R_{12}$ and $R_{15}$ is hydrogen and the other is selected from hydrogen, alkoxy, alkyl, aryl, arylalkyl, cycloalkyl, and cycloalkylalkyl; or $R_{12}$ and $R_{15}$ form a 3-, 4-, 5-, 6-, or 7-membered carbocyclic ring; or $R_{12}$ and $R_4$ form a 6-membered carbocyclic ring, provided that when $R_{12}$ and $R_4$ form a 6-membered carbocyclic ring then $R_{15}$ is hydrogen.

In another embodiment of the present invention, compounds have formula I wherein, $R_1$ is —$S(O)_2R_9$; $R_9$ is selected from lower alkyl and lower haloalkyl; $R_2$ is selected from hydrogen, lower alkoxy, lower alkyl, halo, lower haloalkyl, and hydroxy; $R_3$ is selected from hydrogen, lower alkyl, lower alkoxy, and hydroxy; $R_4$ is selected from hydrogen and lower alkyl; or $R_3$ and $R_4$ form a 5-, 6-, or 7-membered carbocyclic ring; or $R_3$ and $R_4$ form a 6-membered ring containing 1 heteroatom which is O; $R_5$ is selected from imidazol-4-yl and imidazol-5-yl optionally substituted with 1 or 2 substituents selected from lower alkyl and —$NZ_1Z_2$; $R_6$ is selected from hydrogen, lower alkoxy, lower alkyl, halo, and hydroxy; $R_7$ is selected from hydrogen and lower alkyl; $R_8$ is selected from hydrogen and lower alkyl; or $R_3$ and $R_8$ together form

wherein one of $R_{12}$ and $R_{15}$ is hydrogen and the other is selected from hydrogen, alkoxy, alkyl, aryl, arylalkyl, cycloalkyl, and cycloalkylalkyl; or $R_{12}$ and $R_{15}$ form a 3-, 4-, 5-, 6-, or 7-membered carbocyclic ring; or $R_{12}$ and $R_4$ form a 6-membered carbocyclic ring, provided that when $R_{12}$ and $R_4$ form a 6-membered carbocyclic ring then $R_{15}$ is hydrogen.

In another embodiment of the present invention, compounds have formula I wherein, $R_3$ and $R_4$ together with the carbon atoms to which they are attached form a 5-membered ring containing 1 heteroatom which is O; and $R_1$, $R_2$, $R_5$, $R_6$, $R_7$, and $R_8$ are as defined in formula I.

In another embodiment of the present invention, compounds have formula I wherein, $R_3$ and $R_4$ together with the carbon atoms to which they are attached form a 5-membered ring containing 1 heteroatom which is $NR_{11}$; and $R_1$, $R_2$, $R_5$, $R_6$, $R_7$, $R_8$ and $R_{11}$ are as defined in formula I.

In another embodiment of the present invention, compounds have formula I wherein, $R_3$ and $R_4$ together with the carbon atoms to which they are attached form a 5-membered ring containing 1 heteroatom which is $S(O)_n$; and $R_1$, $R_2$, $R_5$, $R_6$, $R_7$, $R_8$ and n are as defined in formula I.

In another embodiment of the present invention, compounds have formula I to wherein, $R_3$ and $R_4$ together with the carbon atoms to which they are attached form a 5-membered carbocyclic ring; and $R_1$, $R_2$, $R_5$, $R_6$, $R_7$, and $R_8$ are as defined in formula I.

In another embodiment of the present invention, compounds have formula I wherein, $R_3$ and $R_4$ together with the carbon atoms to which they are attached form a 5-membered carbocyclic ring; $R_5$ is selected from imidazol-4-yl and imidazol-5-yl substituted with 1 substituent selected from alkenyl, alkoxycarbonyl, alkylcarbonyl, alkylcarbonyloxy, alkynyl, arylalkoxycarbonyl, cycloalkyl, cycloalkylalkyl, hydroxy, lower alkoxy, lower alkyl, $-NZ_1Z_2$, $(NZ_1Z_2)$alkyl, $-C(O)NZ_1Z_2$, and $-SO_2NZ_1Z_2$; and $R_1$, $R_2$, $R_6$, $R_7$, and $R_8$ are as defined in formula I.

In another embodiment of the present invention, compounds have formula II:

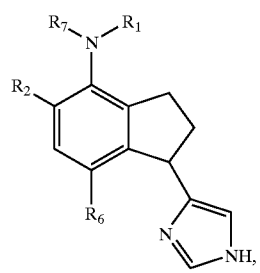

II or a pharmaceutically acceptable salt, ester, amide, or prodrug thereof, wherein $R_1$, $R_2$, $R_6$, and $R_7$ are as defined in formula I.

In another embodiment of the present invention, compounds have formula II wherein, $R_1$ is $-C(O)R_{10}$; $R_7$ is hydrogen; and $R_2$, $R_6$, and $R_7$ are as defined in formula I.

In another embodiment of the present invention, compounds have formula II wherein, $R_1$ is $-S(O)_2R_9$; $R_7$ is hydrogen; and $R_2$, $R_6$, and $R_9$ are as defined in formula I.

In another embodiment of the present invention, compounds have formula II wherein, $R_1$ is $-S(O)_2R_9$; $R_7$ is hydrogen; $R_9$ is selected from loweralkyl and lower haloalkyl; and $R_2$ and $R_6$ are as defined in formula I.

In another embodiment of the present invention, compounds have formula II wherein, $R_1$ is $-S(O)_2R_9$; $R_2$ is hydrogen; $R_6$ is hydrogen; $R_7$ is hydrogen; and $R_9$ is selected from loweralkyl and lower haloalkyl.

In another embodiment of the present invention, compounds have formula II wherein, $R_1$ is $-S(O)_2R_9$; $R_7$ is hydrogen; $R_9$ is selected from ethyl and 2,2,2-trifluoroethyl; and $R_2$ and $R_6$ are as defined in formula I.

In another embodiment of the present invention, compounds have formula II wherein, $R_1$ is $-S(O)_2R_9$; $R_2$ is hydrogen; $R_6$ is hydrogen; $R_7$ is hydrogen; and $R_9$ is selected from ethyl and 2,2,2-trifluoroethyl.

In another embodiment of the present invention, compounds have formula I wherein, $R_3$ and $R_4$ together with the carbon atoms to which they are attached form a 6-membered ring containing 1 heteroatom which is O; and $R_1$, $R_2$, $R_5$, $R_6$, $R_7$, and $R_8$ are as defined in formula I.

In another embodiment of the present invention, compounds have formula I wherein, $R_3$ and $R_4$ together with the carbon atoms to which they are attached form a 6-membered ring containing 1 heteroatom which is $NR_{11}$; and $R_1$, $R_2$, $R_5$, $R_6$, $R_7$, $R_8$ and $R_{11}$ are as defined in formula I.

In another embodiment of the present invention, compounds have formula I wherein, $R_3$ and $R_4$ together with the carbon atoms to which they are attached form a 6-membered ring containing 1 heteroatom which is $S(O)_n$; and $R_1$, $R_2$, $R_5$, $R_6$, $R_7$, $R_8$ and n are as defined in formula I.

In another embodiment of the present invention, compounds have formula I wherein, $R_3$ and $R_4$ together with the carbon atoms to which they are attached form a 6-membered carbocyclic ring; and $R_1$, $R_2$, $R_5$, $R_6$, $R_7$, and $R_8$ are as defined in formula I.

In another embodiment of the present invention, compounds have formula I wherein, $R_3$ and $R_4$ together with the carbon atoms to which they are attached form a 6-membered ring containing 1 heteroatom which is O; $R_5$ is selected from imidazol-4-yl and imidazol-5-yl optionally substituted with 1 substituent selected from alkenyl, alkoxycarbonyl, alkylcarbonyl, alkylcarbonyloxy, alkynyl, arylalkoxycarbonyl, cycloalkyl, cycloalkylalkyl, hydroxy, lower alkoxy, lower alkyl, $-NZ_1Z_2$, $(NZ_1Z_2)$alkyl, $-C(O)NZ_1Z_2$, and $-SO_2NZ_1Z_2$; and $R_1$, $R_2$, $R_6$, $R_7$, and $R_8$ are as defined in formula I.

In another embodiment of the present invention, compounds have formula I wherein, $R_3$ and $R_4$ together with the carbon atoms to which they are attached form a 6-membered carbocyclic ring; $R_5$ is selected from imidazol-4-yl and imidazol-5-yl optionally substituted with 1 substituent selected from alkenyl, alkoxycarbonyl, alkylcarbonyl, alkylcarbonyloxy, alkynyl, arylalkoxycarbonyl, cycloalkyl, cycloalkylalkyl, hydroxy, lower alkoxy, lower alkyl, $-NZ_1Z_2$, $(NZ_1Z_2)$alkyl, $-C(O)NZ_1Z_2$, and $-SO_2NZ_1Z_2$; and $R_1$, $R_2$, $R_6$, $R_7$, and $R_8$ are as defined in formula I.

In another embodiment of the present invention, compounds have formula III:

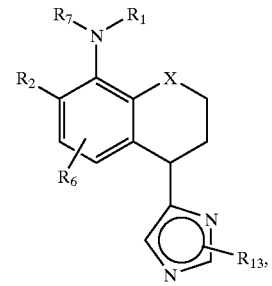

III or a pharmaceutically acceptable salt, ester, amide, or prodrug thereof, wherein X is selected from $CH_2$, O, $S(O)_n$, and $NR_{11}$; $R_{13}$ is selected from hydrogen and lower alkyl; and $R_1$, $R_2$, $R_6$, $R_7$, $R_{11}$, and n are as defined in formula I.

In another embodiment of the present invention, compounds have formula III wherein, X is $CH_2$; $R_1$ is —C(O)$R_{10}$; $R_7$ is hydrogen; $R_2$, $R_6$, and $R_{10}$ are as defined in formula I; and $R_{13}$ is as defined in formula III.

In another embodiment of the present invention, compounds have formula III wherein, X is $CH_2$; $R_1$ is —C(O)$R_{10}$; $R_7$ is hydrogen; $R_{10}$ is selected from lower alkyl and lower haloalkyl; $R_2$ and $R_6$ are as defined in formula I; and $R_{13}$ is as defined in formula III.

In another embodiment of the present invention, compounds have formula III wherein, X is $CH_2$; $R_1$ is —C(O)$R_{10}$; $R_2$ is hydrogen; $R_6$ is hydrogen; $R_7$ is hydrogen; $R_{10}$ is selected from lower alkyl and lower haloalkyl; and $R_{13}$ is hydrogen.

In another embodiment of the present invention, compounds have formula III wherein, X is $CH_2$; $R_1$ is —S(O)$_2R_9$; $R_7$ is selected from hydrogen and lower alkyl; $R_2$, $R_6$, and $R_9$ are as defined in formula I; and $R_{13}$ is as defined in formula III.

In another embodiment of the present invention, compounds have formula III wherein, X is $CH_2$; $R_1$ is —S(O)$_2R_9$; $R_7$ is selected from hydrogen and lower alkyl; $R_9$ is selected from lower alkyl, lower haloalkyl, and cycloalkyl; $R_2$ and $R_6$ are as defined in formula I; and $R_{13}$ is as defined in formula III.

In another embodiment of the present invention, compounds have formula III wherein, X is $CH_2$; $R_1$ is —S(O)$_2R_9$; $R_2$ is selected from hydrogen, lower alkoxy, and hydroxy; $R_6$ is selected from hydrogen, lower alkoxy, lower alkyl, halo and hydroxy; $R_7$ is selected from hydrogen and lower alkyl; $R_9$ is selected from lower alkyl, lower haloalkyl, and cycloalkyl; and $R_{13}$ is as defined in formula III.

In another embodiment of the present invention, compounds have formula III wherein, X is $CH_2$; $R_1$ is —S(O)$_2R_9$; $R_7$ is selected from hydrogen and lower alkyl; $R_9$ is selected from aryl, arylalkenyl, arylalkyl, and heterocycle; $R_2$ and $R_6$ are as defined in formula I; and $R_{13}$ is as defined in formula III.

In another embodiment of the present invention, compounds have formula III wherein, X is $CH_2$; $R_1$ is —S(O)$_2R_9$; $R_7$ is selected from hydrogen and lower alkyl; $R_9$ is selected from aryl, arylalkenyl, arylalkyl, and heterocycle, wherein aryl is phenyl optionally substituted with 1 substituent selected from lower alkoxy and lower alkyl, and wherein heterocycle is selected from benzothiophene, imidazole, isoxazole, quinoline, pyrazole, thiazole, and thiophene optionally substituted with 1, 2, or 3 substituents selected from alkoxycarbonyl, lower alkyl, halo, and $NZ_1Z_2$; $R_2$ and $R_6$ are as defined in formula I; and $R_{13}$ is as defined in formula III.

In another embodiment of the present invention, compounds have formula III wherein, X is $CH_2$; $R_1$ is —S(O)$_2R_9$; $R_2$ is hydrogen; $R_6$ is hydrogen; $R_7$ is hydrogen; $R_9$ is selected from aryl, arylalkenyl, arylalkyl, and heterocycle, wherein aryl is phenyl optionally substituted with 1 substituent selected from lower alkoxy and lower alkyl, and wherein heterocycle is selected from benzothiophene, imidazole, isoxazole, quinoline, pyrazole, thiazole, and thiophene optionally substituted with 1, 2, or 3 substituents selected from alkoxycarbonyl, lower alkyl, halo, and $NZ_1Z_2$; and $R_{13}$ is hydrogen.

In another embodiment of the present invention, compounds have formula III wherein, X is $CH_2$; $R_1$ is —S(O)$_2R_9$; $R_7$ is selected from hydrogen and lower alkyl; $R_9$ is selected from ethyl and 2,2,2-trifluoroethyl; and $R_2$ and $R_6$ are as defined in formula I; and $R_{13}$ is as defined in formula III.

In another embodiment of the present invention, compounds have formula III wherein, X is $CH_2$; $R_1$ is —S(O)$_2R_9$; $R_2$ is hydrogen; $R_6$ is selected from hydrogen, halo, and lower alkoxy; $R_7$ is hydrogen; $R_9$ is selected from ethyl and 2,2,2-trifluoroethyl; and $R_{13}$ is hydrogen.

In another embodiment of the present invention, compounds have formula III wherein, X is O; $R_1$ is —C(O)$R_{10}$; $R_7$ is hydrogen; and $R_2$, $R_6$, and $R_{10}$ are as defined in formula I; and $R_{13}$ is as defined in formula III.

In another embodiment of the present invention, compounds have formula III wherein, X is O; $R_1$ is —S(O)$_2R_9$; $R_7$ is hydrogen; and $R_2$, $R_6$, and $R_9$ are as defined in formula I; and $R_{13}$ is as defined in formula III.

In another embodiment of the present invention, compounds have formula III wherein, X is O; $R_1$ is —S(O)$_2R_9$; $R_7$ is hydrogen; $R_9$ is selected from lower alkyl and lower haloalkyl; and $R_2$ and $R_6$ are as defined in formula I; and $R_{13}$ is as defined in formula III.

In another embodiment of the present invention, compounds have formula III wherein, X is O; $R_1$ is —S(O)$_2R_9$; $R_2$ is hydrogen; $R_6$ is selected from hydrogen and halo; $R_7$ is hydrogen; $R_9$ is selected from lower alkyl and lower haloalkyl; and $R_{13}$ is hydrogen.

In another embodiment of the present invention, compounds have formula III wherein, X is O; $R_1$ is —S(O)$_2R_9$; $R_7$ is hydrogen; $R_9$ is selected from ethyl and 2,2,2-trifluoroethyl; and $R_2$ and $R_6$ are as defined in formula I; and $R_{13}$ is as defined in formula III.

In another embodiment of the present invention, compounds have formula III wherein, X is O; $R_1$ is —S(O)$_2R_9$; $R_2$ is hydrogen; $R_6$ is hydrogen; $R_7$ is hydrogen; $R_9$ is selected from ethyl and 2,2,2-trifluoroethyl; and $R_{13}$ is hydrogen.

In another embodiment of the present invention, compounds have formula I wherein, $R_3$ and $R_4$ together with the carbon atoms to which they are attached form a 7-membered carbocyclic ring; and $R_1$, $R_2$, $R_5$, $R_6$, $R_7$, and $R_8$ are as defined in formula I.

In another embodiment of the present invention, compounds have formula I wherein, $R_3$ and $R_4$ together with the carbon atoms to which they are attached form a 7-membered carbocyclic ring; $R_5$ is selected from imidazol-4-yl and imidazol-5-yl optionally substituted with 1 substituent selected from alkenyl, alkoxycarbonyl, alkylcarbonyl, alkylcarbonyloxy, alkynyl, arylalkoxycarbonyl, cycloalkyl, cycloalkylalkyl, hydroxy, lower alkoxy, lower alkyl, —$NZ_1Z_2$, ($NZ_1Z_2$)alkyl, —C(O)$NZ_1Z_2$, and —$SO_2NZ_1Z_2$; and $R_1$, $R_2$, $R_6$, $R_7$, and $R_8$ are as defined in formula I.

In another embodiment of the present invention, compounds have formula IV:

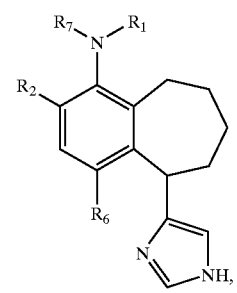

IV or a pharmaceutically acceptable salt, ester, amide, or prodrug thereof, wherein $R_1$, $R_2$, $R_6$, and $R_7$ are as defined in formula I.

In another embodiment of the present invention, compounds have formula IV wherein, $R_1$ is —C(O)$R_{10}$; $R_7$ is hydrogen; and $R_2$, $R_6$, and $R_{10}$ are as defined in formula I.

In another embodiment of the present invention, compounds have formula IV wherein, $R_1$ is —$S(O)_2R_9$; $R_7$ is hydrogen; and $R_2$, $R_6$, and $R_9$ are as defined in formula I.

In another embodiment of the present invention, compounds have formula IV wherein, $R_1$ is —$S(O)_2R_9$; $R_7$ is hydrogen; $R_9$ is selected from loweralkyl and haloalkyl; and $R_2$ and $R_6$ are as defined in formula I.

In another embodiment of the present invention, compounds have formula IV wherein, $R_1$ is —$S(O)_2R_9$; $R_2$ is hydrogen; $R_6$ is hydrogen; $R_7$ is hydrogen; and $R_9$ is selected from loweralkyl and haloalkyl.

In another embodiment of the present invention, compounds have formula IV wherein, $R_1$ is —$S(O)_2R_9$; $R_7$ is hydrogen; $R_9$ is selected from ethyl and 2,2,2-trifluoroethyl; and $R_2$ and $R_6$ are as defined in formula I.

In another embodiment of the present invention, compounds have formula IV wherein, $R_1$ is —$S(O)_2R_9$; $R_2$ is hydrogen; $R_6$ is hydrogen; $R_7$ is hydrogen; and $R_9$ is selected from ethyl and 2,2,2-trifluoroethyl.

In another embodiment of the present invention, compounds have formula V:

$$V$$

or a pharmaceutically acceptable salt, amide, ester, or prodrug thereof, wherein $R_1$, $R_2$, $R_3$, $R_4$, $R_6$, and $R_7$ are as defined in formula I.

In another embodiment of the present invention, compounds have formula V wherein, $R_1$ is —$C(O)R_{10}$; $R_7$ is hydrogen; and $R_2$, $R_3$, $R_4$, $R_6$, and $R_{10}$ are as defined in formula I.

In another embodiment of the present invention, compounds have formula V wherein, $R_1$ is —$C(O)R_{10}$; $R_7$ is hydrogen; $R_{10}$ is selected from lower alkyl and lower haloalkyl; and $R_2$, $R_3$, $R_4$, and $R_6$ are as defined in formula I.

In another embodiment of the present invention, compounds have formula V wherein, $R_1$ is —$C(O)R_{10}$; $R_7$ is hydrogen; $R_2$ is selected from hydrogen and hydroxy; $R_3$ is selected from hydrogen and lower alkyl; $R_4$ is selected from hydrogen and lower alkyl; $R_6$ is is selected from hydrogen, lower alkyl, and halo; and $R_{10}$ is selected from lower alkyl and lower haloalkyl.

In another embodiment of the present invention, compounds have formula V wherein, $R_1$ is —$S(O)_2R_9$; $R_7$ is hydrogen; and $R_2$, $R_3$, $R_4$, $R_6$, and $R_9$ are as defined in formula I.

In another embodiment of the present invention, compounds have formula V wherein, $R_1$ is —$S(O)_2R_9$; $R_7$ is hydrogen; $R_9$ is lower alkyl; and $R_2$, $R_3$, $R_4$, and $R_6$ are as defined in formula I.

In another embodiment of the present invention, compounds have formula V wherein, $R_1$ is —$S(O)_2R_9$; $R_7$ is hydrogen; $R_9$ is methyl; and $R_2$, $R_3$, $R_4$, and $R_6$ are as defined in formula I.

In another embodiment of the present invention, compounds have formula V wherein, $R_1$ is —$S(O)_2R_9$; $R_2$ is hydroxy; $R_3$ is hydrogen; $R_4$ is hydrogen; $R_6$ is hydrogen; $R_7$ is hydrogen; and $R_9$ is methyl.

In another embodiment of the present invention, compounds have formula V wherein, $R_1$ is —$S(O)_2R_9$; $R_2$ is hydrogen; $R_3$ is methyl; $R_4$ is hydrogen; $R_6$ is hydrogen; $R_7$ is hydrogen; and $R_9$ is methyl.

In another embodiment of the present invention, compounds have formula V wherein, $R_1$ is —$S(O)_2R_9$; $R_2$ is hydrogen; $R_3$ is hydrogen; $R_4$ is hydrogen; $R_6$ is fluorine; $R_7$ is hydrogen; and $R_9$ is methyl.

In another embodiment of the present invention, compounds have formula V wherein, $R_1$ is —$S(O)_2R_9$; $R_7$ is hydrogen; $R_9$ is ethyl; and $R_2$, $R_3$, $R_4$, and $R_6$ are as defined in formula I.

In another embodiment of the present invention, compounds have formula V wherein, $R_1$ is —$S(O)_2R_9$; $R_2$ is hydrogen; $R_3$ is lower alkyl; $R_4$ is hydrogen; $R_6$ is hydrogen; $R_7$ is hydrogen; and $R_9$ is ethyl.

In another embodiment of the present invention, compounds have formula V wherein, $R_1$ is —$S(O)_2R_9$; $R_2$ is hydrogen; $R_3$ is methyl; $R_4$ is hydrogen; $R_6$ is hydrogen; $R_7$ is hydrogen; and $R_9$ is ethyl.

In another embodiment of the present invention, compounds have formula V wherein, $R_1$ is —$S(O)_2R_9$; $R_2$ is hydrogen; $R_3$ is hydrogen; $R_4$ is lower alkyl; $R_6$ is hydrogen; $R_7$ is hydrogen; and $R_9$ is ethyl.

In another embodiment of the present invention, compounds have formula V wherein, $R_1$ is —$S(O)_2R_9$; $R_2$ is hydrogen; $R_3$ is hydrogen; $R_4$ is methyl; $R_6$ is hydrogen; $R_7$ is hydrogen; and $R_9$ is ethyl.

In another embodiment of the present invention, compounds have formula V wherein, $R_1$ is —$S(O)_2R_9$; $R_2$ is hydrogen; $R_3$ is hydrogen; $R_4$ is hydrogen; $R_6$ is hydrogen; $R_7$ is hydrogen; and $R_9$ is ethyl.

In another embodiment of the present invention, compounds have formula V wherein, $R_1$ is —$S(O)_2R_9$; $R_7$ is hydrogen; $R_9$ is lower haloalkyl; and $R_2$, $R_3$, $R_4$, and $R_6$ are as defined in formula I.

In another embodiment of the present invention, compounds have formula V wherein, $R_1$ is —$S(O)_2R_9$; $R_2$ is hydrogen; $R_3$ is lower alkyl; $R_4$ is hydrogen; $R_6$ is hydrogen; $R_7$ is hydrogen; and $R_9$ is lower haloalkyl.

In another embodiment of the present invention, compounds have formula V wherein, $R_1$ is —$S(O)_2R_9$; $R_2$ is hydrogen; $R_3$ is hydrogen; $R_4$ is lower alkyl; $R_6$ is hydrogen; $R_7$ is hydrogen; and $R_9$ is lower haloalkyl.

In another embodiment of the present invention, compounds have formula V wherein, $R_1$ is —$S(O)_2R_9$; $R_2$ is hydrogen; $R_3$ is hydrogen; $R_4$ is hydrogen; $R_6$ is hydrogen; $R_7$ is hydrogen; and $R_9$ is lower haloalkyl.

In another embodiment of the present invention, compounds have formula V wherein, $R_1$ is —$S(O)_2R_9$; $R_7$ is hydrogen; $R_9$ is 2,2,2-trifluoroethyl; and $R_2$, $R_3$, $R_4$, and $R_6$ are as defined in formula I.

In another embodiment of the present invention, compounds have formula V wherein, $R_1$ is —$S(O)_2R_9$; $R_2$ is hydrogen; $R_3$ is lower alkyl; $R_4$ is hydrogen; $R_6$ is hydrogen; $R_7$ is hydrogen; and $R_9$ is 2,2,2-trifluoroethyl.

In another embodiment of the present invention, compounds have formula V wherein, $R_1$ is —$S(O)_2R_9$; $R_2$ is hydrogen; $R_3$ is hydrogen; $R_4$ is lower alkyl; $R_6$ is hydrogen; $R_7$ is hydrogen; and $R_9$ is 2,2,2-trifluoroethyl.

In another embodiment of the present invention, compounds have formula V wherein, $R_1$ is —$S(O)_2R_9$; $R_2$ is hydrogen; $R_3$ is hydrogen; $R_4$ is hydrogen; $R_6$ is hydrogen; $R_7$ is hydrogen; and $R_9$ is 2,2,2-trifluoroethyl.

In another embodiment of the present invention, compounds have formula VI:

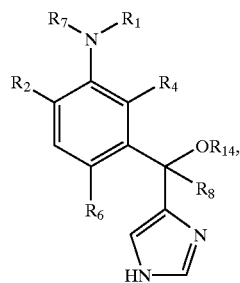

VI or a pharmaceutically acceptable salt, amide, ester, or prodrug thereof, wherein $R_1$, $R_2$, $R_4$, $R_6$, $R_7$, and $R_8$ are as defined in formula I; and $R_{14}$ is selected from hydrogen, alkenyl, alkyl, and alkynyl.

In another embodiment of the present invention, compounds have formula VI wherein, $R_1$ is —C(O)$R_{10}$; $R_7$ is hydrogen; and $R_2$, $R_4$, $R_6$, $R_8$, and $R_{10}$ are as defined in formula I; and $R_{14}$ is as defined in formula VI.

In another embodiment of the present invention, compounds have formula VI wherein, $R_1$ is —C(O)$R_{10}$; $R_7$ is hydrogen; $R_{10}$ is selected from lower alkyl and lower haloalkyl; and $R_2$, $R_4$, $R_6$, and $R_8$ are as defined in formula I; and $R_{14}$ is as defined in formula VI.

In another embodiment of the present invention, compounds have formula VI wherein, $R_1$ is —C(O)$R_{10}$; $R_2$ is hydrogen; $R_4$ is hydrogen; $R_6$ is hydrogen; $R_7$ is hydrogen; $R_{10}$ is selected from lower alkyl and lower haloalkyl; $R_8$ is as defined in formula I; and $R_{14}$ is as defined in formula VI.

In another embodiment of the present invention, compounds have formula VI wherein, $R_1$ is —S(O)$_2R_9$; $R_7$ is hydrogen; and $R_2$, $R_4$, $R_6$, $R_8$, and $R_9$ are as defined in formula I; and $R_{14}$ is as defined in formula VI.

In another embodiment of the present invention, compounds have formula VI wherein, $R_1$ is —S(O)$_2R_9$; $R_7$ is hydrogen; $R_9$ is selected from lower alkyl and lower haloalkyl; and $R_2$, $R_4$, $R_6$, and $R_8$ are as defined in formula I; and $R_{14}$ is as defined in formula VI.

In another embodiment of the present invention, compounds have formula VI wherein, $R_1$ is —S(O)$_2R_9$; $R_2$ is hydrogen; $R_4$ is hydrogen; $R_6$ is hydrogen; $R_7$ is hydrogen; $R_9$ is selected from lower alkyl and lower haloalkyl; $R_8$ is as defined in formula I; and $R_{14}$ is as defined in formula VI.

In another embodiment of the present invention, compounds have formula VI wherein, $R_1$ is —S(O)$_2R_9$; $R_7$ is hydrogen; $R_9$ is ethyl; and $R_2$, $R_4$, $R_6$, and $R_8$ are as defined in formula I; and $R_{14}$ is as defined in formula VI.

In another embodiment of the present invention, compounds have formula VI wherein, $R_1$ is —S(O)$_2R_9$; $R_2$ is hydrogen; $R_4$ is hydrogen; $R_6$ is hydrogen; $R_7$ is hydrogen; $R_9$ is ethyl; $R_8$ is as defined in formula I; and $R_{14}$ is as defined in formula VI.

In another embodiment of the present invention, compounds have formula VI wherein, $R_1$ is —S(O)$_2R_9$; $R_2$ is hydrogen; $R_4$ is hydrogen; $R_6$ is hydrogen; $R_7$ is hydrogen; $R_8$ is lower alkyl; $R_9$ is ethyl; and $R_{14}$ is hydrogen.

In another embodiment of the present invention, compounds have formula VI wherein, $R_1$ is —S(O)$_2R_9$; $R_7$ is hydrogen; $R_9$ is 2,2,2-trifluoroethyl; and $R_2$, $R_4$, $R_6$, and $R_8$ are as defined in formula I; and $R_{14}$ is as defined in formula VI.

In another embodiment of the present invention, compounds have formula VI wherein, $R_1$ is —S(O)$_2R_9$; $R_2$ is hydrogen; $R_4$ is hydrogen; $R_6$ is hydrogen; $R_7$ is hydrogen; $R_9$ is 2,2,2-trifluoroethyl; $R_8$ is as defined in formula I; and $R_{14}$ is as defined in formula VI.

In another embodiment of the present invention, compounds have formula VII:

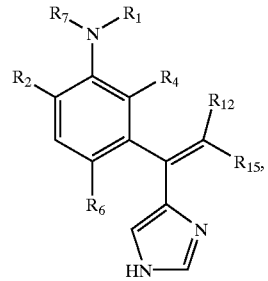

VII or a pharmaceutically acceptable salt, amide, ester, or prodrug thereof, wherein $R_1$, $R_2$, $R_4$, $R_6$, and $R_7$ are as defined in formula I; and $R_{12}$ and $R_{15}$ are independently selected from hydrogen, alkoxy, alkyl, aryl, arylalkyl, cycloalkyl, and cycloalkylalkyl; or $R_{12}$ and $R_{15}$ together with the carbon atom to which they are attached form a 3-, 4-, 5-, 6-, or 7-membered carbocyclic ring.

In another embodiment of the present invention, compounds have formula VII wherein, $R_1$ is —C(O)$R_{10}$; $R_7$ is hydrogen; and $R_2$, $R_4$, $R_6$, and $R_{10}$ are as defined in formula I; and $R_{12}$ and $R_{15}$ are as defined in formula VII.

In another embodiment of the present invention, compounds have formula VII wherein, $R_1$ is —C(O)$R_{10}$; $R_7$ is hydrogen; $R_{10}$ is selected from lower alkyl and lower haloalkyl; and $R_2$, $R_4$, and $R_6$ are as defined in formula I; and $R_{12}$ and $R_{15}$ are as defined in formula VII.

In another embodiment of the present invention, compounds have formula VII wherein, $R_1$ is —C(O)$R_{10}$; $R_2$ is hydrogen; $R_4$ is hydrogen; $R_6$ is hydrogen; $R_7$ is hydrogen; $R_{10}$ is selected from lower alkyl and lower haloalkyl; and one of $R_{12}$ and $R_{15}$ is hydrogen, and the other is selected from hydrogen, lower alkoxy, alkyl, and cycloalkyl; or $R_{12}$ and $R_{15}$ together with the carbon atom to which they are attached form a 3-, 4-, 5-, 6-, or 7-membered carbocyclic ring.

In another embodiment of the present invention, compounds have formula VII wherein, $R_1$ is —S(O)$_2R_9$; $R_7$ is hydrogen; and $R_2$, $R_4$, $R_6$, and $R_9$ are as defined in formula I; and $R_{12}$ and $R_{15}$ are as defined in formula VII.

In another embodiment of the present invention, compounds have formula VII wherein, $R_1$ is —S(O)$_2R_9$; $R_7$ is hydrogen; $R_9$ is selected from lower alkyl and lower haloalkyl; and $R_2$, $R_4$, and $R_6$ are as defined in formula I; and $R_{12}$ and $R_{15}$ are as defined in formula VII.

In another embodiment of the present invention, compounds have formula VII wherein, $R_1$ is —S(O)$_2R_9$; $R_2$ is hydrogen; $R_4$ is hydrogen; $R_6$ is hydrogen; $R_7$ is hydrogen; $R_9$ is selected from lower alkyl and lower haloalkyl; and one of $R_{12}$ and $R_{15}$ is hydrogen, and the other is selected from hydrogen, lower alkoxy, alkyl, and cycloalkyl; or $R_{12}$ and $R_{15}$ together with the carbon atom to which they are attached form a 3-, 4-, 5-, 6-, or 7-membered carbocyclic ring.

In another embodiment of the present invention, compounds have formula VII wherein, $R_1$ is —S(O)$_2R_9$; $R_7$ is hydrogen; $R_9$ is ethyl; and $R_2$, $R_4$, and $R_6$ are as defined in formula I; and $R_{12}$, and $R_{15}$ are as defined in formula VII.

In another embodiment of the present invention, compounds have formula VII wherein, $R_1$ is —S(O)$_2R_9$; $R_2$ is hydrogen; $R_4$ is hydrogen; $R_6$ is hydrogen; $R_7$ is hydrogen;

$R_9$ is ethyl; and one of $R_{12}$ and $R_{15}$ is hydrogen, and the other is selected from hydrogen, lower alkoxy, alkyl, and cycloalkyl; or $R_{12}$ and $R_{15}$ together with the carbon atom to which they are attached form a 3-, 4-, 5-, 6-, or 7-membered carbocyclic ring.

In another embodiment of the present invention, compounds have formula VII wherein, $R_1$ is —$S(O)_2R_9$; $R_2$ is hydrogen; $R_4$ is hydrogen; $R_6$ is hydrogen; $R_7$ is hydrogen; $R_9$ is ethyl; $R_{12}$ is hydrogen; and $R_{15}$ is hydrogen.

In another embodiment of the present invention, compounds have formula VII wherein, $R_1$ is —$S(O)_2R_9$; $R_2$ is hydrogen; $R_4$ is hydrogen; $R_6$ is hydrogen; $R_7$ is hydrogen; $R_9$ is ethyl; and one of $R_{12}$ and $R_{15}$ is hydrogen and the other is lower alkoxy.

In another embodiment of the present invention, compounds have formula VII wherein, $R_1$ is —$S(O)_2R_9$; $R_2$ is hydrogen; $R_4$ is hydrogen; $R_6$ is hydrogen; $R_7$ is hydrogen; $R_9$ is ethyl; and $R_{12}$ and $R_{15}$ together with the carbon atom to which they are attached form a 3-, 4-, 5-, 6-, or 7-membered carbocyclic ring.

In another embodiment of the present invention, compounds have formula VII wherein, $R_1$ is —$S(O)_2R_9$; $R_7$ is hydrogen; $R_9$ is 2,2,2-trifluoroethyl; and $R_2$, $R_4$, and $R_6$ are as defined in formula I; and $R_{12}$, and $R_{15}$ are as defined in formula VII.

In another embodiment of the present invention, compounds have formula VII wherein, $R_1$ is —$S(O)_2R_9$; $R_2$ is hydrogen; $R_4$ is hydrogen; $R_6$ is hydrogen; $R_7$ is hydrogen; $R_9$ is 2,2,2-trifluoroethyl; and one of $R_{12}$ and $R_{15}$ is hydrogen, and the other is selected from hydrogen, lower alkoxy, alkyl, and cycloalkyl; or $R_{12}$ and $R_{15}$ together with the carbon atom to which they are attached form a 3-, 4-, 5-, 6-, or 7-membered carbocyclic ring.

In another embodiment of the present invention, compounds have formula VIII:

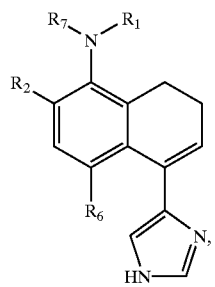

VIII or a pharmaceutically acceptable salt, amide, ester, or prodrug thereof, wherein $R_1$, $R_2$, $R_6$, and $R_7$ are as defined in formula I.

In another embodiment of the present invention, compounds have formula VIII wherein, $R_1$ is —$C(O)R_{10}$; $R_7$ is hydrogen; and $R_2$, $R_6$, and $R_{10}$ are as defined in formula I.

In another embodiment of the present invention, compounds have formula VIII wherein, $R_1$ is —$C(O)R_{10}$; $R_7$ is hydrogen; $R_{10}$ is selected from lower alkyl and lower haloalkyl; and $R_2$ and $R_6$ are as defined in formula I.

In another embodiment of the present invention, compounds have formula VIII wherein, $R_1$ is —$C(O)R_{10}$; $R_2$ is hydrogen; $R_6$ is hydrogen; $R_7$ is hydrogen; and $R_{10}$ is selected from lower alkyl and lower haloalkyl.

In another embodiment of the present invention, compounds have formula VIII wherein, $R_1$ is —$S(O)_2R_9$; $R_7$ is hydrogen; and $R_2$, $R_6$, and $R_9$ are as defined in formula I.

In another embodiment of the present invention, compounds have formula VIII wherein, $R_1$ is —$S(O)_2R_9$; $R_7$ is hydrogen; $R_9$ is selected from lower alkyl and lower haloalkyl; and $R_2$ and $R_6$ are as defined in formula I.

In another embodiment of the present invention, compounds have formula VIII wherein, $R_1$ is —$S(O)_2R_9$; $R_2$ is hydrogen; $R_6$ is hydrogen; $R_7$ is hydrogen; and $R_9$ is selected from lower alkyl and lower haloalkyl.

In another embodiment of the present invention, compounds have formula VIII wherein, $R_1$ is —$S(O)_2R_9$; $R_7$ is hydrogen; $R_9$ is ethyl; and $R_2$ and $R_6$ are as defined in formula I.

In another embodiment of the present invention, compounds have formula VIII wherein, $R_1$ is —$S(O)_2R_9$; $R_2$ is hydrogen; $R_6$ is hydrogen; $R_7$ is hydrogen; and $R_9$ is ethyl.

In another embodiment of the present invention, compounds have formula VIII wherein, $R_1$ is —$S(O)_2R_9$; $R_7$ is hydrogen; $R_9$ is 2,2,2-trifluoroethyl; and $R_2$ and $R_6$ are as defined in formula I.

In another embodiment of the present invention, compounds have formula VIII wherein, $R_1$ is —$S(O)_2R_9$; $R_2$ is hydrogen; $R_6$ is hydrogen; $R_7$ is hydrogen; and $R_9$ is 2,2,2-trifluoroethyl.

In another embodiment of the present invention, compounds have formula IX:

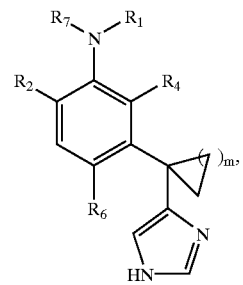

IX or a pharmaceutically acceptable salt, amide, ester, or prodrug thereof, wherein $R_1$, $R_2$, $R_6$, and $R_7$ are as defined in formula I; and m is 1–4.

In another embodiment of the present invention, compounds have formula IX wherein, $R_1$ is —$C(O)R_{10}$; $R_7$ is hydrogen; and $R_2$, $R_4$, $R_6$, and $R_{10}$ are as defined in formula I; and m is as defined in formula IX.

In another embodiment of the present invention, compounds have formula IX wherein, $R_1$ is —$C(O)R_{10}$; $R_7$ is hydrogen; $R_{10}$ is selected from lower alkyl and lower haloalkyl; and $R_2$, $R_4$, and $R_6$ are as defined in formula I; and m is as defined in formula IX.

In another embodiment of the present invention, compounds have formula IX wherein, $R_1$ is —$C(O)R_{10}$; $R_2$ is hydrogen; $R_4$ is hydrogen; $R_6$ is hydrogen; $R_7$ is hydrogen; $R_{10}$ is selected from lower alkyl and lower haloalkyl; and m is as defined in formula IX.

In another embodiment of the present invention, compounds have formula IX wherein, $R_1$ is —$S(O)_2R_9$; $R_7$ is hydrogen; and $R_2$, $R_4$, $R_6$, and $R_9$ are as defined in formula I; and m is as defined in formula IX.

In another embodiment of the present invention, compounds have formula IX wherein, $R_1$ is —$S(O)_2R_9$; $R_7$ is hydrogen; $R_9$ is selected from lower alkyl and lower haloalkyl; and $R_2$, $R_4$, and $R_6$ are as defined in formula I; and m is as defined in formula IX.

In another embodiment of the present invention, compounds have formula IX wherein, $R_1$ is —$S(O)_2R_9$; $R_2$ is hydrogen; $R_4$ is hydrogen; $R_6$ is hydrogen; $R_7$ is hydrogen; $R_9$ is selected from lower alkyl and lower haloalkyl; and m is as defined in formula IX.

In another embodiment of the present invention, compounds have formula IX wherein, $R_1$ is —$S(O)_2R_9$; $R_7$ is hydrogen; $R_9$ is ethyl; and $R_2$, $R_4$, and $R_6$ are as defined in formula I; and m is as defined in formula IX.

In another embodiment of the present invention, compounds have formula IX wherein, $R_1$ is —$S(O)_2R_9$; $R_2$ is hydrogen; $R_4$ is hydrogen; $R_6$ is hydrogen; $R_7$ is hydrogen; $R_9$ is ethyl; and m is as defined in formula IX.

In another embodiment of the present invention, compounds have formula IX wherein, $R_1$ is —$S(O)_2R_9$; $R_2$ is hydrogen; $R_4$ is hydrogen; $R_6$ is hydrogen; $R_7$ is hydrogen; $R_9$ is ethyl; and m is 1.

In another embodiment of the present invention, compounds have formula IX wherein, $R_1$ is —$S(O)_2R_9$; $R_7$ is hydrogen; $R_9$ is 2,2,2-trifluoroethyl; and $R_2$, $R_4$, and $R_6$ are as defined in formula I; and m is as defined in formula IX.

In another embodiment of the present invention, compounds have formula IX wherein, $R_1$ is —$S(O)_2R_9$; $R_2$ is hydrogen; $R_4$ is hydrogen; $R_6$ is hydrogen; $R_7$ is hydrogen; $R_9$ is 2,2,2-trifluoroethyl; and m is as defined in formula IX.

In another embodiment of the present invention, compounds have formula IX wherein, $R_1$ is —$S(O)_2R_9$; $R_2$ is hydrogen; $R_4$ is hydrogen; $R_6$ is hydrogen; $R_7$ is hydrogen; $R_9$ is 2,2,2-trifluoroethyl; and m is 1.

In another embodiment of the present invention, compounds have formula X:

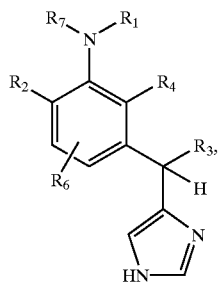

X or a pharmaceutically acceptable salt, amide, ester, or prodrug thereof, wherein $R_1$ is —$S(O)_2R_9$; $R_3$ is hydrogen; $R_9$ is ethyl; and $R_2$, $R_4$, $R_6$, and $R_7$ are as defined in formula I.

Another embodiment of the the present invention includes a pharmaceutical composition comprising a therapeutically effective amount of a compound of formula I–X in combination with a pharmaceutically acceptable carrier.

Another embodiment of the the present invention includes a method of activating $\alpha_1$ adrenoceptors in a host mammal in need of such treatment comprising administering a therapeutically effective amount of a compound of formula I–X.

Another embodiment of the the present invention includes a method of treating urinary incontinence in a host mammal in need of such treatment comprising administering a therapeutically effective amount of a compound of formula I–X.

Another embodiment of the the present invention includes a method of treating retrograde ejaculation in a host mammal in need of such treatment comprising administering a therapeutically effective amount of a compound of formula I–X.

Definition of Terms

The term "alkenyl," as used herein, refers to a straight or branched chain hydrocarbon containing from 2 to 10 carbons and containing at least one carbon-carbon double bond formed by the removal of two hydrogens. Representative examples of "alkenyl" include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl and the like.

The term "alkenyloxy," as used herein, refers to a alkenyl group, as defined herein, appended to the parent molecular moiety through an oxygen atom. Repesentative examples of alkenyloxy include, but are not limited to 4-pentenyloxy, 3 butenyloxy, ethenyloxy, and the like The term "alkoxy," as used herein, refers to an alkyl group, as defined herein, appended to the parent molecular moiety through an oxy group, as defined herein. Representative examples of alkoxy include, but are not limited to, methoxy, ethoxy, propoxy, 2-propoxy, butoxy, tert-butoxy, pentyloxy, hexyloxy and the like.

The term "alkoxycarbonyl," as used herein, refers to an alkoxy group, as defined herein, appended to the parent molecular moiety through a carbonyl group, as defined herein. Representative examples of alkoxycarbonyl include, but are not limited to, methoxycarbonyl, ethoxycarbonyl, tert-butoxycarbonyl, and the like.

The term "alkyl," as used herein, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like.

The term "alkylcarbonyl," as used herein, refers to an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, 1-oxopentyl, and the like.

The term "alkylcarbonylalkyl," as used herein, refers to an alkylcarbonyl group, as defined herein, appended to the parent molecular moiety through an alkyl group, as defined herein. Representative examples of alkylcarbonylalkyl include, but are not limited to, 2-oxopropyl, 3,3-dimethyl-2-oxopropyl, 3-oxobutyl, 3-oxopentyl, and the like.

The term "alkylcarbonyloxy," as used herein, refers to an alkylcarbonyl group, as defined herein, appended to the parent molecular moiety through an oxy group, as defined herein. Representative examples of alkylcarbonyloxy include, but are not limited to, acetyloxy, ethylcarbonyloxy, tert-butylcarbonyloxy, and the like.

The term "alkylthio," as used herein, refers to an alkyl group, as defined herein, appended to the parent molecular moiety through a thio group, as defined herein. Representative examples of alkylthio include, but are not limited, methylsulfanyl, ethylsulfanyl, tert-butylsulfanyl, hexylsulfanyl, and the like.

The term "alkynyl," as used herein, refers to a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, 1-butynyl and the like.

The term "alkynyloxy," as used herein, refers to a alkynyl group, as defined herein, appended to the parent molecular moiety through an oxygen atom. Repesentative examples of alkynyloxy include, but are not limite to 4-pentynyloxy, 3 butynyloxy, ethynyloxy, and the like.

The term "amino," as used herein, refers to a —$NH_2$ group.

The term "aryl," as used herein, refers to a monocyclic-ring system or a bicyclic-fused ring system wherein one or more of the fused rings are aromatic. Representative examples of aryl include, but are not limited to, azulene, indanyl, indenyl, naphthyl, phenyl, tetrahydronaphthyl, and the like.

The aryl groups of this invention can be substituted with 1, 2, 3, 4, or 5 substituents independently selected from alkenyl, alkoxy, alkoxycarbonyl, alkyl, alkylcarbonyl, alkylcarbonyloxy, alkylthio, alkynyl, arylalkoxycarbonyl, carboxy, cyano, cycloalkyl, cycloalkylalkyl, formyl, halo, haloalkyl, hydroxy, hydroxyalkyl, mercapto, nitro, —$NZ_1Z_2$, ($NZ_1Z_2$)alkyl, —C(O)$NZ_1Z_2$, and —$SO_2NZ_1Z_2$.

The term "arylalkenyl," as used herein, refers to an aryl group, as defined herein, appended to the parent molecular moiety through an alkenyl group, as defined herein. Representative examples of arylalkenyl include, but are not limited to, 2-phenylethenyl, 3-phenylpropen-1-yl, 2-naphth-2-ylethenyl, and the like.

The term "arylalkoxy," as used herein, refers to an aryl group, as defined herein, appended to the parent molecular moiety through an alkoxy group, as defined herein. Representative examples of arylalkoxy include, but are not limited to, 2-phenylethoxy, 3-naphth-2-ylpropoxy, 5-phenylpentyloxy, and the like.

The term "arylalkoxycarbonyl," as used herein, refers to an arylalkoxy group, as defined herein, appended to the parent molecular moiety through a carbonyl group, as defined herein. Representative examples of arylalkoxycarbonyl include, but are not limited to, benzyloxycarbonyl, naphth-2-ylmethoxycarbonyl, and the like.

The term "arylalkyl," as used herein, refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-ylethyl, and the like.

The term "carbonyl," as used herein, refers to a —C(O)— group.

The term "carboxy," as used herein, refers to a —$CO_2H$ group.

The term "cyano," as used herein, refers to a —CN group.

The term "cycloalkyl," as used herein, refers to a saturated cyclic hydrocarbon group containing from 3 to 8 carbons. Representative examples of cycloalkyl include, but are not limited to, cyclopropyl, cyclobutyl, cyclopentyl, cyclohexyl, cycloheptyl, cyclooctyl and the like.

The cycloalkyl groups of this invention can be substituted with 1, 2, or 3 substituents independently selected from alkoxy, alkoxycarbonyl, alkylthio, carboxy, formyl, halo, haloalkyl, hydroxy, lower alkyl, mercapto, —$NZ_1Z_2$, and —C(O)$NZ_1Z_2$.

The term "cycloalkylalkyl," as used herein, refers to cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl and 4-cycloheptylbutyl, and the like.

The term "formyl," as used herein, refers to a —C(O)H group.

The term "halo" or "halogen," as used herein, refers to —Cl, —Br, —I or —F.

The term "haloalkyl," as used herein, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, 2-chloro-3-fluoropentyl, and the like.

The term "heterocycle" or "heterocyclic," as used herein, refers to a monocyclic or bicyclic ring system. The monocyclic ring system is exemplified by any 5-, 6- or 7-membered ring containing one, two or three heteroatoms wherein the heteroatoms are independently selected from nitrogen, oxygen and sulfur. The 5-membered ring has from 0–2 double bonds and the 6- and 7-membered ring have from 0–3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system. Representative examples of bicyclic ring systems include but are not limited to, for example, benzimidazole, benzothiazole, benzothiophene, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, pyranopyridine, quinoline, quinolizine, quinoxaline, quinazoline, tetrahydroisoquinoline, tetrahydroquinoline, thiopyranopyridine, and the like.

The heterocycles of this invention can be substituted with 1, 2,or 3 substituents independently selected from alkenyl, alkoxy, alkoxycarbonyl, alkyl, alkylcarbonyl, alkylcarbonyloxy, alkylthio, alkynyl, arylalkoxycarbonyl, carboxy, cyano, cycloalkyl, cycloalkylalkyl, formyl, halo, haloalkyl, hydroxy, hydroxyalkyl, mercapto, nitro, —$NZ_1Z_2$, ($NZ_1Z_2$)alkyl, —C(O)$NZ_1Z_2$, and —$SO_2NZ_1Z_2$.

The term "hydroxy," as used herein, refers to an —OH group.

The term "hydroxyalkyl," as used herein, refers to a hydroxy group, as defined herein, appended to the parent molecular moiety through an alkyl group, as defined herein. Representative examples of hydroxyalkyl include, but are not limited to, hydroxymethyl, 2-hydroxyethyl, 3-hydroxypropyl, 2-ethyl-4-hydroxyheptyl, and the like.

The term "lower alkoxy," as used herein, refers to a lower alkyl group, as defined herein, appended to the parent molecular moiety through an oxy group, as defined herein. Representative examples of lower alkoxy include, but are not limited to, methoxy, ethoxy, propoxy, 2-propoxy, butoxy, tert-butoxy, and the like.

The term "lower alkyl," as used herein, refers to a straight or branched chain hydrocarbon group containing from 1-to-4 carbon atoms. Representative examples of lower alkyl include, but are not limited to, methyl, ethyl, n-propyl, iso-propyl, n-butyl, iso-butyl, tert-butyl, and the like.

The term "lower haloalkyl," as used herein, refers to at least one halogen, as defined herein, appended to the parent molecular moiety through a lower alkyl group, as defined herein. Representative examples of lower haloalkyl include, but are not limited to, fluoromethyl, difluoromethyl, trifluoromethyl, pentafluoroethyl, chloromethyl, 3-chloropropyl, 2-fluoroethyl, 2,2,2-trifluoroethyl, 2,2-difluoroethyl, and the like.

The term "mercapto," as used herein, refers to a —SH group.

The term "nitro," as used herein, refers to a —$NO_2$ group.

The term "—NZ$_1$Z$_2$," as used herein, refers to two groups, Z$_1$ and Z$_2$, which are appended to the parent molecular moiety through a nitrogen atom. Z$_1$ and Z$_2$ are independently selected from hydrogen, alkyl, alkylcarbonyl, aryl, arylalkyl, and formyl. Representative examples of —NZ$_1$Z$_2$ include, but are not limited to, amino, benzylamino, methylamino, acetylamino, acetylmethylamino, and the like.

The term "(NZ$_1$Z$_2$)alkyl," as used herein, refers to a —NZ$_1$Z$_2$ group, as defined herein, appended to the parent molecular moiety through an alkyl group, as defined herein. Representative examples of (NZ$_1$Z$_2$)alkyl include, but are not limited to, aminomethyl, benzylaminomethyl, methylaminomethyl, acetylaminomethyl, acetylmethylaminomethyl, and the like.

The term "oxy," as used herein, refers to (—O—).

The term "sulfonyl," as used herein, refers to a —S(O)$_2$— group.

The term "thio," as used herein, refers to (—S—).

Compounds of the present invention may exist as stereoisomers where asymmetric or chiral centers are present. The present invention contemplates various stereoisomers and mixtures thereof. Stereoisomers include enantiomers and diastereomers. Individual stereoisomers of compounds of the present invention can be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Geometric isomers can also exist in the compounds of the present invention. The present invention contemplates the various geometric isomers and mixtures thereof resulting from the arrangement of substituents around a carbon-carbon double bond. Substituents around a carbon-carbon double bond are designated as being in the (Z) or (E) configuration where the term (Z) represents substituents on the same side of the carbon-carbon double bond and the term (E) represents substituents on opposite sides of the carbon-carbon double bond. Geometric isomers of the present invention can be separated into individual (E) and (Z) isomers by chromatography such as flash chromatography, medium pressure liquid chromatography, or high pressure liquid chromatography. Geometric isomers can also exist in the compounds of the present invention resulting from the arrangement of substituents around a ring. The arrangement of substituents around a ring are designated as cis or trans where the term "cis" represents substituents on the same side of the plane of the ring and the term "trans" represents substituents on opposite sides of the plane of the ring. Mixtures of compounds where the substitutients are disposed on both the same and opposite sides of plane of the ring are designated "cis/trans."

Preferred compounds of formula I include,

N-{3-[1-(1H-imidazol-4-yl)ethyl]-2,4-dimethylphenyl}ethanesulfonamide,
N-{3-[1-(1H-imidazol-4-yl)ethyl]-2,6-dimethylphenyl}ethanesulfonamide,
N-{6-ethyl-3-[1-(1H-imidazol-4-yl)ethyl]-2-methylphenyl}ethanesulfonamide,
N-{5-[1-(1H-imidazol-4-yl)ethyl]-2-methylphenyl}ethanesulfonamide,
N-{3-[1-(1H-imidazol-4-yl)ethyl]-4-methylphenyl}ethanesulfonamide,
N-{5-[1-(1H-imidazol-4-yl)ethyl]-2,4-dimethylphenyl}ethanesulfonamide,
N-{3-[1-(1H-imidazol-4-yl)ethyl]-2,4,6-trimethylphenyl}ethanesulfonamide,
N-{3-[1-(1H-imidazol-4-yl)ethyl]-2-methylphenyl}ethanesulfonamide,
N-{3-fluoro-5-[1-(1H-imidazol-4-yl)ethyl]-2-methylphenyl}ethanesulfonamide,
N-{5-fluoro-3-[1-(1H-imidazol-4-yl)ethyl]-2-methylphenyl}ethanesulfonamide,
N-{3-fluoro-5-[1-(1H-imidazol-4-yl)ethyl]-4-methylphenyl}ethanesulfonamide,
N-{3-[1-(1H-imidazol-4-yl)propyl]-2-methylphenyl}ethanesulfonamide,
N-{3-[1-(1H-imidazol-4-yl)propyl]-4-methylphenyl}ethanesulfonamide,
N-{5-[1-(1H-imidazol-4-yl)propyl]-2-methylphenyl}ethanesulfonamide,
N-{3-[1-(1H-imidazol-4-yl)ethyl]-2-methoxy-6-methylphenyl}ethanesulfonamide,
N-{2-hydroxy-3-[1-(1H-imidazol-4-yl)ethyl]-6-methylphenyl}ethanesulfonamide,
N-[3-(1H-imidazol-4-ylmethyl)-2,4,6-trimethylphenyl]ethanesulfonamide,
N-[5-(1H-imidazol-4-ylmethyl)-2-methylphenyl]ethanesulfonamide,
N-[5-(1H-imidazol-4-ylmethyl)-2,4-dimethylphenyl]ethanesulfonamide,
N-[3-(1H-imidazol-4-ylmethyl)-4-methylphenyl]ethanesulfonamide,
N-[3-(1H-imidazol-4-ylmethyl)-2,4-dimethylphenyl]ethanesulfonamide,
N-[3-(1H-imidazol-4-ylmethyl)-2,6-dimethylphenyl]ethanesulfonamide,
N-[6-ethyl-3-(1H-imidazol-4-ylmethyl)-2-methylphenyl]ethanesulfonamide,
N-[2-ethyl-3-(1H-imidazol-4-ylmethyl)-4-methylphenyl]ethanesulfonamide,
N-[3-fluoro-5-(1H-imidazol-4-ylmethyl)-2-methylphenyl]ethanesulfonamide,
N-[5-fluoro-3-(1H-imidazol-4-ylmethyl)-2-methylphenyl]ethanesulfonamide,
N-[3-fluoro-5-(1H-imidazol-4-ylmethyl)-4-methylphenyl]ethanesulfonamide,
N-[3-(1H-imidazol-4-ylmethyl)-2-methoxyphenyl]ethanesulfonamide,
N-[2-hydroxy-3-(1H-imidazol-4-ylmethyl)phenyl]ethanesulfonamide,
N-[5,6,7,8-tetrahydro-5-(4-thiazolyl)-1-naphthalenyl]ethanesulfonamide,
N-[5,6,7,8-tetrahydro-5-(4-oxazolyl)-1-naphthalenyl]ethanesulfonamide,
N-[5-(2-amino-4-thiazolyl)-5,6,7,8-tetrahydro-1-naphthalenyl]ethanesulfonamide,
N-[5-(2-amino-4-oxazolyl)-5,6,7,8-tetrahydro-1-naphthalenyl]ethanesulfonamide,
N-[5-(2-amino-1H-imidazol-4-yl)-5,6,7,8-tetrahydro-1-naphthalenyl]ethanesulfonamide,
N-[3-[1-(1H-imidazol-4-yl)-1-methylethyl]phenyl]ethanesulfonamide,
N-[3-[1-(1H-imidazol-4-yl)cyclopropyl]phenyl]ethanesulfonamide,
N-[5,6,7,8-tetrahydro-5-(5-methyl-1H-imidazol-4-yl)-1-naphthalenyl]ethanesulfonamide,
N-[5,6,7,8-tetrahydro-5-(1H-imidazol-4-yl)-5-methyl-1-naphthalenyl]ethanesulfonamide, N-[2,3-dihydro-3-(1H-imidazol-5-yl)-1-benzothiophen-7-yl]ethanesulfonamide,
N-[1,3-dihydro-1-(1H-imidazol-5-yl)-4-isobenzofuranyl]ethanesulfonamide,
N-[1,3-dihydro-1-(1H-imidazol-5-yl)-2-benzothiophen-4-yl]ethanesulfonamide,
N-[3-[1-(1H-imidazol-5-yl)-2-phenylethenyl]phenyl]ethanesulfonamide,
N-[3-[1-(H-imidazol-5-yl)-3-methyl-1-butenyl]phenyl]ethanesulfonamide,
N-[3-[1-(1H-imidazol-5-yl)-2-methyl-1-propenyl]phenyl]ethanesulfonamide,
N-[3-(cyclopentylidene1H-imidazol-5-ylmethyl)phenyl]ethanesulfonamide,
N-[3-[1-(1H-imidazol-5-yl)-1-butenyl]-2-methylphenyl]ethanesulfonamide,
N'-[5-(1H-imidazol-5-yl)-5,6,7,8-tetrahydro-1-naphthalenyl]-N,N-dimethylsulfamide,
N-[5,6,7,8-tetrahydro-5-(1H-imidazol-5-yl)-1-naphthalenyl]-1-piperidinesulfonamide,
ethyl 5-(1H-imidazol-5-yl)-5,6,7,8-tetrahydro-1-naphthalenylcarbamate,
benzyl 5-(1H-imidazol-5-yl)-5,6,7,8-tetrahydro-1-naphthalenylcarbamate,
N-[5-(1H-imidazol-5-yl)-5,6,7,8-tetrahydro-1-naphthalenyl]urea,
N-[5-(1H-imidazol-5-yl)-5,6,7,8-tetrahydro-1-naphthalenyl]-N'-phenylurea,
N-[5-(1H-imidazol-5-yl)-5,6,7,8-tetrahydro-1-naphthalenyl]-N'-isopropylurea,
N-[2-ethyl-1,2,3,4-tetrahydro-1-(1H-imidazol-5-yl)-5-isoquinolinyl]ethanesulfonamide,
N-[3,4-dihydro-1-(1H-imidazol-5-yl)-1H-2-benzothiopyran-5-yl]ethanesulfonamide,
N-[1,2,3,4-tetrahydro-4-(1H-imidazol-5-yl)-2-methyl-8-isoquinolinyl]ethanesulfonamide,
N-[3,4-dihydro-4-(1H-imidazol-5-yl)-1H-2-benzothiopyran-8-yl]ethanesulfonamide,
N-[1,2,3,4-tetrahydro-4-(1H-imidazol-5-yl)-8-quinolinyl]ethanesulfonamide, and
N-[3,4-dihydro-4-(1H-imidazol-5-yl)-2H-1-benzothiopyran-8-yl]ethanesulfonamide and pharmaceutically acceptable salts, esters, amides, or prodrugs thereof.

More preferred compounds of formula I include,

N-[5-(1H-imidazol-4-yl)-2-methoxy-5,6,7,8-tetrahydro-1-naphthalenyl]methanesulfonamide,
N-[2-hydroxy-5-(1H-imidazol-4-yl)-5,6,7,8-tetrahydro-1-naphthalenyl]methanesulfonamide,
N-[2-hydroxy-5-(1-methyl-1H-imidazol-5-yl)-5,6,7,8-tetrahydro-1-naphthalenyl]methanesulfonamide,
N-[2-hydroxy-5-(1-methyl-1H-imidazol-4-yl)-5,6,7,8-tetrahydro-1-naphthalenyl]methanesulfonamide,
N-[2-hydroxy-5-(1-methyl-1H-imidazol-4-yl)-5,6,7,8-tetrahydro-1-naphthalenyl]methanesulfonamide,
N-[5-(1-ethyl-1H-imidazol-4-yl)-2-hydroxy-5,6,7,8-tetrahydro-1-naphthalenyl]methanesulfonamide,
N-[2-hydroxy-5-(1-propyl-1H-imidazol-4-yl)-5,6,7,8-tetrahydro-1-naphthalenyl]methanesulfonamide,
N-[5-(1H-imidazol-4-yl)-5,6,7,8-tetrahydro-1-naphthalenyl]methanesulfonamide,
(R)-N-[5-(1H-imidazol-4-yl)-5,6,7,8-tetrahydro-1-naphthalenyl]methanesulfonamide,
(S)-N-[5-(1H-imidazol-4-yl)-5,6,7,8-tetrahydro-1-naphthalenyl]methanesulfonamide,
N-[2-hydroxy-5-(1H-imidazol-4-ylmethyl)phenyl]methanesulfonamide,
N-[5-(1H-imidazol-4-yl)-5,6,7,8-tetrahydro-1-naphthalenyl]ethanesulfonamide,
N-[5,6,7,8-tetrahydro-5-(1-methyl-1H-imidazol-4-yl)-1-naphthalenyl]methanesulfonamide,
N-[5,6,7,8-tetrahydro-5-(1H-imidazol-4-yl)-1-naphthalenyl]-N-methylmethanesulfonmamide,
N-[5,6,7,8-tetrahydro-5-(1H-imidazol-4-yl)-1-naphthalenyl]acetamide,
2,2,2-trifluoro-N-[5-(1H-imidazol-4-yl)-5,6,7,8-tetrahydro-1-naphthalenyl]acetamide,
N-[5,6,7,8-tetrahydro-5-(1H-imidazol-4-yl)-1-naphthalenyl]-2-methylethanesulfonamide,
N-[4-(1H-imidazol-4-yl)-3,4-dihydro-2H-chromen-8-yl]methanesulfonamide,
N-[5,6,7,8-tetrahydro-5-(1H-imidazol-4-yl)-1-naphthalenyl]-2,2,2-trifluoroethanesulfonamide,
N-[3-(1H-imidazol-4-ylmethyl)phenyl]methanesulfonamide,
N-[1-(1H-imidazol-4-yl)-2,3-dihydro-1H-inden-4-yl]methanesulfonamide,
N-[5,6,7,8-tetrahydro-5-(1H-imidazol-4-yl)-4-methyl-1-naphthalenyl]methanesulfonamide,
N-[5,6,7,8-tetrahydro-4-hydroxy-5-(1H-imidazol-4-yl)-1-naphthalenyl]methanesulfonamide,
N-[5,6,7,8-tetrahydro-(1H-imidazol-4-yl)-4-methoxy-1-naphthalenyl]ethanesulfonamide,
N-[5,6,7,8-tetrahydro-(1H-imidazol-4-yl)-4-methoxy-1-naphthalenyl]methanesulfonamide,
N-[5,6,7,8-tetrahydro-(1H-imidazol-4-yl)-1-naphthalenyl]cyclopropanesulfonamide,
N-[3-(1H-imidazol-4-ylmethyl)-2-methylphenyl]methanesulfonamide,
N-[3-(1H-imidazol-4-ylmethyl)-2-methylphenyl]ethanesulfonamide,
N-[3-(1H-imidazol-4-ylmethyl)phenyl]ethanesulfonamide,
N-[3-(1-(1H-imidazol-4-yl)ethyl)phenyl]methanesulfonamide,
(+)-N-[5-(1H-imidazol-4-yl)-5,6,7,8-tetrahydro-1-naphthalenyl]ethanesulfonamide,
(−)-N-[5-(1H-imidazol-4-yl)-5,6,7,8-tetrahydro-1-naphthalenyl]ethanesulfonamide,
(−)-N-[5,6,7,8-tetrahydro-5-(1H-imidazol-4-yl)-1-naphthalenyl]-2,2,2-trifluoroethanesulfonamide,
(+)-N-[5,6,7,8-tetrahydro-5-(1H-imidazol-4-yl)-1-naphthalenyl]-2,2,2-trifluoroethanesulfonamide,
N-[3-(1-(1H-imidazol-4-yl)ethyl)phenyl]ethanesulfonamide,
N-[5-(1H-imidazol-4-yl)-6,7,8,9-tetrahydro-5H-benzo[a]cyclohepten-1-yl]methanesulfonamide,
N-[1-(1H-imidazol-4-yl)-2,3-dihydro-1H-inden-4-yl]ethanesulfonamide,
N-[5-(1H-imidazol-4-yl)-6,7,8,9-tetrahydro-5H-benzo[a]cyclohepten-1-yl]ethanesulfonamide, [4-fluoro-3-(1H-imidazol-4-ylmethyl)phenyl]methanesulfonamide,
N-[4-chloro-5-(1H-imidazol-4-yl)-5,6,7,8-tetrahydro-1-naphthalenyl]ethanesulfonamide,
N-[4-chloro-5-(1H-imidazol-4-yl)-5,6,7,8-tetrahydro-1-naphthalenyl]methanesulfonamide,
N-[4-fluoro-5-(1H-imidazol-4-yl)-5,6,7,8-tetrahydro-1-naphthalenyl]methanesulfonamide,
N-[3-(1-(1H-imidazol-4-yl)vinyl)phenyl]ethanesulfonamide,
N-{3-[(Z)-1-(1H-imidazol-4-yl)-2-methoxyethenyl]phenyl}ethanesulfonamide,
N-[5-(1H-imidazol-4-yl)-7,8-dihydro-1-naphthalenyl]methanesulfonamide,
N-[3-(1-hydroxy-1-(1H-imidazol-4-yl)propyl)phenyl]ethanesulfonamide,
N-[3-(cyclohexylidene-(1H-imidazol-4-ylmethyl)phenyl]ethanesulfonamide,
N-[5-(1H-imidazol-4-yl)-5,6,7,8-tetrahydro-1-naphthalenyl]-3,5-dimethyl-4-isoxazolesulfonamide,
N-[5-(1H-imidazol-4-yl)-5,6,7,8-tetrahydro-1-naphthalenyl]-1-propanesulfonamide, N-[5-(1H-imidazol-4-yl)-5,6,7,8-tetrahydro-1-naphthalenyl]-1-butanesulfonamide,
3-chloro-N-[5-(1H-imidazol-4-yl)-5,6,7,8-tetrahydro-1-naphthalenyl]-1-propanesulfonamide,
N-[5-(1H-imidazol-4-yl)-5,6,7,8-tetrahydro-1-naphthalenyl]-1-methyl-1H-imidazole-4-sulfonamide,
N-[5-(1H-imidazol-4-yl)-5,6,7,8-tetrahydro-1-naphthalenyl](phenyl)methanesulfonamide,
N-[5-(1H-imidazol-4-yl)-5,6,7,8-tetrahydro-1-naphthalenyl]-4-methylbenzenesulfonamide,
N-[5-(1H-imidazol-4-yl)-5,6,7,8-tetrahydro-1-naphthalenyl]-2-methylbenzenesulfonamide,
N-[5-(1H-imidazol-4-yl)-5,6,7,8-tetrahydro-1-naphthalenyl]-2-phenyl-1-ethenesulfonamide,
N-[5-(1H-imidazol-4-yl)-5,6,7,8-tetrahydro-1-naphthalenyl]-4-methoxybenzenesulfonamide,
5-chloro-N-[5-(1H-imidazol-4-yl)-5,6,7,8-tetrahydro-1-naphthalenyl]-2-thiophenesulfonamide,
N-[5-(1H-imidazol-4-yl)-5,6,7,8-tetrahydro-1-naphthalenyl]-8-quinolinesulfonamide,
5-chloro-N-[5-(1H-imidazol-4-yl)-5,6,7,8-tetrahydro-1-naphthalenyl]-1,3-dimethyl-1H-pyrazole-4-sulfonamide,
methyl 2-{[(5-(1H-imidazol-4-yl)-5,6,7,8-tetrahydro-1-naphthalenyl)amino]sulfonyl}-3-thiophenecarboxylate,
N-(5-{[(5-(1H-imidazol-4-yl)-5,6,7,8-tetrahydro-1-naphthalenyl)amino]sulfonyl}-4-methyl-1,3-thiazol-2-yl)acetamide,
5-chloro-N-[5-(1H-imidazol-4-yl)-5,6,7,8-tetrahydro-1-naphthalenyl]-3-methyl-2,3-dihydro-1-benzothiophene-2-sulfonamide,
2,2,2-trifluoro-N-[3-(1H-imidazol-4-ylmethyl)phenyl]ethanesulfonamide,
N-[4-(1H-imidazol-4-yl)-3,4-dihydro-2H-chromen-8-yl]ethanesulfonamide,
N-[6-fluoro-4-(1H-imidazol-4-yl)-3,4-dihydro-2H-chromen-8-yl]ethanesulfonamide, and
N-{3-[(E)-1-(1H-imidazol-4-yl)-2-methoxyethenyl]phenyl}ethanesulfonamide and pharmaceutically acceptable salts, esters, amides, or prodrugs thereof.

Abbreviations

Abbreviations which have been used in the descriptions of the schemes and the examples that follow are: DMF for N,N-dimethylformamide; NBS for N-bromosuccinimide, NCS for N-chlorosuccinimide, PPA for polyphosphoric acid, pyr for pyridine, and THF for tetrahydrofuran.

Preparation of Compounds of the Invention

The compounds and processes of the present invention will be better understood in connection with the following synthetic schemes and methods which illustrate a means by which the compounds of the invention can be prepared.

The compounds of this invention can be prepared by a variety of synthetic routes. Representative procedures are shown in Schemes 1–38.

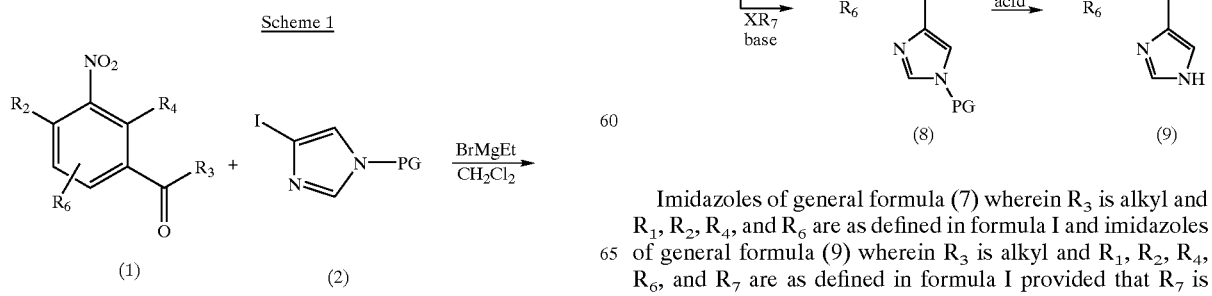

Imidazoles of general formula (7) wherein $R_3$ is alkyl and $R_1$, $R_2$, $R_4$, and $R_6$ are as defined in formula I and imidazoles of general formula (9) wherein $R_3$ is alkyl and $R_1$, $R_2$, $R_4$, $R_6$, and $R_7$ are as defined in formula I provided that $R_7$ is other than aryl, can be prepared as illustrated in Scheme 1.

Nitroketones of general formula (1) are treated with a 4-iodoimidazole of general formula (2), wherein PG is N,N-dimethylsulfamoyl prepared according to (R. M. Turner, J. Org. Chem. (1991), 56, 5739–5740), in the presence of ethyl magnesium bromide to provide the alcohols of general formula (3). The intermediate alcohols of general formula (3) can be dehydrated under acidic conditions (such as aqueous HCl, para-toluenesulfonic acid, trifluoroacetic acid or the like) to afford the unsaturated products of general formula (4) wherein $R_{12}$ and $R_{15}$ are independently selected from hydrogen and alkyl. Hydrogenation of compounds of general formula (4) using a catalyst (such as palladium on carbon or the like) in a solvent (such as methanol, ethyl acetate or the like) provides anilines of general formula (5). Anilines of general formula (5) can be treated with sulfonylating agents (such as sulfonyl chlorides) or acylating agents (such as anhydrides or acid chlorides) using a mild base (such as pyridine) in a solvent (such as dichloromethane) to provide compounds of general formula (6). The imidazole protecting group, N,N-dimethylsulfamoyl, can be cleaved under acidic conditions (such as refluxing aqueous HCl) to provide imidazoles of general formula (7).

Compounds of general formula (6) can be treated with a strong non nucleophilic base (such as sodium hydride or the like) in a solvent (such as DMF or the like) and electrophiles such as alkyl halides, alkenyl halides, alkynyl halides, arylalkyl halides, cycloalkyl halides, or cycloalkylalkyl halides to provide compounds of general formula (8). The imidazole protecting group, N,N-dimethylsulfamoyl, can be cleaved under acidic conditions (such as refluxing aqueous HCl) to provide imidazoles of general formula (9).

In the case of compounds of general formula (7) and (9) wherein $R_2$ is alkoxy, treatment of (7) or (9) with a Lewis acid (such as $BBr_3$) in a solvent (such as dichloromethane) can provide compounds of general formula (7) or (9) wherein $R_2$ is hydroxy.

Nitroketones can be purchased commercially or can be prepared using the procedures described in (Blumer, Helv.Chim.Acta, (1949), 32, 2547, 2551), (Claus, J.Prakt.Chem. (1890), 41, 493), (Adams, R., J.Amer.Chem.Soc. (1961), 83, 2559–2563), (Binder, D. Arch.Pharm.(Weinheim Ger.), (1980), 313, 587–602), and (Kaye, J.Chem.Soc.; (1964), 2816).

Scheme 2

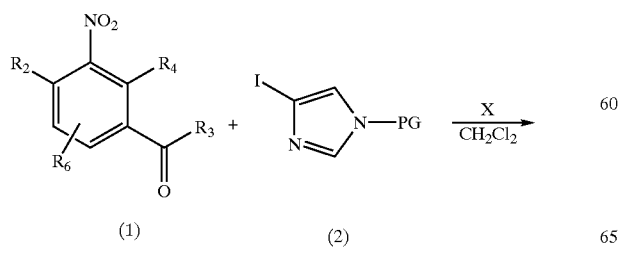

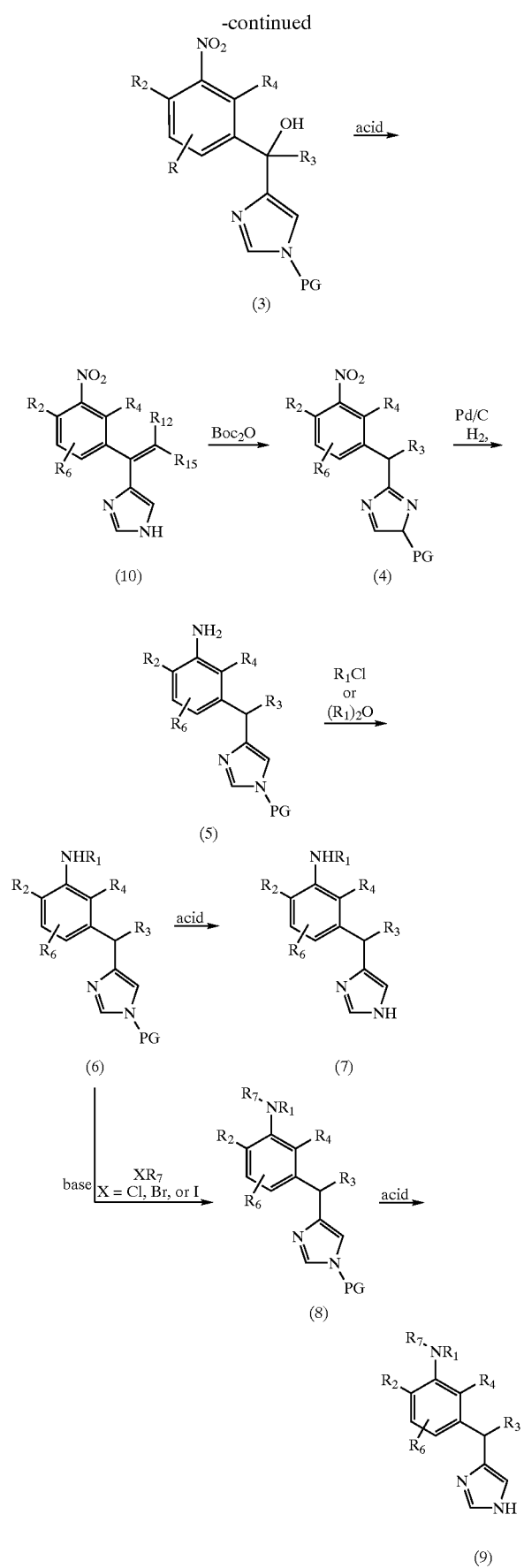

Scheme 2 illustrates an alternative method for preparing imidazoles of general formula (7) wherein $R_3$ is alkyl and $R_1$, $R_2$, $R_4$, and $R_6$ are as defined in formula I and imidazoles of general formula (9) wherein $R_3$ is alkyl and $R_1$, $R_2$, $R_4$, $R_6$, and $R_7$ are as defined in formula I provided that $R_7$ is other than aryl. Nitroketones of general formula (1) are treated with a 4-iodoimidazole of general formula (2), wherein PG is an acid labile protecting group such as triphenylmethyl prepared according to (K. Kirk, J. Het. Chem. (1985), 22, 57–59), in the presence of ethyl magnesium bromide to provide the alcohols of general formula (3) wherein PG is triphenylmethyl. The intermediate alcohols of general formula (3) can be dehydrated under acidic conditions (such as aqueous HCl, para-toluenesulfonic acid, trifluoroacetic acid or the like) to afford the unsaturated products of general formula (10) wherein $R_{12}$ and $R_{15}$ are independently selected from hydrogen and alkyl. Compounds of general formula (10) can be reprotected with an acid labile protecting group such as Boc to provide compounds of general formula (4) wherein PG is Boc. The procedures described in Scheme 1 can be used to provide imidazoles of general formula (7) and (9) wherein Boc is removed under acidic conditions, for example aqueous HCl with or without a cosolvent such as methanol or THF.

Scheme 3

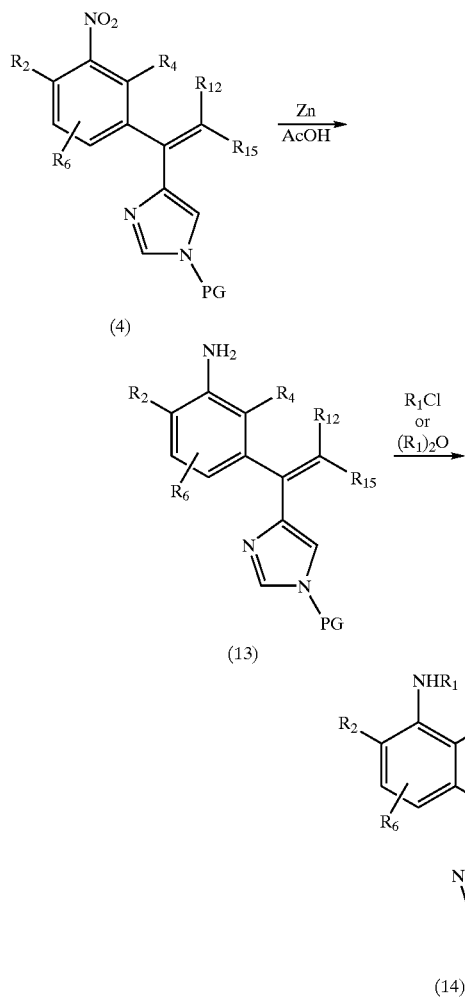

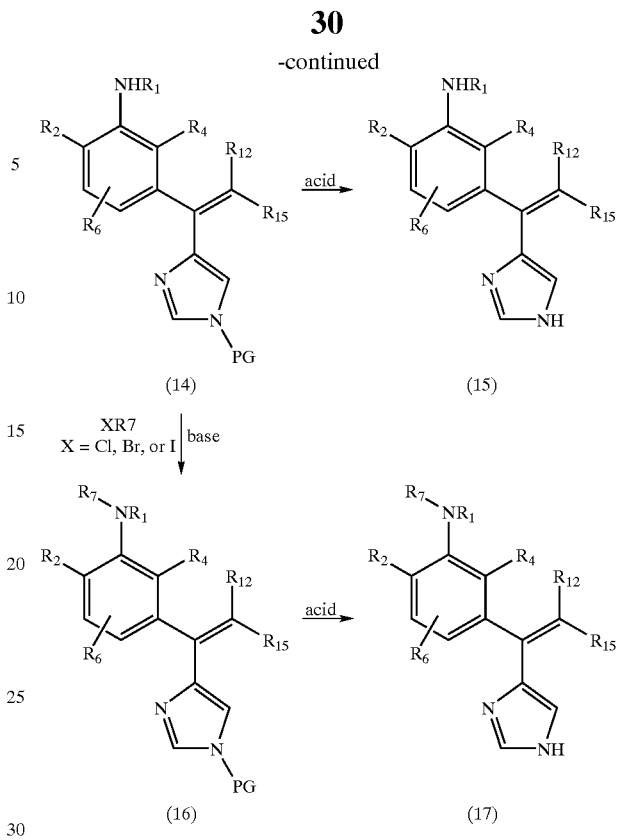

Imidazoles of general formula (15) and (17) wherein $R_1$, $R_2$, $R_4$, $R_6$, and $R_7$ are as defined in formula I and $R_{12}$ and $R_{15}$ are independently selected from hyrdrogen and alkyl, cna be prepared as illustrated in Scheme 3. Nitroimidazoles of general formula 4, wherein PG is Boc, can be reduced to the aniline without reduction of the carbon carbon double bond using a metal such as zinc in a solvent such as acetic acid. The resulting aniline of general formula (13) is treated with an acylating or sulfonylating agent using a mild base (such as pyridine) in a solvent (such as dichloromethane) to provide compounds of general formula (14). Intermediates of general formula (14) can be deprotected with acid (for example aqueous HCl with or without a cosolvent such as methanol or THF) to provide compounds of general formula (15) or treated with an alkylating agent using a strong non nucleophilic base (such as sodium hydride or the like) in a solvent (such as DMF or the like) to provide compounds of general formula (16). Removal of the imidazole protecting group of (16) under acidic conditions (for example aqueous HCl with or without a cosolvent such as methanol or THF) provides imidazoles of general formula (17).

Scheme 4

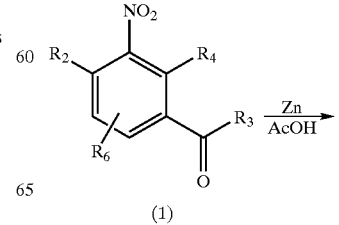

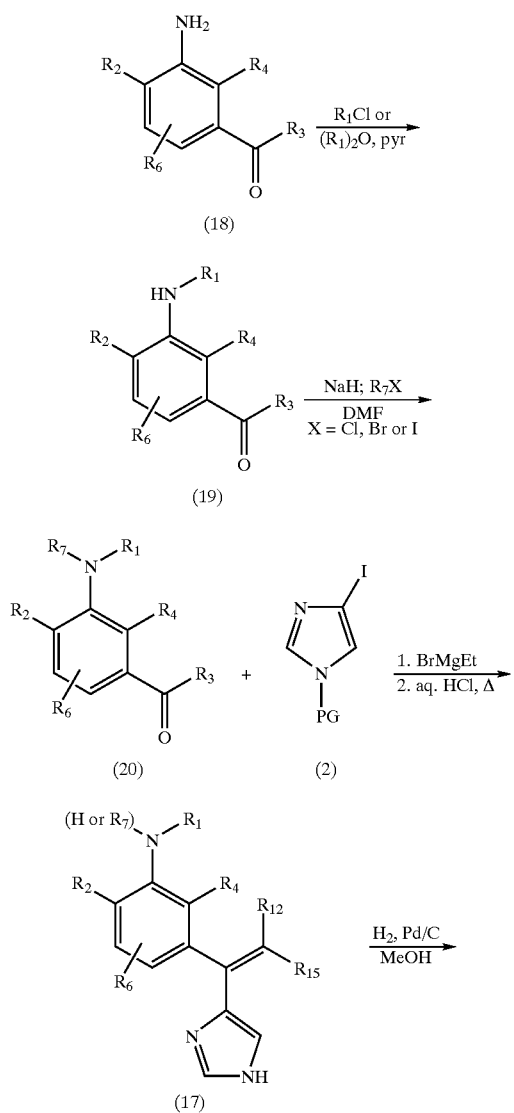
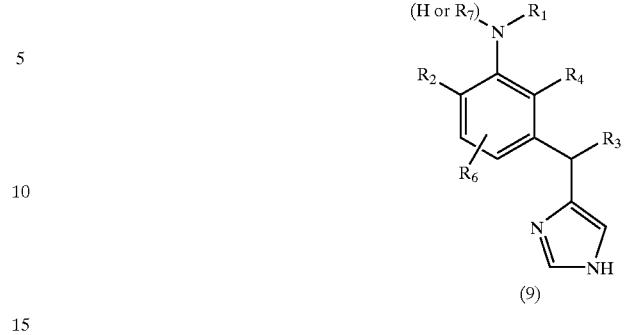

An alternative method for preparing imidazoles of general formula (9) and (17), wherein $R_3$ is alkyl, $R_1$, $R_2$, $R_4$, $R_6$, and $R_7$ are as defined in formula I provided that $R_7$ is other than aryl, and $R_{12}$ and $R_{15}$ are selected from hydrogen and alkyl, can be prepared as illustrated in Scheme 4. Nitroketones of general formula (1) can be reduced using a metal such as zinc in acetic acid to provide anilines of general formula (18). Anilines of general formula (18) can be acylated or sulfonylated using acid chlorides, anhydrides, or sulfonyl chlorides in the presence of a mild base (such as pyridine) in a solvent (such as dichloromethane) to provide compounds of general formula (19). Ketones of general formula (19) can be treated with an alkylating agent (such as benzyl bromide, chloromethyl methyl ether, alkyl iodide or the like) using a strong non nucleophilic base (such as sodium hydride or the like) in a solvent (such as DMF or the like) to provide ketones of general formula (20) wherein $R_7$ is other than hydrogen. Ketones of general formula (20) can be treated with the imidazole Grignard reagent of general formula (2) as described in Scheme 1 or Scheme 2 to provide an intermediate alcohol which is not isolated but subjected to acidic conditions (such as heating in aqueous HCl) to provide the unsaturated imidazole of general formula (17) with possible loss of $R_7$ when $R_7$ is acid sensitive (for example methoxymethyl or the like). Hydrogenation of (17) using a catalyst (such as palladium on carbon or the like) in a solvent (such as methanol) reduces the non aromatic carbon-carbon double bond and may remove $R_7$ when $R_7$ is benzyl (or the like) to provide imidazoles of general formula (9).

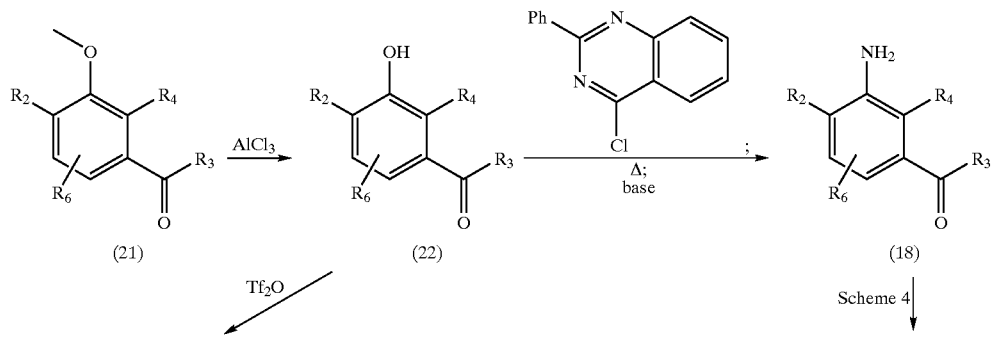

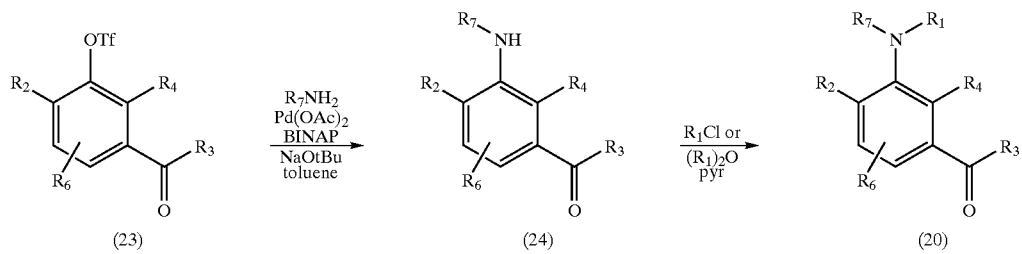

Alternate methods of preparing anilines of general formula (20), wherein $R_3$ is alkyl, $R_1$, $R_2$, $R_4$, $R_6$, and $R_7$ are as defined in formula I, are illustrated in Scheme 5. Substituted methoxyketones of general formula (21) can be converted to phenols of general formula (22) with a Lewis acid ($AlCl_3$ or the like) in a solvent (dichloromethane or the like). Conversion of phenols (22) to the desired amino ketones of general formula (18) can be carried out via an intermediate quinazoline which is thermally rearranged to a quinazolinone and cleaved by base as described in (Newman, A. H. J. Med. Chem. (1992), 35, 4135–4142). Compounds (18) can be transformed into compounds of general formula (20) and thereafter to compounds of the invention using procedures analogous to those described in Scheme 4.

Phenols (22) alternatively can be treated with trifluoromethane sulfonic anhydride in the presence of a non nucleophilic base (such as 2,6-di-tert-butyl-4-methylpyridine or the like) in a solvent (such as dichloromethane) to provide the phenyl trifluoromethanesulfonates of general formula (23). Treatment of sulfonates (23) with a primary amine such as benzyl amine or optionally substituted anilines in the presence of a palladium catalyst such as palladium (II) acetate under conditions described by Buchwald (J. Org. Chem. (1997), 62, 1264–1267) can provide compounds of general formula (24). Compounds of general formula (24) can be treated with an acylating or sulfonating agents (such as sulfonyl chlorides, anhydrides, acid chlorides, or the like) using a mild base (such as pyridine) in a solvent (such as dichloromethane) to provide compounds of general formula (20).

Scheme 6

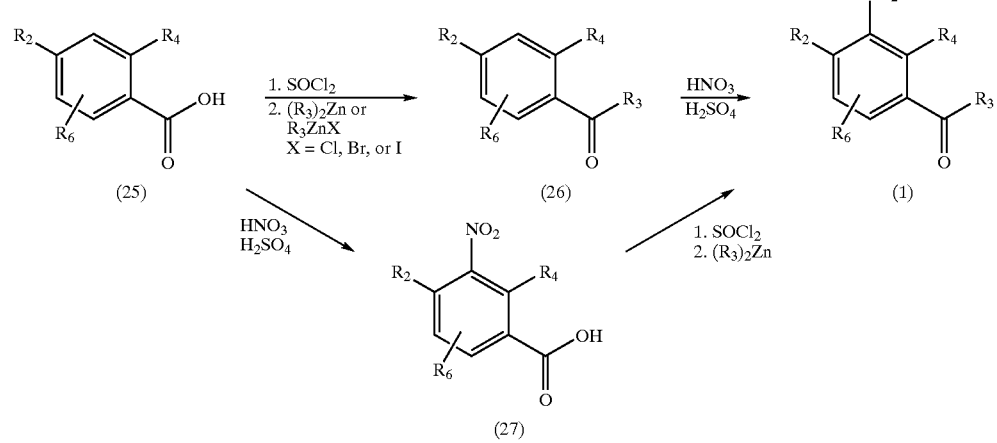

Alternate methods of preparing nitroketones of general formula (1), wherein $R_3$ is alkyl, $R_2$, $R_4$, and $R_6$ are as defined in formula I, are illustrated in Scheme 6. Benzoic acids of general formula (25) can be treated with thionyl chloride or the like to provide acid chlorides which can then be treated with alkyl zinc reagents such as dimethyl zinc in the presence of a catalyst such as trans-benzyl(chloro)bis(triphenylphosphine)palladium(II) in a solvent such as tetrahydrofuran to provide ketones of general formula (26). Ketones of general formula (26) can be nitrated (for example with nitric acid in sulfuric acid) to provide nitroketones (1). Alternatively, acids (25) can be nitrated to provide nitroacids (27) which can be converted via the above method to nitroketones (1).

Benzoic acids can be purchased commercially or can be prepared using the procedures described in(Claus, J.Prakt.Chem. (1890), 41, 500), (DE 1247323), and (Baumgarth, M. J.Med.Chem. (1997), 40,2017–2034).

Imidazoles of general formula (33) and (32), wherein $R_1$, $R_2$, $R_4$, $R_6$, and $R_7$ are as defined in formula I provided that $R_7$ is other than aryl, can be prepared as illustrated in Scheme 7. Nitrobenzaldehydes of general formula (28) can be treated with Grignard (2) from Scheme 1 or Scheme 2 to provide alcohols of general formula (29). Removal of the imidazole protecting group followed by hydrogenation using a catalyst (such as palladium on carbon or the like) in a solvent (such as methanol, ethyl acetate or the like) provides anilines of general formula (31). Anilines of general formula (31) can be treated with acylating or sulfonylating agents (such as sulfonyl chlorides, anhydrides, acid chlorides or the like) using a mild base (such as pyridine) in a solvent (such as dichloromethane) to provide imidazoles of general formula (32). Deoxygenation of (32) using triethylsilane in trifluoroacetic acid or the like provides imidazoles of general formula (33) wherein $R_7$ is hydrogen.

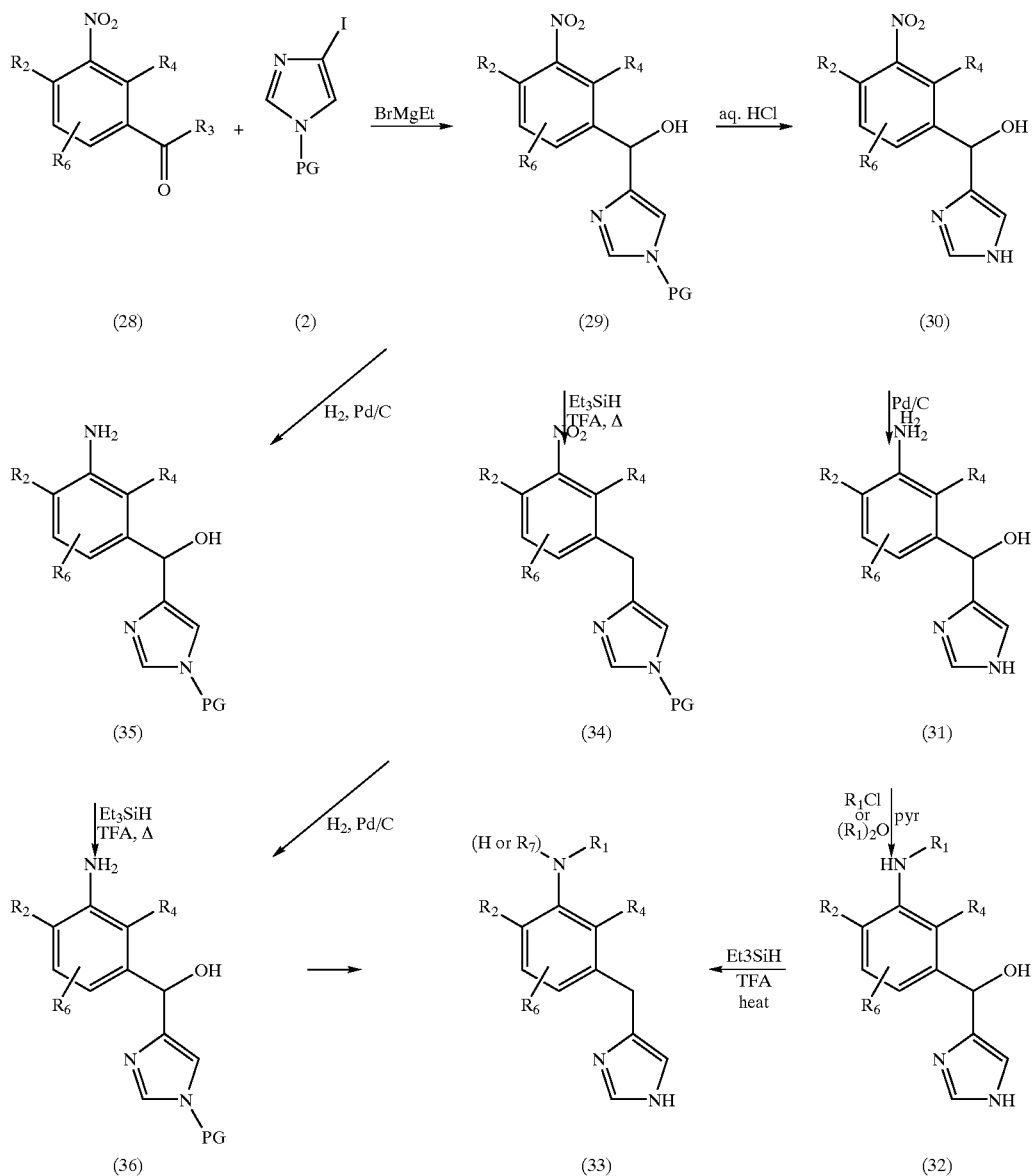

Scheme 7

Alternatively, compounds of general formula (29) can be dehydrated using triethylsilane in trifluoroacetic acid to provide imidazoles of general formula (34) which can be reduced to compounds of general formula (36) via hydrogenation with a catalyst such as Pd/C in a solvent such as methanol or ethyl acetate. Anilines of general formula (36) can be treated as previously described in (Scheme 1 or Scheme 2 for transformation of (5) to (7) or transformation of (5) to (9)) to provide compounds of general formula (33).

Imidazoles of general formula (29) can also be hydrogenated with a catalyst such as Pd/C in a solvent such as methanol or ethyl acetate to provide anilines of general formula (35). Deoxygenation of (35) provides (36) which can be processed as described above to provide imidazoles of general formula (33).

Nitrobenzaldehydes can be purchased commercially or can be prepared using the procedures described in (Hinkel, J.Chem.Soc. (1931), 1170), (Fieser, J.Amer.Chem.Soc. (1936), 58; 2052), (Gattermann, Justus Liebigs Ann. Chem. (1906), 347; 372), (Goh, S. H. J.Chem.Soc.Perkin Trans.1, (1981), 423–426), and (Asahina, Chem.Ber. (1936), 69, 1367).

condtions, for example, to aldehydes of general formula (39). Aldehydes of general formula (39) can be nitrated (for example with nitric acid in sulfuric acid) to provide nitro aldehydes of general formula (28).

Alternatively, acids (25) can be nitrated to provide nitroacids of general formula (27) which can be reduced to nitroalcohols of general formula (40) by treatment with borane-tetrahydrofuran complex or the like in a solvent such as THF. The nitroalcohols (40) can be oxidized to the corresponding aldehydes (28) via conditions such as the Swern oxidation.

Alternatively, the esters of general formula (41), wherein R is lower alkyl, can be hydrolyzed to acids (25) and processed as described above. The esters (41) can also be nitrated to provide intermediate nitroesters of general formula (42) which can be reduced using sodium borohydride or the like in a solvent such as ethanol to provide the nitroalcohols (40) which can be processed as described above.

Benzoic acids, benzoic esters, and nitrobenzaldehydes can be purchased commercially or can be prepared using the

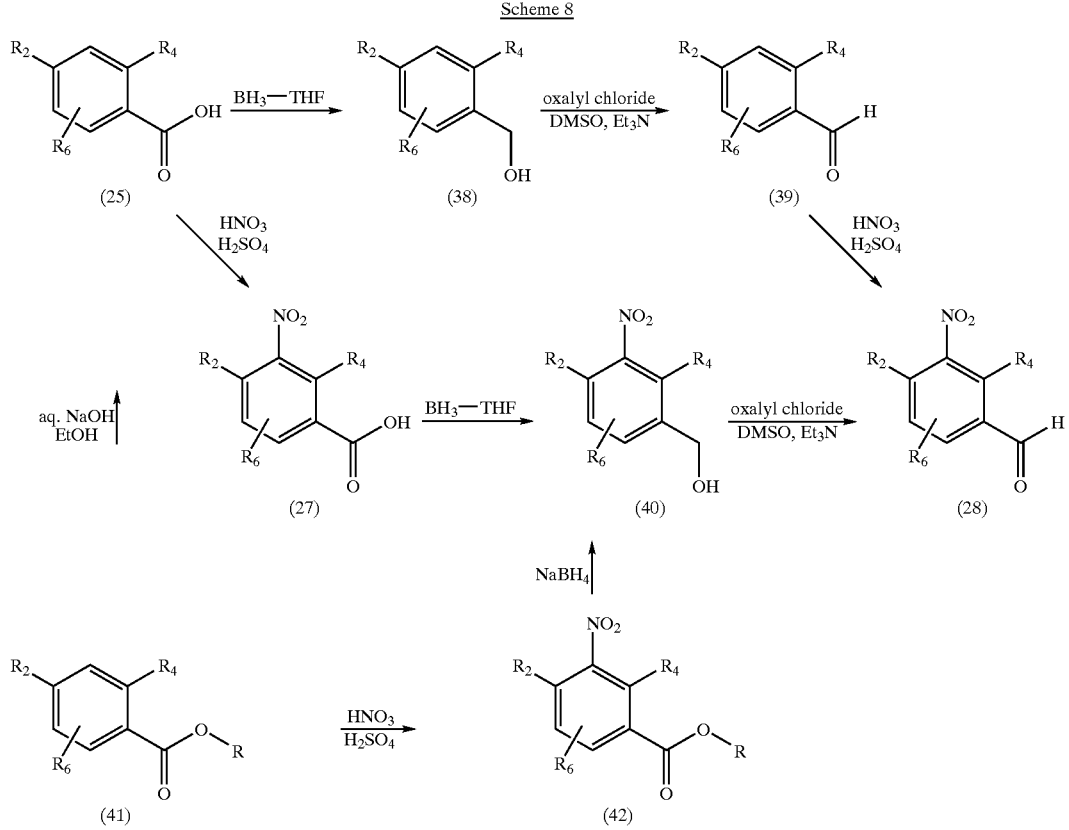

Scheme 8

Alternative methods for preparing nitroaldehydes of general formula (28), wherein $R_2$, $R_4$, and $R_6$ are as defined in formula I are illustrated in Scheme 8. Acids of general formula (25) can be reduced to the corresponding alcohols of general formula (38) using standard reaction conditions known to those of ordinary skill in the art. Alcohols of general formula (38) can be oxidized under Swern procedures described in (Bennett, L. J.Med.Chem. (1981), 24, 382–389), (Weissensteiner, W. J.Org.Chem. (1987), 52, 1210–1215), (Baciocchi, E. Tetrahedron Lett. (1991), 32, 2647–2650), (Kessar, S. V. J.Chem.Soc.Chem.Commun. (1992), 11, 840–841), (Claus, J.Prakt.Chem. (1890),.41, 500), (DE 1247323), and (Baumgarth, M. J.Med.Chem. 1997, 40, 2017–2034).

Scheme 9

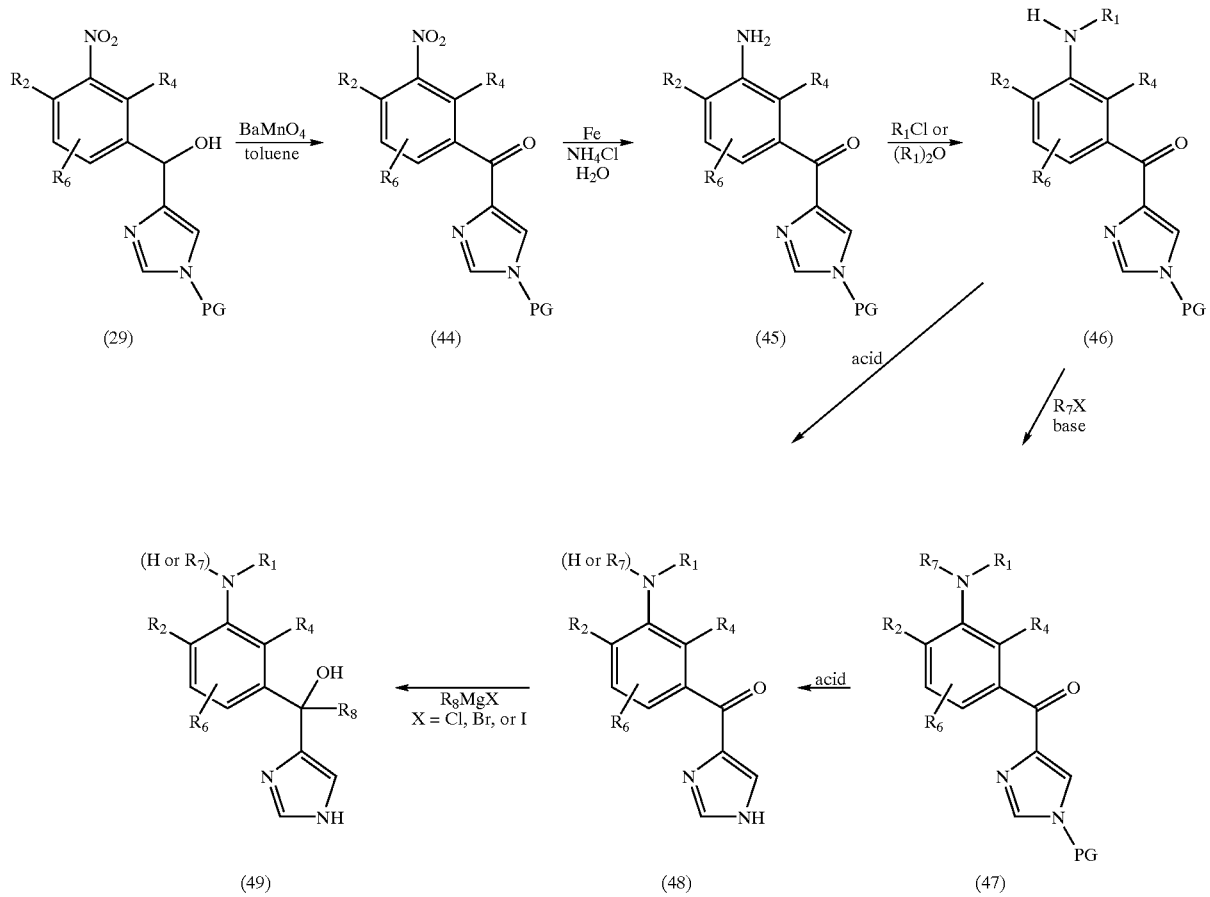

Imidazoles of general formula (49), wherein $R_8$ is alkyl and $R_1$, $R_2$, $R_4$, $R_6$, and $R_7$ are as defined in formula I, can be prepared as illustrated in Scheme 9. Nitroalcohols of general formula (29). from Scheme 7 can be oxidized to ketones of general formula (44) using an oxidant such as barium manganate in a solvent such as toluene. Nitroketones (44) can be reduced to anilines of general formula (45) using a metal such as iron in the presence of aqueous ammonium chloride. Anilines (45) can be treated with acylating or sulfonylating agents (such as sulfonyl chlorides, anhydrides, acid chlorides, or the like) to provide ketones of general formula (46). To prepare compounds wherein $R_7$ is alkyl, compounds (46) can be treated with alkylating agents (such as an alkyl iodide, benzyl bromide or the like) using a strong non nucleophilic base (such as sodium hydride or the like) in a solvent (such as DMF or the like) to provide N-alkylated products of general formula (47). The protecting group of the imidazole can be removed in (46) or (47) under acidic conditions to provide the imidazoles of general formula (48). Treatment of (48) with Grignard reagents provides alcohols of general formula (49).

Scheme 10

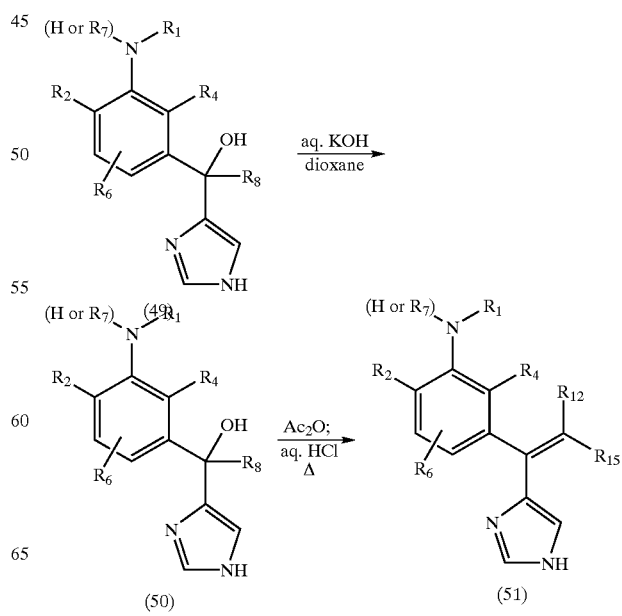

An alternative method for preparing imidazoles of general formula (51), wherein $R_1$, $R_2$, $R_4$, $R_6$, and $R_7$ are as defined in formula I and one of $R_{12}$ and $R_{15}$ is hydrogen and the other is alkyl, is illustrated in Scheme 10. Cleavage of the imidazole protecting group from (49) with a base such as potassium hydroxide in a solvent such as aqueous dioxane provides the unprotected alcohols of general formula (50). Deoxygenation of (50) can be accomplished by treatment with acetic anhydride in the presence of a base such as pyridine followed by heating in the presence an acid such as aqueous HCl to provide the imidazoles of general formula (51).

Scheme 12

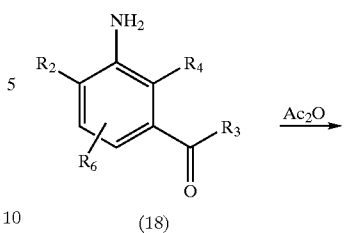

(18)

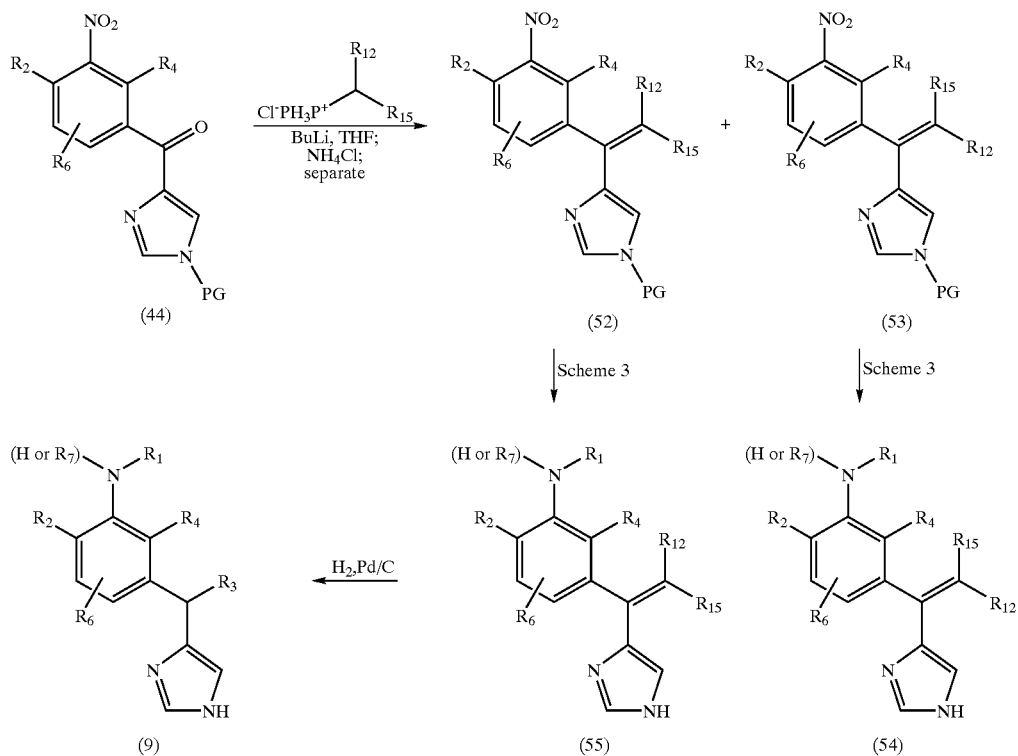

Imidazoles of general formula (9), (54), and (55), wherein $R_1$, $R_2$, $R_4$, $R_6$, $R_7$, $R_{12}$, and $R_{15}$ are as defined in formula I and $R_3$ is selected from alkyl, alkoxyalkyl, arylalkyl, cycloalkylalkyl, and haloalkyl, can be prepared as illustrated in Scheme 11. Nitroketones of general formula (44) can be treated with phosphonium reagents (Wittig reaction) or phosphonates (Horner-Wadsworth-Emmons reaction) in the presence of a base in a solvent such as THF to provide a mixture of unsaturated products of general formula (52) and (53) which can be separated by a technique such as chromatography on silica gel. Intermediates (52) and (53) can each be processed individually as described in Scheme 3 to provide unsaturated imidazoles of general formula (54) and (55). Imidazoles of general formulae (54) and (55) can be reduced via hydrogenation catalyzed by palladium on carbon for example to provide imidazoles of general formula (9).

-continued

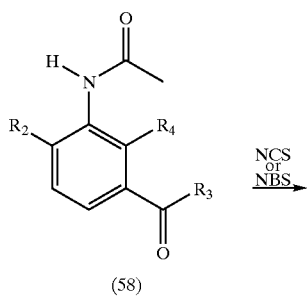

(58)

-continued

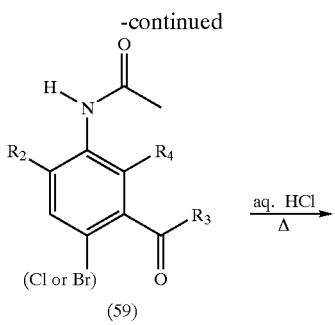

(59)

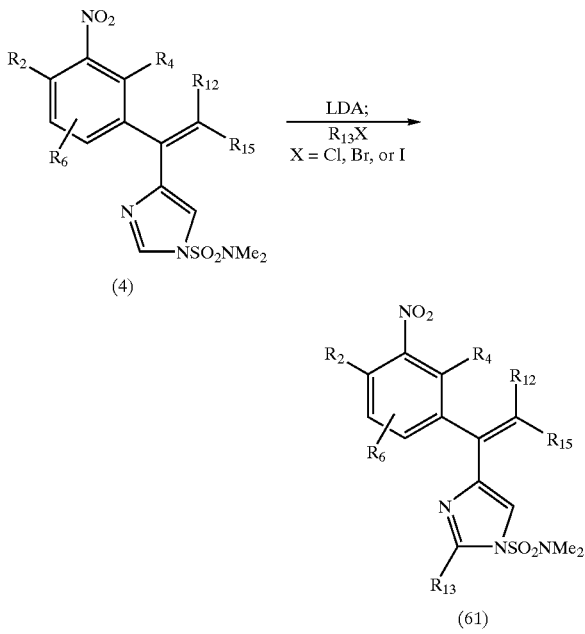

Anilines of general formula (60), wherein $R_3$ is alkyl, $R_2$ and $R_4$ are as defined in formula I, can be prepared as illustrated in Scheme 12. Anilines of general formula (18), wherein $R_6$ is hydrogen, from Scheme 4 can be acylated with acetic anhydride or acetyl chloride and treated with an electophilic source or chlorine or bromine (N-chlorosuccinimide or N-bromosuccinimide for example) in a solvent such as DMF to provide halogenated ketones of general formula (59) which can be deprotected by heating in aqueous acid to provide the ketoanilines of general formula (60) which can be processed into compounds of the invention as described in previous Schemes.

Imidazoles of general formula (61), wherein $R_2$, $R_4$, $R_6$, $R_{12}$, $R_{13}$, and $R_{15}$ are as defined in formula I, can be prepared as illustrated in Scheme 13. Imidazoles of general formula (4), wherein PG is N,N-dimethylsulfamoyl, can be deprotonated at the 2-position of the imidazole ring with a strong non nucleophilic base (such as lithium diisopropylamide) in a solvent (such as THF) and then treated with alkylating agents (such as alkyl iodide, ethyl iodide, or the like) to provide 2-alkylated imidazoles of general formula (61). 2-Alkylated imidazoles of general formula (61) can be processed to compounds of the present invention following procedures described in previous Schemes.

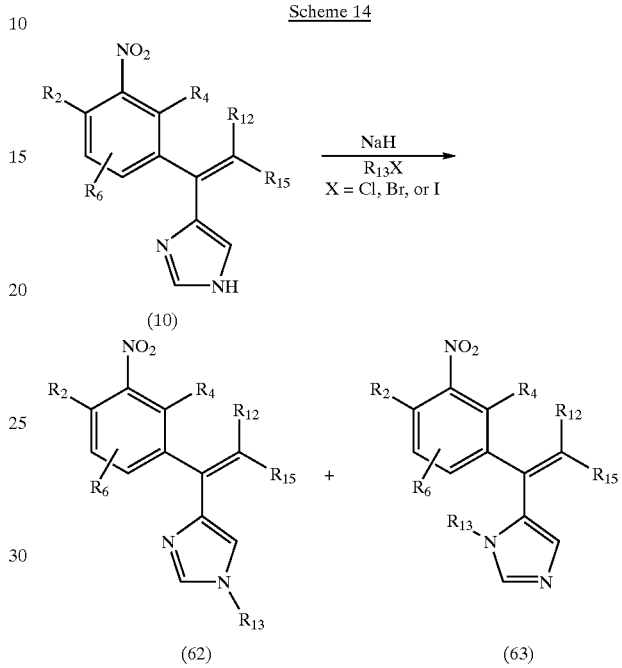

Imidazoles of general formula (62) and (63), wherein $R_2$, $R_4$, $R_6$, $R_{12}$, $R_{13}$, and $R_{15}$ are as defined in formula I, can be prepared as illustrated in Scheme 14. Nitro imidazoles of general formula (10) can be deprotonated with a base (such as sodium hydride or the like) in a solvent (such as DMF) and treated with alkylating reagents (such as an alkyl iodide, ethyl iodide or the like) to provide a mixture of the N-1 and N-3 substituted imidazoles of general formulae (62) and (63) respectively which are separated and processed individually by the procedures described in the previous Schemes to provide compounds of the present invention.

Scheme 15

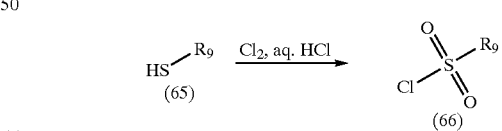

Sulfonyl chlorides of general formula (66), wherein $R_9$ is as defined in formula I, can be prepared as illustrated in Scheme 15. Thiols of general formula (65) can be treated with chlorine under aqueous conditions as described in (Bunyagid, C. J.Chem.Eng.Data, (1981), 26, 344–346) to provide sulfonyl chlorides of general structure (66). Thiols can be purchased commercially or can be prepared using the procedures described in (Harris, J. J.Amer.Chem.Soc. (1963), 85, 749–754) and (Bunyagid, C. J.Chem.Eng.Data, (1981), 26, 344–346).

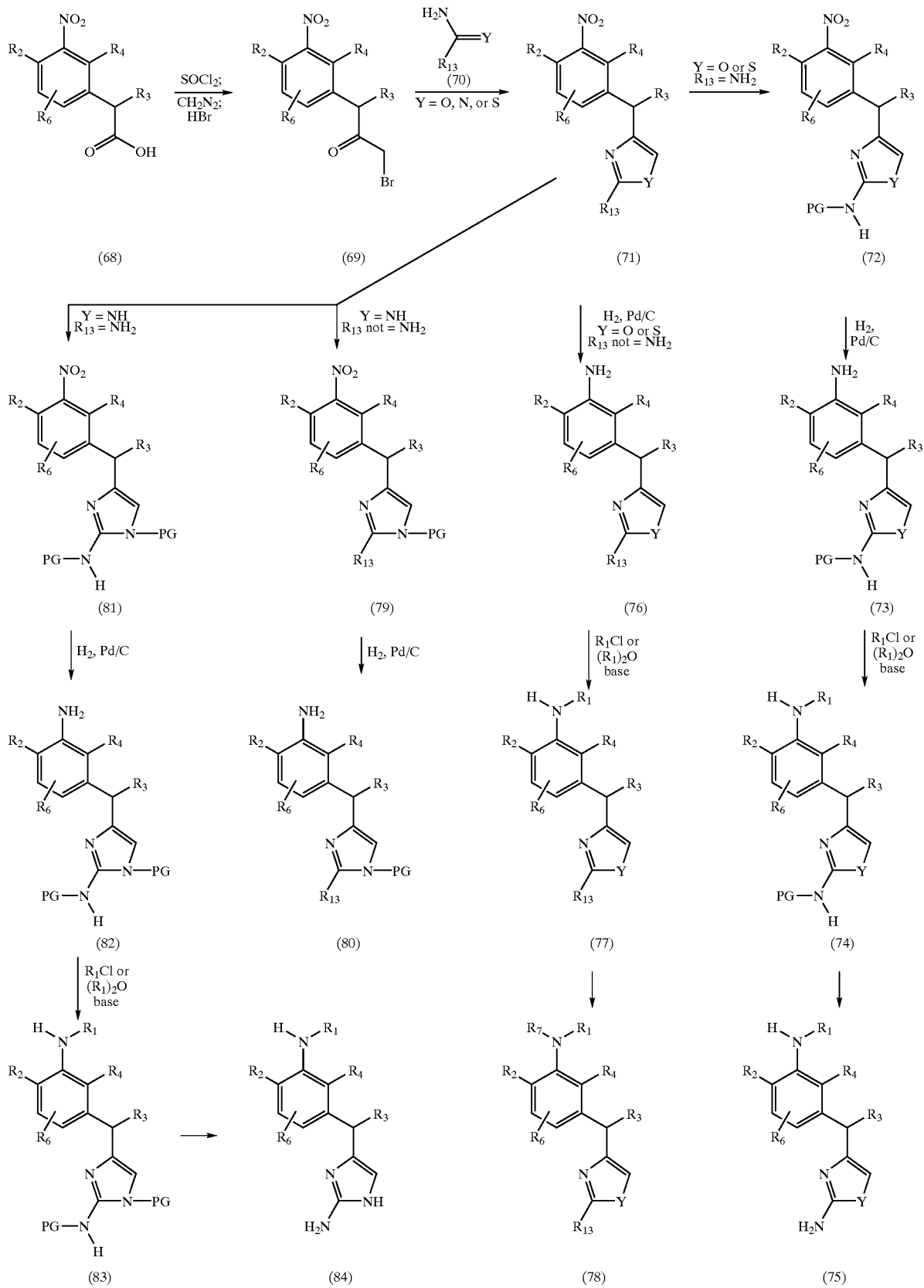
Scheme 16

Compounds of general formula (75), (77), (78), and (84), wherein $R_3$ is selected from hydrogen and alkyl, $R_1$, $R_2$, $R_4$, $R_6$, $R_7$, and $R_{13}$ are as defined in formula I, and Y is selected from NH, O and S, can be prepared as illustrated in Scheme 16. Nitrophenylacetic acids of general formula (68) can be converted to bromoketones of general formula (69) via a standard three step process as described in (Schumack W. Arch. Pharm. (1975), 308, 755–759). Bromoketones (69) can be treated with an appropriate nitrogen containing fragment of general formula (70) wherein Y is selected from NH, O, and S in a solvent (such as DMF) to provide heteroaromatic compounds of general formula (71). Treatment of (69) with formamide at 150° C. as described in (Lynch J. Amer. Chem. Soc. (1994), 116, 11030–11038) provides imidazoles of general formula (71) wherein Y is NH and $R_{13}$ is hydrogen. Treatment of (69) with guanidine as described in (Chabaka Pol. J. Chem. (1994), 68, 1317–1326) provides imidazoles of general formula (71) wherein Y is NH and $R_{13}$ is $NH_2$. Treatment of (69) with urea as described by Gompper in (Chem.Ber. (1959), 92, 1944) provides ozazoles of general formula (71) wherein Y is O and $R_{13}$ is $NH_2$. Treatment of (69) with ammonium formate as described by Whitney in (J.Org.Chem. (1990), 55, 929–935) provides oxazoles of general formula (71) wherein Y is O and $R_{13}$ is hydrogen. Treatment of (69) with acetamide as described by Hammar, W. In (J.Het.Chem. (1981), 18, 885–888) provides oxazoles of general formula (71) wherein Y is O and $R_{13}$ is methyl. Treatment of (69) with thioamidine as described in (Penning J. Med. Chem. (1995), 38, 858–868) and as described in Hara (Heterocycles, (1981), 16, 1295–1299) provides thiazoles of general formula (71) wherein Y is S and $R_{13}$ is hydrogen. Treatment of (69) with thiourea as desribed by Mahajanshetti in (J.Indian Chem.Soc (1962), 39, 420–426) provides thiazoles of general formula (71) wherein Y is S and $R_{13}$ is $NH_2$. Treatment of (69) with thioacetamide as described by Garnaik in (J.Indian Chem.Soc (1988), 65, 435–437) provides thiazoles of general formula (71) wherein Y is S and $R_{13}$ is methyl.

In the case of (71) where Y is O or S and $R_{13}$ is $NH_2$, protection with an appropriate group such as tert-butoxycarbonyl provides heteroaromatic compounds of general formula (72) wherein PG is t-butoxycarbonyl. Heteroaromatic compounds of general formula (72) can be reduced via a catalyst such as palladium on carbon in the presence of hydrogen or by a metal such as zinc in acetic acid to provide anilines of general formula (73). Anilines of general formula (73) can be treated with acylating or sulfonylating agents (such as sulfonyl chlorides, anhydrides, acid chlorides, or the like) using a mild base (such as pyridine) in a solvent (such as dichloromethane) to provide compounds of general formula (74). Removal of the protecting group provides compounds of general formula (75).

In the case of (71) wherein Y is O or S and $R_{13}$ is not $NH_2$, the aromatic nitro group is reduced via a catalyst such as palladium on carbon in the presence of hydrogen or a metal such as zinc in acetic acid to provide anilines of general: formula (76) Anilines of general formula (76) can be treated with acylating or sulfonylating agents (such as sulfonyl chlorides, anhydrides, acid chlorides, or the like) using a mild base (such as pyridine) in a solvent (such as dichloromethane) to give the compounds of general formula (77). To prepare compounds wherein $R_7$ is alkyl, compounds of general formula (77) are treated with alkylating agents (such as an alkyl iodide, ethyl iodide, or the like) using a non nucleophilic base (such as sodium hydride or the like) in a solvent (such as DMF or the like) to provide the N-alkylated compounds of general formula (78).

In the case of (71) wherein Y is NH and $R_{13}$ is not $NH_2$, protection with an appropriate group such as tert-butoxycarbonyl provides compounds of general formula (79). Compounds of general formula (79) can be reduced via a catalyst such as palladium on carbon in the presence of hydrogen or a by metal such as zinc in acetic acid to provide anilines of general formula (80). Anilines of general formula (80) can be processed as described in previous Schemes to provide compounds of the present invention.

In the case of (71) wherein Y is NH and $R_{13}$ is $NH_2$, protection with an appropriate group such as tert-butoxycarbonyl provides compounds of general formula (81). Compounds of general formula (81) can be reduced via a catalyst such as palladium on carbon in the presence of hydrogen or by a metal such as zinc in acetic acid to provide anilines of general formula (82). Anilines of general formula (82) can be treated with acylating or sulfonylating agents (such as sulfonyl chlorides, anhydrides, acid chlorides, or the like) using a mild base (such as pyridine) in a solvent (such as dichloromethane) to provide compounds of general formula (83). Removal of the protecting group provides compounds of general formula (84).

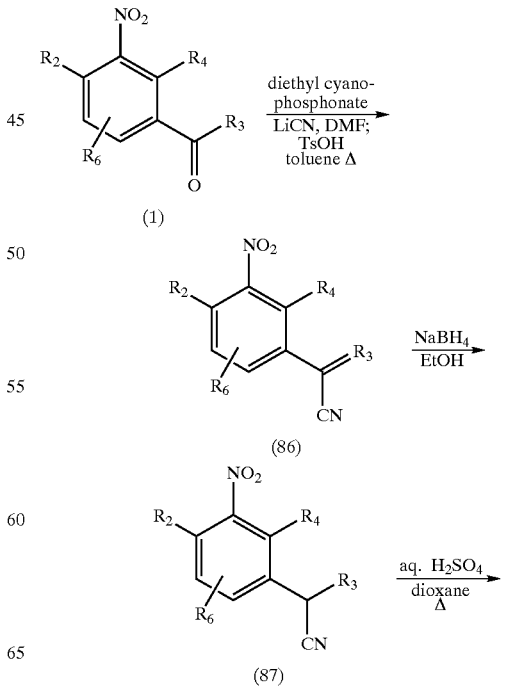

Scheme 17

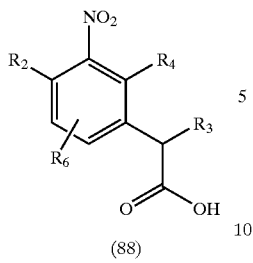

(88)

Nitrophenylacetic acids of general formula (88), wherein R_3 is alkyl and R_2, R_4, and R_6 are as defined in formula I, can be prepared as illustrated in Scheme 17. Ketones of general formula (1) can be converted to unsaturated nitriles of general formula (86) by treatment with an appropriate source of cyanide such as diethyl cyanophosphonate and lithium cyanide in a solvent such as dimethyl formamide followed by treatment of the intermediate with acid under anhydrous conditions such as para-toluenesulfonic acid in toluene at 80° C. Reduction of (86) to provide unsaturated nitriles of general formula (87) can be accomplished with sodium borohydride in a solvent such as ethanol. The nitriles (87) can be hydrolized to acids of general formula (88) which can be processed as described in Scheme 16.

Scheme 18

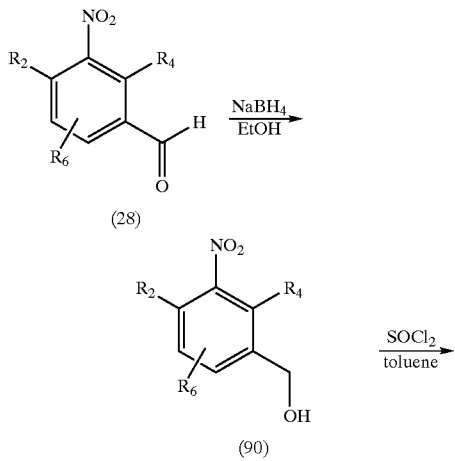

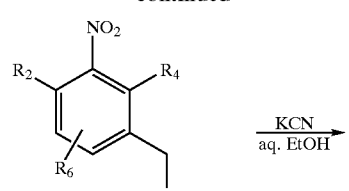

(91)

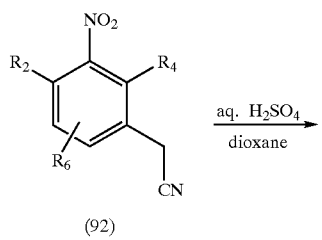

(92)

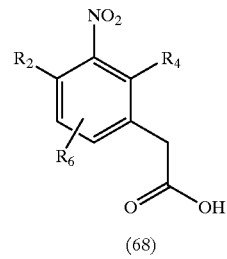

(68)

Nitrophenylacetic acids of general formula (68), wherein R_2, R_4, and R_6 are as defined in formula I, can be prepared as illustrated in Scheme 18. Nitrobenzaldehydes of general formula (28) can be reduced to nitrobenzylic alcohols of general formula (90) using a reducing agent such as sodium borohydride in a solvent such as ethanol. Conversion of alcohols (90) to benzyl chlorides of general formula (91) can be accomplished with thionyl chloride in a solvent such as toluene. Treatment of benzyl chlorides (91) with potassium cyanide in a solvent such as ethanol yields nitrites of general formula (92). Nitriles of general formula (92) can be hydrolized under aqueous acidic conditions to provide acids of general formula (68) which can be processed as described in Scheme 16.

Scheme 19

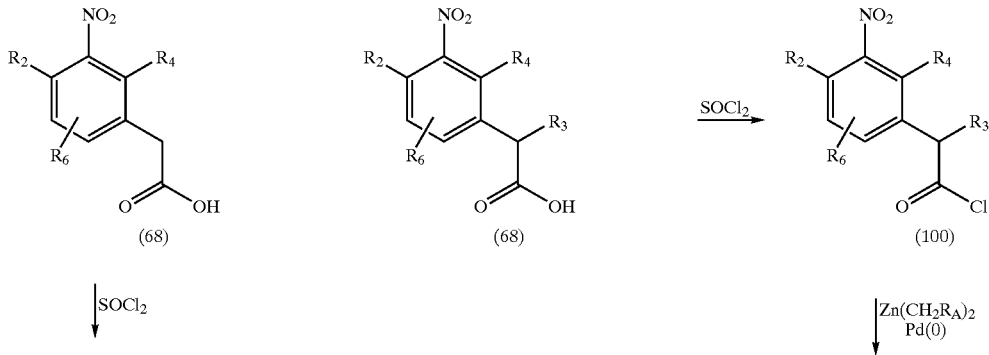

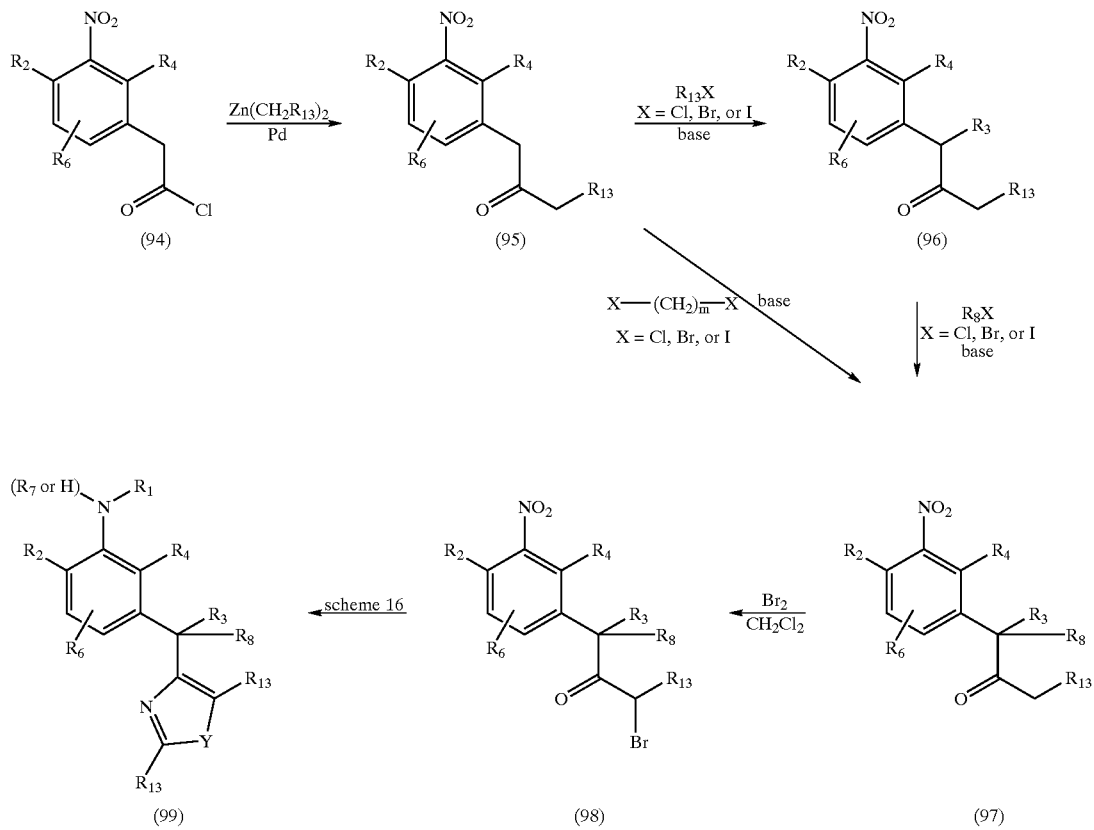

Compounds of general formula (99), wherein $R_1$, $R_2$, $R_4$, $R_6$, $R_7$, $R_8$, and $R_{13}$ are as defined in formula I and $R_3$ is alkyl or $R_3$ and $R_8$ form a 3-, 4-, 5-, or 6-membered carbocyclic ring, can be prepared as illustrated in Scheme 19. Nitrophenylacetic acids of general formula (68) can be treated with thionyl chloride (or oxalyl chloride) to provide acid chlorides of general formula (94). Acid chlorides (94) can be treated with alkyl zinc reagents in the presence of a catalyst such as trans-benzyl(chloro)bis(triphenylphosphine)-palladium(II) in a solvent such as tetrahydrofuran to provide ketones of general formula (95). Ketones of general formula (95) can be monoalkylated at the benzylic position with alkyl halides such as iodomethane or the like in the presence of a base such as potassium hydroxide or the like to provide compounds of general formula (96). Compounds of general formula (96) can be alkylated a second time at the benzylic position with alkyl halides such as iodomethane or the like in the presence of a base such as potassium hydroxide or the like to provide compounds of general formula (97), wherein $R_3$ and $R_8$ may or may not be the same.

Ketones of general formula (95) can also be alkylated with alkylating agents such as 1,2-dibromoethane, 1,3 diiodopropane, or the like to provide ketones of general formula (97) wherein $R_3$ and $R_8$ together with the benzylic carbon atom to which they are attached form a 3-, 4-, 5-, or 6-membered carbocyclic ring.

Ketones of general formula (97) can be brominated to provide compounds of general formula (98). Compounds of general formula (98) can be processed as described in Scheme 16 to provide compounds of general formula (99).

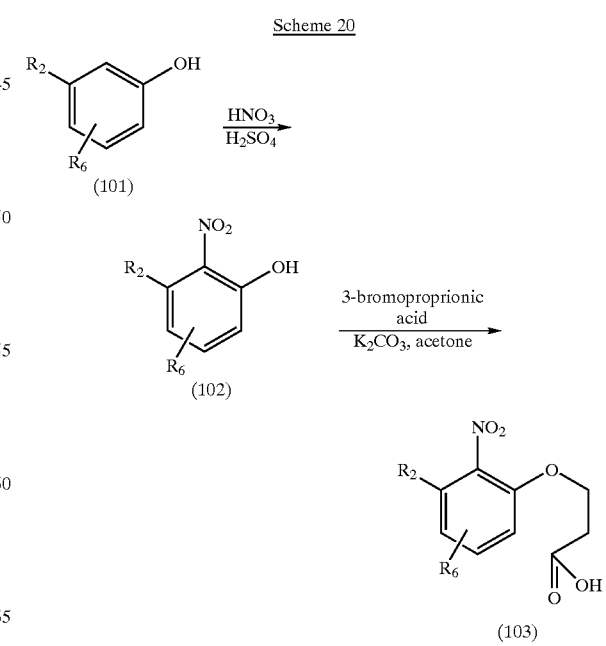

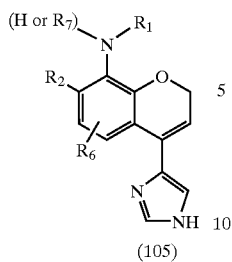
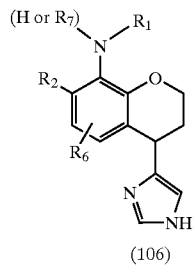
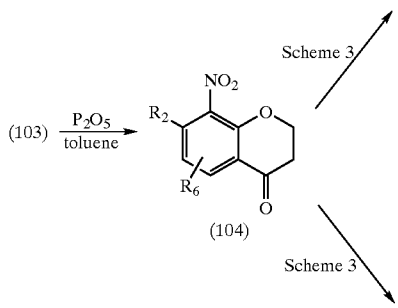

Compounds of general formula (105) and (106), wherein $R_1$, $R_2$, $R_6$, and $R_7$ are as defined in formula 1, can be prepared as illustrated in Scheme 20. Substituted phenols of general formula (101) can be nitrated and then treated with 3-bromopropionic acid to provide acids of general formula (103). Acids of general formula (103) can be cyclized with phosphorous pentoxide to provide chromanones of general formula (104). Chromanones (104) can be processed as in previous Schemes, in particular Scheme 1, Scheme 2, or Scheme 3, to provide chromenes of general formula (105) and chromans of general formula (106).

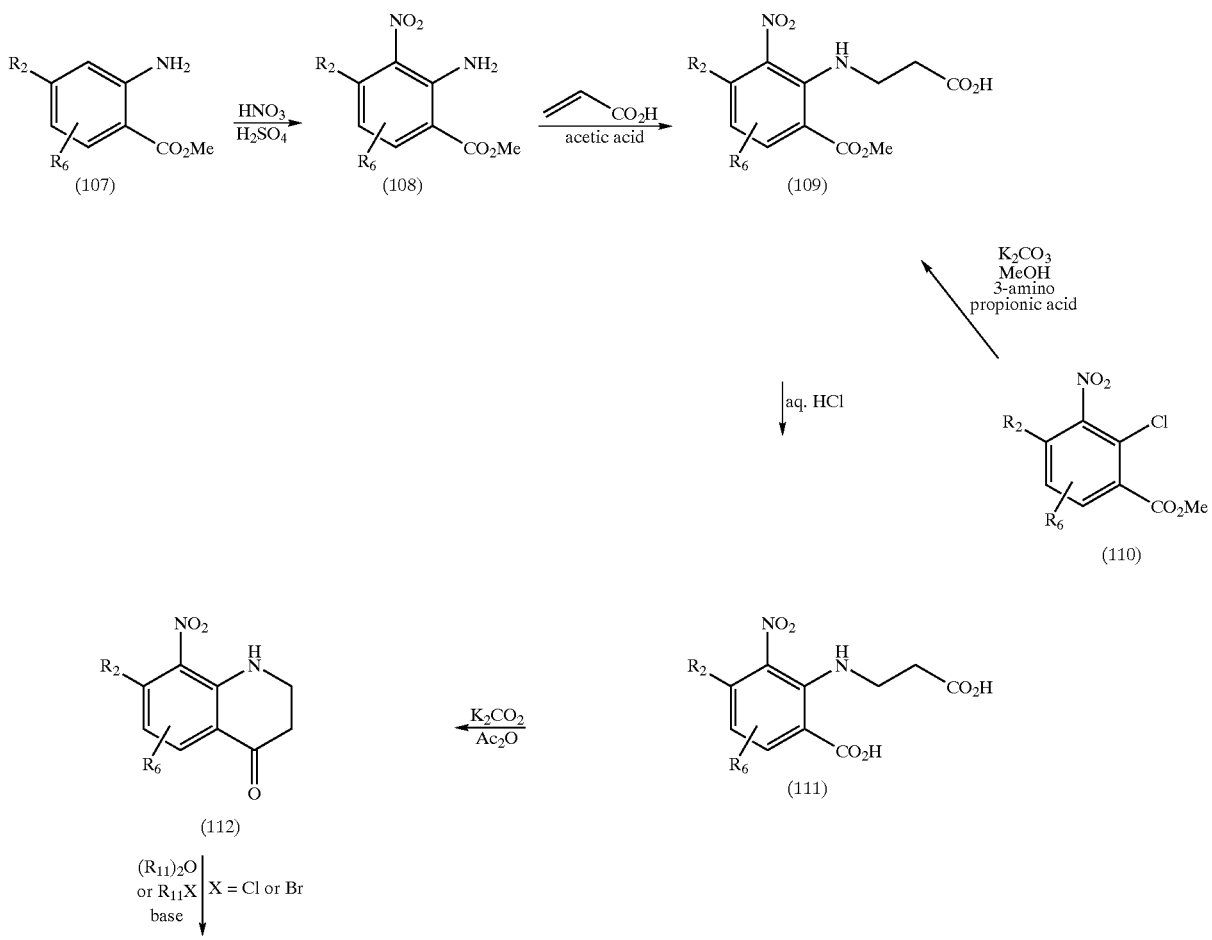

Scheme 21

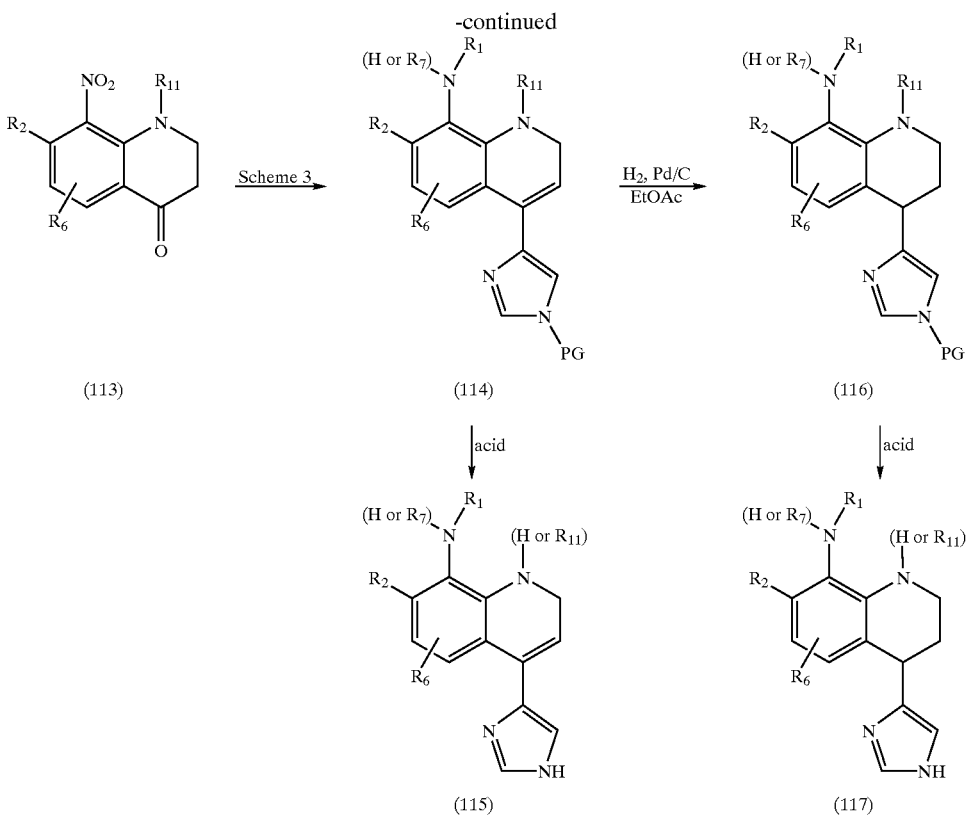

Dihydroquinolines of general formula (115) and tetrahydroquinolines of general formula (117), wherein $R_1$, $R_2$, $R_6$, $R_7$, and $R_{11}$ are as defined in formula I, can be prepared as illustrated in Scheme 21. Nitration of anilines of general formula (107) using a nitrating agent such as nitric acid provides nitroanilines of general formula (108). Anilines of general formula (108) can be alkylated with acrylic acid in a solvent such as acetic acid to provide propionic acids of general formula (109). Propionic acids of general formula (109) can also be prepared from substituted nitrohalides of general formula (110). Nitrohalides of general formula (110) can be treated with 3-aminopropionic acid in the presence of a base such as potassium carbonate to provide propoionic acids of general formula (109). Compounds of general formula (109) can be saponified under aqueous acidic conditions to provide diacids of general formula (111) which can be converted to 8-nitro-2,3-dihydro-1H-quinolin-4-ones of general formula (112) using potassium acetate and acetic anhydride as reported in (Bolotina, L. A Chem.Het.Compd. (Engl.Transl.), (1982), 18, 671–673. Nitro quinolinones (112) can be treated with acylating or sulfonylating agents (such as sulfonyl chlorides, anhydrides, acid chlorides, or the like) using a mild base (such as pyridine) in a solvent (such as dichloromethane) to provide N-acylated nitro quinolinones of general formula (113) or N-sulfonated nitro quinolinones of general formula (113). Alternatively, nitro quinolinones of general formula (112) also can be alkylated with alkyl halides such as methyl iodide, ethyl iodide, benzyl bromide, or the like in the presence of a base such as potassium carbonate to provide or N-alkylated nitro quinolinones of general formula (113). Nitro quinolinones of general formula (113) can be processed as described in previous Schemes, in particular Scheme 3, to provide compounds of the present invention of general formula (115) and (117).

Scheme 22

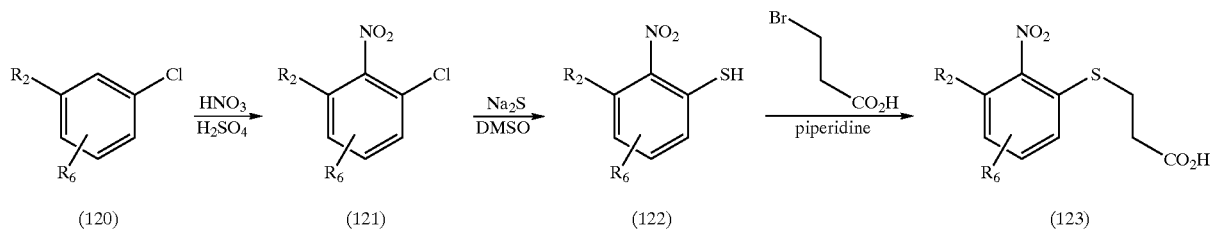

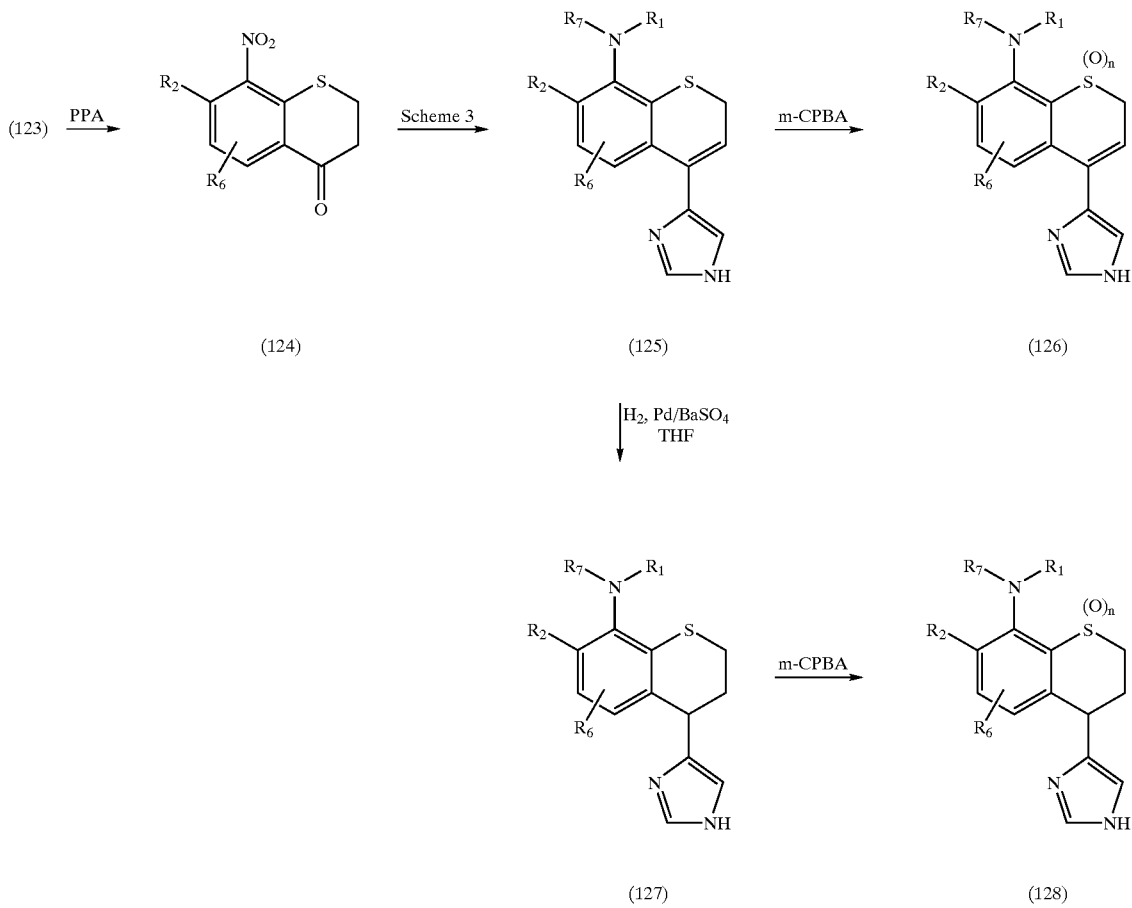

Compounds of general formula (125), (126), (127), and (128), wherein $R_1$, $R_2$, $R_6$, and $R_7$ are as defined in formula I and n is 1–2, can be prepared as illustrated in Scheme 22. Substituted chlorobenzenes of general formula (120) can be nitrated at the ortho position to provide ortho-chloronitrobenzenes of general formula (121). Ortho-chloronitrobenzenes of general formula (121) can be treated with sodium sulfide in dimethylsulfoxide to provide nitrothiophenols of general formula (122). Nitrothiophenols of general formula (122) can be treated with 3-bromoproprionic acid in the presence of piperidine to provide acids of general formula (123). Acids of general formula (123) can be cyclized to 8-nitro-2,3-dihydro-4H-thiochroman-4-ones of general formula (124) as described in (Schaefer, T. Can.J.Chem. (1987), 65, 908–914). Thiochroman-4-ones (124) can be processed as described in previous Schemes, in particular Scheme 3, to provide thiochromenes of general formula (125) which can be selectively oxidized to the sufoxides or sulfones of general fomula (126) using one or two equivalents respectively of an oxidant such as 3-chloroperoxybenzoic acid (m-CPBA) or the like. Thiochromenes of general formula (125) can be treated with a reducing agent such as hydrazine in a solvent such as methanol or catalytic hydrogenation using palladium in the presence of barium sulfate to provide thiochromans of general formula (127) which can be selectively oxidized to the sufoxides or sulfones of general formula (128) using one or two equivalents respectively of an oxidant such as 3-chloroperoxybenzoic acid (m-CPBA) or the like.

Scheme 23

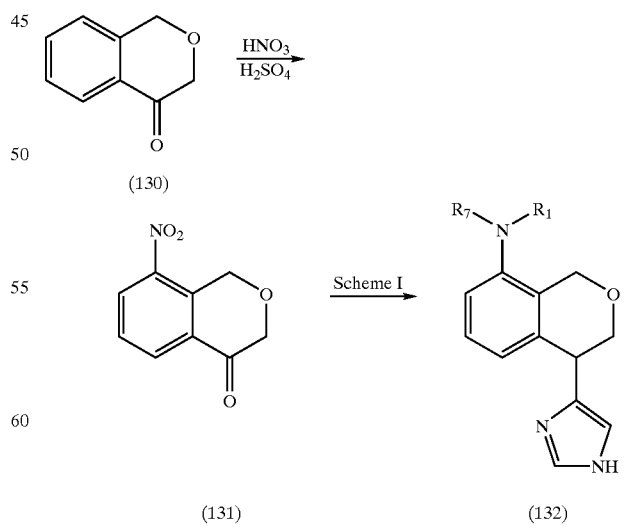

Isochromans of general formula (132), wherein $R_1$ and $R_7$ are as defined in formula I, can be prepared as illustrated in Scheme 23. 1H-Isochroman-4(3H)-one can be nitrated as described in (Anzalone, L. J.Org.Chem. 1985, 50, 2128–2133) to provide 8-nitro-1H-isochroman-4(3H)-one which can be processed as described in previous Schemes, in particular Scheme 1 and Scheme 2, to provide isochromans of general formula (132).

Compounds of general formula (137) can be reduced with reducing agents such as sodium cyanoborohydride in methanol to provide tetrahydroisoquinolines of general formula (138). Removal of the para-methoxybenzyl (PMB) protecting group of (138) with ceric ammonium nitrate provides

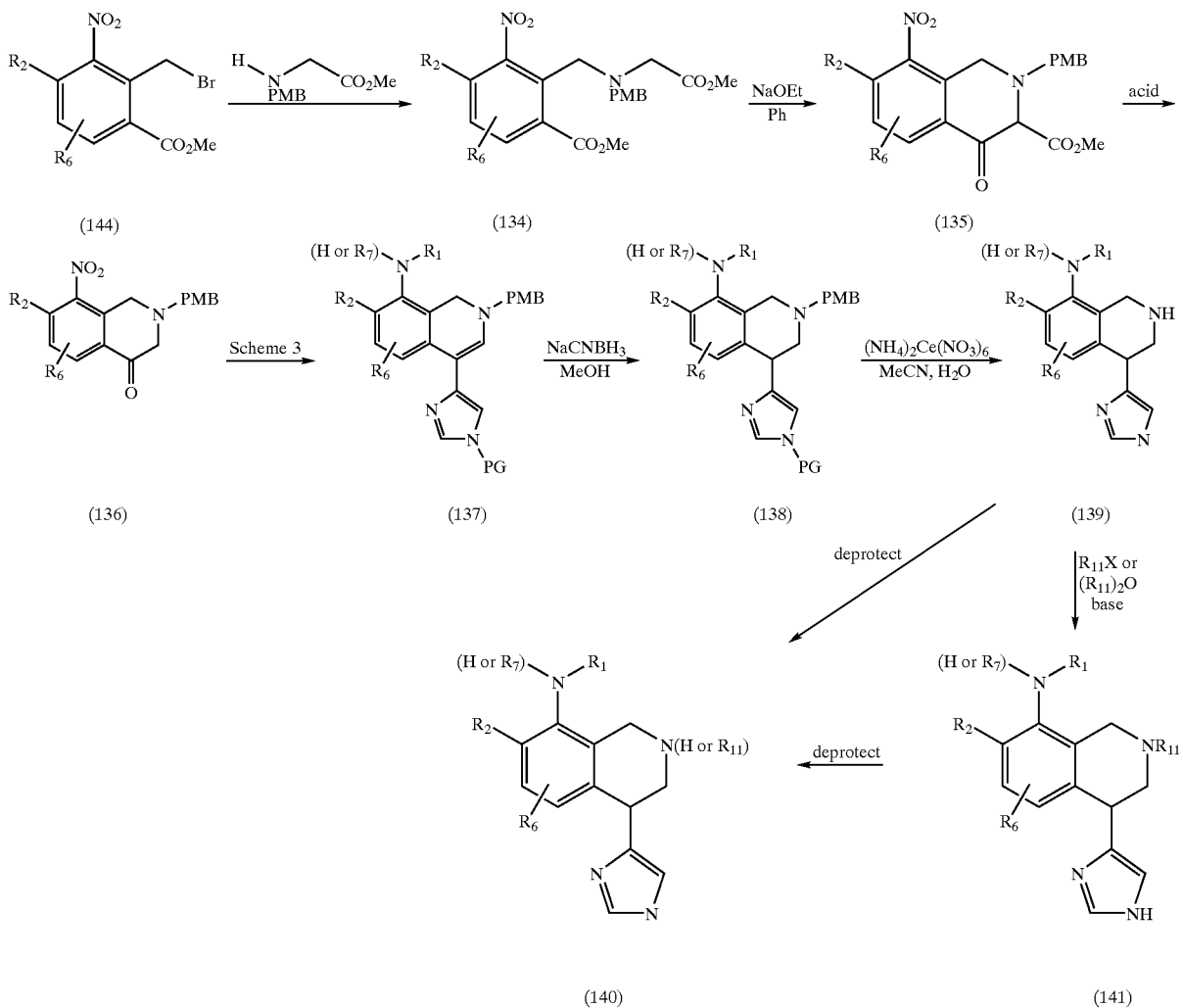

secondary amines of general formula (139). Compounds of general formula (139) can be treated with electrophiles in the presence of a base such as pyridine or potassium carbonate to provide N-substituted tetrahydroisoquinolines of general formula (140).

Tetrahydroisoquinolines of general formula (140), wherein $R_1$, $R_7$ and $R_{11}$ are as defined in formula I, can be prepared as illustrated in Scheme 24. Nitrobenzylbromides of general formula (144), prepared as described in Scheme 25, can be treated with N-(4-methoxybenzyl)glycine methyl ester as described in (Weygand, F. Chem.Ber. 1968, 101, 3623–3641) in the presence of a base such as triethylamine to provide diesters of general formula (134). Diesters (134) can be treated with a base such as sodium ethoxide in a solvent such as benzene to provide ketoesters of general formula (135) which can be decarboxylated under acidic conditions to provide isoquinolinones of general formula (136). Isoquinolinones of general formula (136) can be processed as described in previous Schemes, in particular Scheme 3, to provide compounds of general formula (137).

Scheme 25

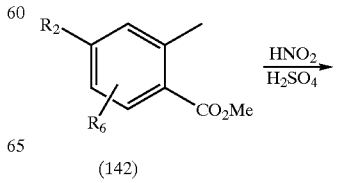

(142)

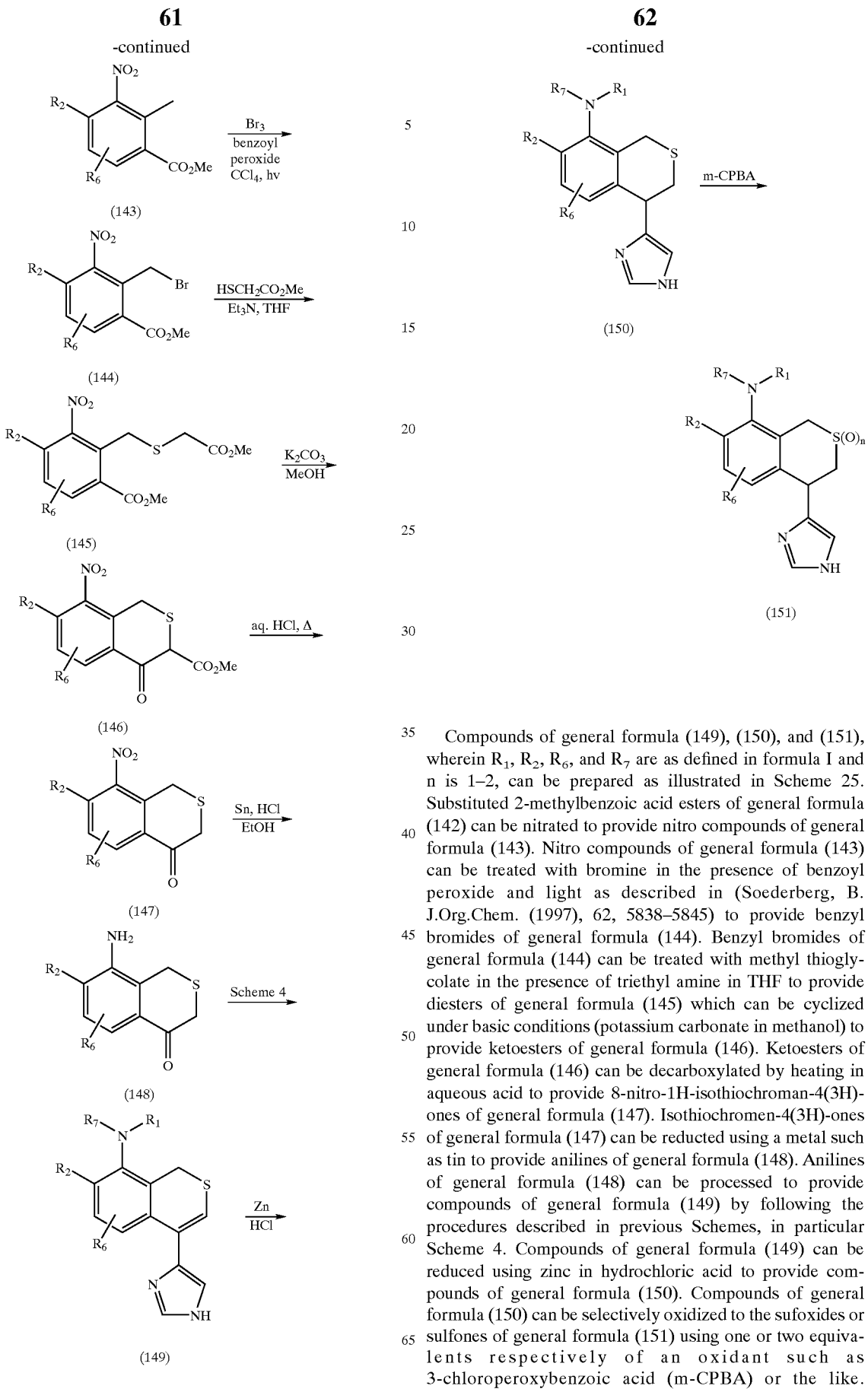

Compounds of general formula (149), (150), and (151), wherein $R_1$, $R_2$, $R_6$, and $R_7$ are as defined in formula I and n is 1–2, can be prepared as illustrated in Scheme 25. Substituted 2-methylbenzoic acid esters of general formula (142) can be nitrated to provide nitro compounds of general formula (143). Nitro compounds of general formula (143) can be treated with bromine in the presence of benzoyl peroxide and light as described in (Soederberg, B. J.Org.Chem. (1997), 62, 5838–5845) to provide benzyl bromides of general formula (144). Benzyl bromides of general formula (144) can be treated with methyl thioglycolate in the presence of triethyl amine in THF to provide diesters of general formula (145) which can be cyclized under basic conditions (potassium carbonate in methanol) to provide ketoesters of general formula (146). Ketoesters of general formula (146) can be decarboxylated by heating in aqueous acid to provide 8-nitro-1H-isothiochroman-4(3H)-ones of general formula (147). Isothiochromen-4(3H)-ones of general formula (147) can be reduced using a metal such as tin to provide anilines of general formula (148). Anilines of general formula (148) can be processed to provide compounds of general formula (149) by following the procedures described in previous Schemes, in particular Scheme 4. Compounds of general formula (149) can be reduced using zinc in hydrochloric acid to provide compounds of general formula (150). Compounds of general formula (150) can be selectively oxidized to the sufoxides or sulfones of general formula (151) using one or two equivalents respectively of an oxidant such as 3-chloroperoxybenzoic acid (m-CPBA) or the like.

Scheme 26

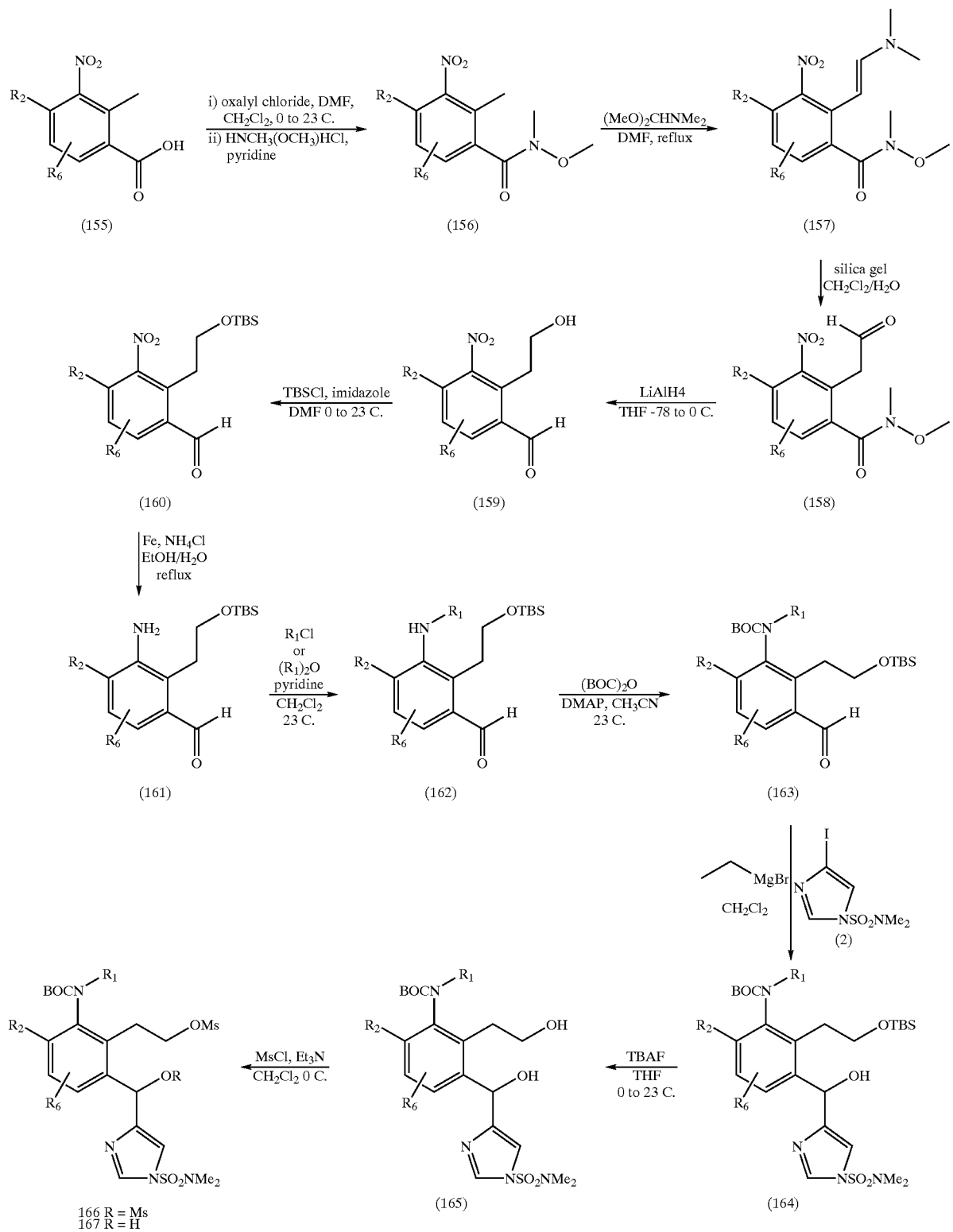

Scheme 26 illustrates the synthesis of compounds of general formula (166) and (167) wherein $R_1$, $R_2$ and $R_6$ are as defined in formula I. 2-Methyl-3-nitrobenzoic acids of general formula (155) can be treated with oxalyl chloride and DMF in methylene chloride starting at 0° C. and warming to 23° C. to form acid chlorides which are immediately reacted in situ with N,O-dimethylhydroxylamine hydrochloride and pyridine to form compounds of general formula (156). Compounds of general formula (156) can be treated with dimethylformamide dimethyl acetal in dimethylformamide at reflux to generate N,N-dimethyl-2-phenylethenamine compounds of general formula (157). Compounds of general formula (157) can be stirred with silica gel in a mixture of methylene chloride and water to provide aldehydes of general formula (158). Aldehydes of general formula (158) can be reduced with lithium aluminum hydride in tetrahydrofuran to provide compounds of general formula (159) on warming from −78° C. to 0° C. Compounds of general formula (159) can be combined with tert-butyldimethylsilyl chloride and imidazole in DMF at 0° C. and warmed to 23° C. to form silylethers of general formula (160). Silylethers of general formula (160) can be reduced with Fe and $NH_4Cl$ in a solution of refluxing ethanol and water to provide anilines of general formula (161). Anilines of general formula (161) can be processed as described in previous Schemes, in particular Scheme 1 and Scheme 2, to provide compounds of general formula (162). Compounds of general formula (162) can be treated with di-tert-butyl dicarbonate and N,N-dimethylaminopyridine in acetonitrile at 23° C. to provide compounds of general formula (163). Compounds of general formula (163) can be treated at 23° C. with a pre-mixed solution of (2) and ethyl magnesium bromide in methylene chloride to provide alcohols of general formula (164). Alcohols of general formula (164) can be treated with tetrabutylammonium fluoride in tetrahydrofuran between 0° C. and 23° C. to deprotect the tert-butyldimethylsilyl ether and form diols of general formula (165). Diols of general formula (165) can be treated with 2 equivalents of methanesulfonyl chloride and triethylamine in methylene chloride at 0° C. to provide compounds of general formula (166). ). Diols of general formula (165) can also be treated with 1 equivalent of methanesulfonyl chloride and triethylamine in methylene chloride at 0° C. to provide compounds of general formula (167).

Scheme 27

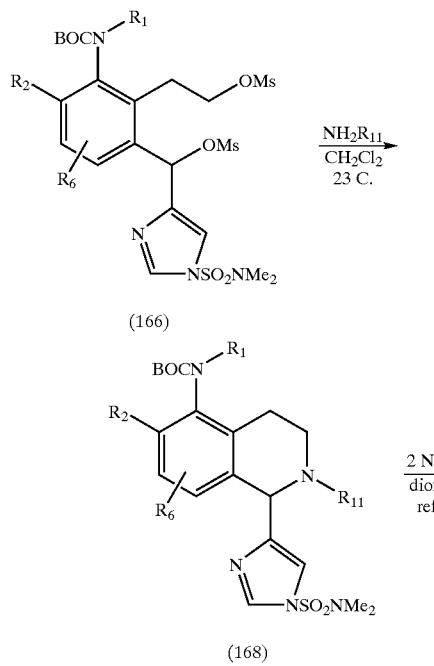

-continued

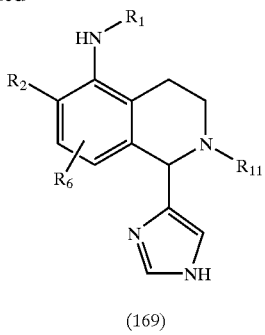

Isoquinolines of general formula (169), wherein $R_1$, $R_2$, $R_6$, and $R_{11}$ are as defined in formula I, can be prepared as illustrated in scheme 27. Compounds of general formula (166), prepared as illustrated in Scheme 26, can be treated with various primary amines in methylene chloride at ambient temperature to provide isoquinolines of general formula (168). Isoquinolines of general formula (168) can be treated with 2N HCl and dioxane at reflux to remove both the BOC and sulfamoyl protecting groups to provide compounds of general formula (169).

Scheme 28

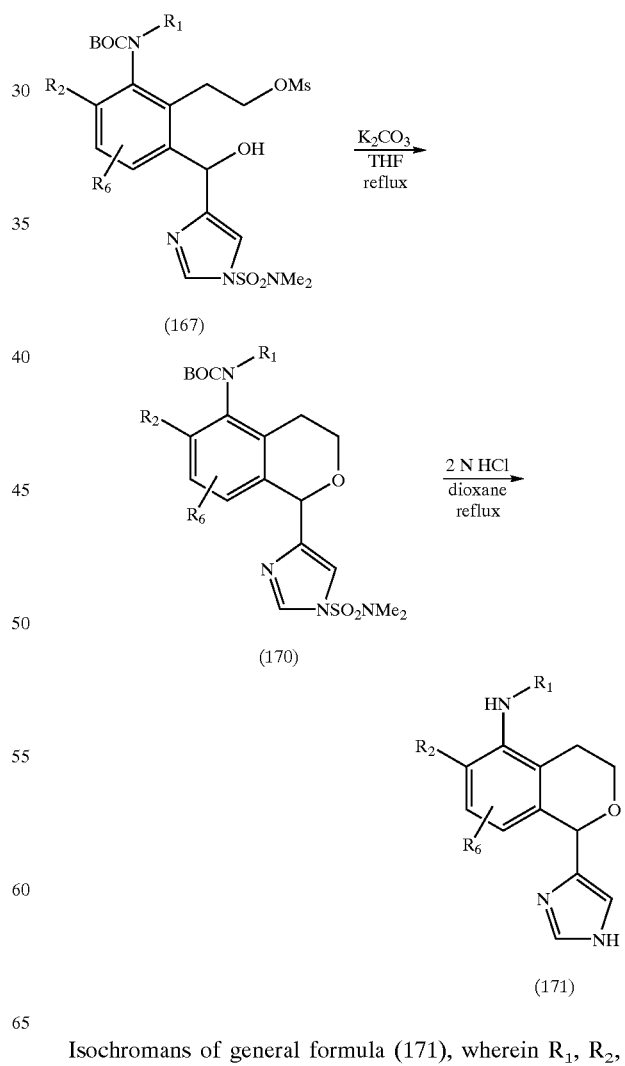

Isochromans of general formula (171), wherein $R_1$, $R_2$, and $R_6$ are as defined in formula I, can be prepared as illustrated in scheme 28. Compounds of general formula (167), prepared as illustrated in Scheme 26, can be treated with K$_2$CO$_3$ in tetrahydrofuran at reflux to provide compounds of general formula (170). Compounds of general formula (170) can be treated with 2N HCl and dioxane at reflux to remove both the BOC and sulfamoyl protecting groups to generate isochromans of general formula (171).

formula (173). Isothiochromans of general formula (173) can be treated with 2N HCl and dioxane at reflux to remove both the BOC and sulfamoyl protecting groups to provide isothiochromans of general formula (174).

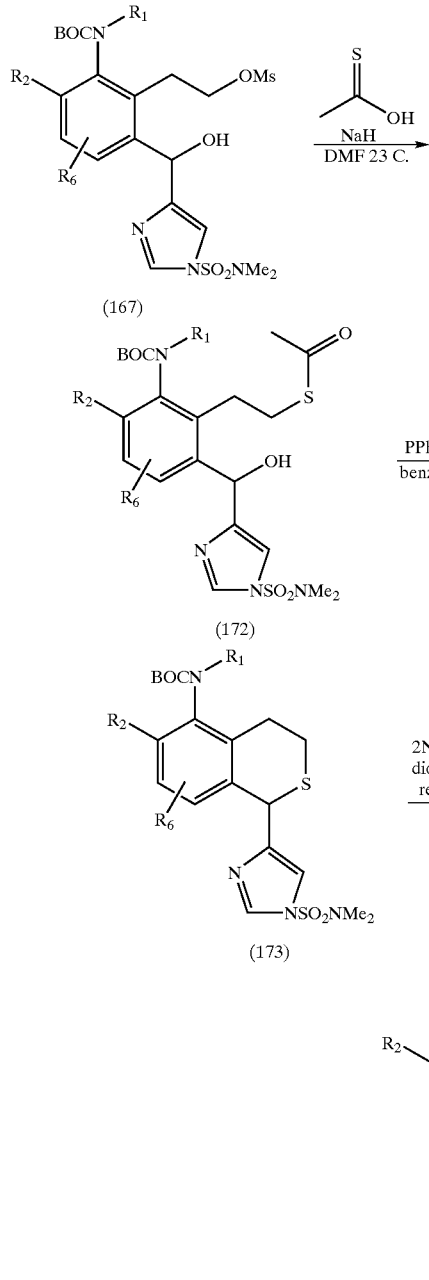

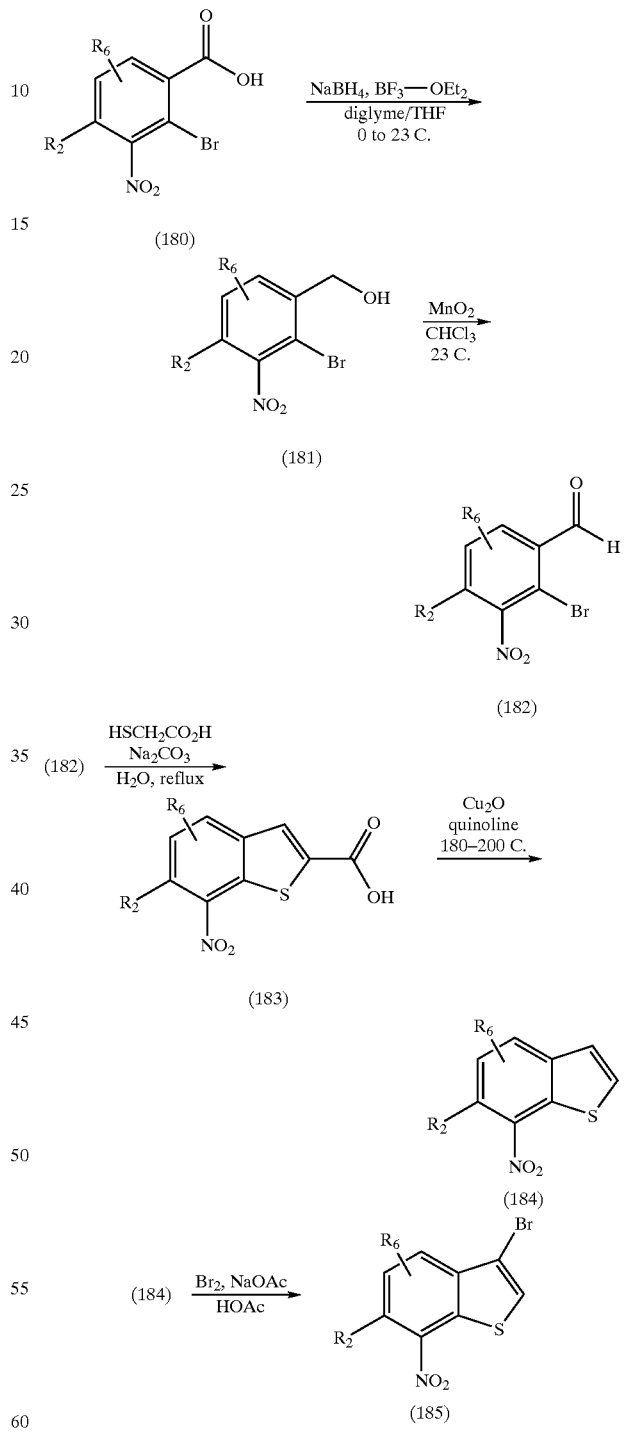

Isothiochromans of general formula (174), wherein R$_1$, R$_2$, and R$_6$ are as defined in formula I, can be prepared as illustrated in Scheme 29. Compounds of general formula (167), prepared as illustrated in Scheme 26, can be treated with thioacetic acid and sodium hydride in DMF at ambient temperature to form compounds of general formula (172). Compounds of general formula (172) can be treated with diethyl azodicarboxylate and triphenylphosphine in benzene at ambient temperature to form isothiochromans of general Benzothiophenes of general formula (185), wherein R$_2$ and R$_6$ are as defined in formula I, can be prepared as illustrated in Scheme 30. Nitrobenzoic acids of general formula (180) can be treated with sodium borohydride and boron trifluoride etherate in diglyme and THF between 0° C. and 23° C. to provide benzylic alcohols of general formula (181). Benzylic alcohols of general formula (181) can be treated with manganese dioxide in chloroform at 23° C. to provide aldehydes of general formula (182). Aldehydes of general formula (182) can be treated with mercaptoacetic acid in aqueous sodium carbonate at reflux to provide 7-nitrobenzothiophene-2-carboxylic acids of general formula (183) which can be decarboxylated with cuprous oxide in quinoline between 180° C. and 200° C. to provide 7-nitrobenzothiophenes of general formula (184). 7-Nitrobenzothiophenes of general formula (184) can be treated with bromine and anhydrous sodium acetate in acetic acid to form 3-bromo-7-nitrobenzothiophenes of general formula (185).

Scheme 31. Nitrobenzaldehydes of general formula (186) can be treated with diethyl bromomalonate, potassium carbonate, and tetrabutylammonium bromide in toluene at reflux to provide nitrobenzofurans of general formula (187). Nitrobenzofurans of general formula (187) can be hydrozyled with potassium hydroxide in water to provide acids of general formula (188). Acids of general formula (188) can be decarboxylated with cuprous oxide in quinoline between 180° C. and 200° C. to form the 7-nitrobenzofurans of general formula (189). 7-Nitrobenzofurans of general formula (189) can be dibrominated by reaction with bromine in acetic acid at reflux to provide dibromobenzofurans of general formula (190). Dibromobenzofurans of general formula (190) can be treated with potassium ethoxide in ethanol to provide 3-bromo-7-nitrobenzofurans of general formula (191).

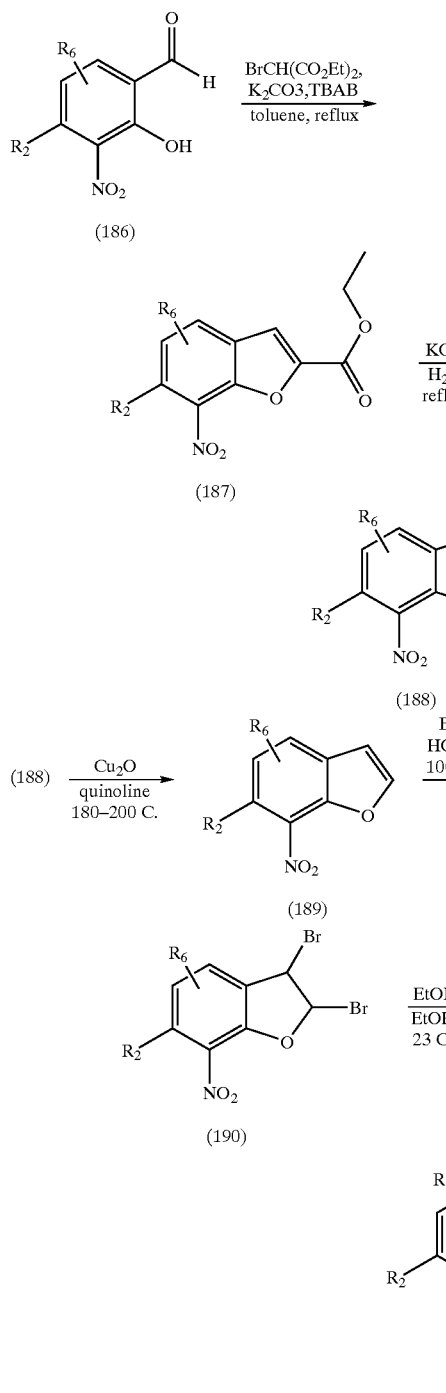

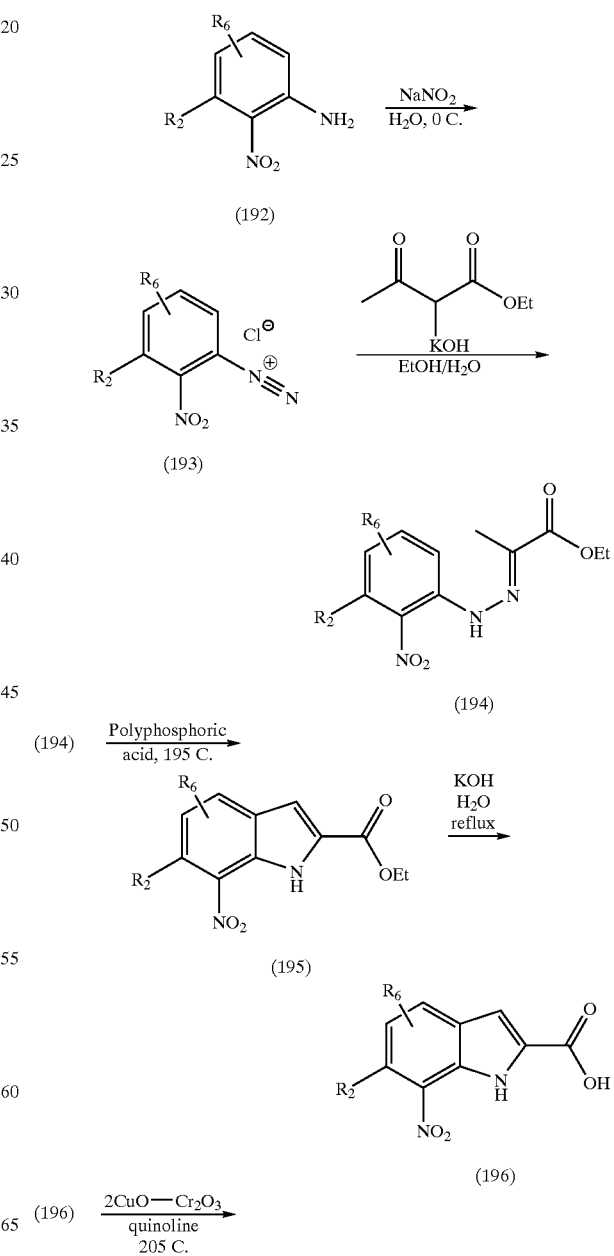

Benzofurans of general fomula (191), wherein $R_2$ and $R_6$ are as defined in formula I, can be prepared as illustrated in

71

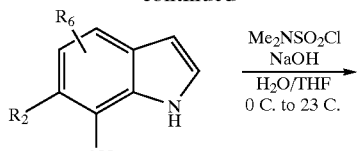

(197)

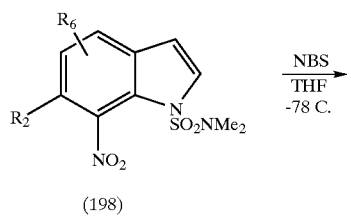

(198)

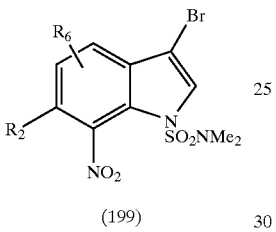

(199)

3-Bromo-7-nitroindoles of general fomula (199), wherein $R_2$ band $R_6$ are as defined in formula I, can be prepared as illustrated in Scheme 32. 2-Nitroanilines of general formula (192) can be treated with sodium nitrate in water at 0° C. to provide compounds of general formula (193). Compounds of general formula (193) can be treated with 2-methyl-3-oxo-butyric acid ethyl ester and potassium hydroxide in ethanol and water to provide hydrazones of general formula (194). Hydrazones of general formula (194) can be heated in polyphosphoric acid at 195° C. to facilitate ring closure to provide indoles of general formula (195). Indoles of general formula (195) can be treated with potassium hydroxide and water at reflux to form acids of general formula (196). Acids of general formula (196) can be decarboxylated with copper chromite in quinoline at 205° C. to provide 7-nitroindoles of general formula (197). 7-Nitroindoles of general formula (197) can be treated with N,N-dimethylsulfamoyl chloride and sodium hydroxide in THF and water between 0° C. and 23° C. to provide N-protected indoles of general formula (198). N-Protected indoles of general formula (198) can be treated with N-bromosuccinimide in THF at -78° C. to provide 3-bromo-7-nitroindoles of general fomula (199).

Scheme 33

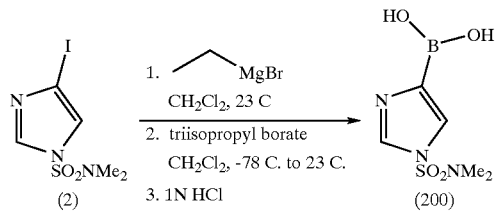

1-[(dimethylamino)sulfonyl]-1H-imidazol-4-ylboronic acid can be prepared as illustrated in Scheme 33. 4-Iodo-N,N-dimethyl-1H-imidazole-1-sulfonamide (2) can be treated successively with ethyl magnesium bromide in methylene chloride at 23° C.; triisopropyl borate in methylene chloride between -78° C. and 23° C.; and 1N HCl in water to provide boronic acid (200).

Scheme 34

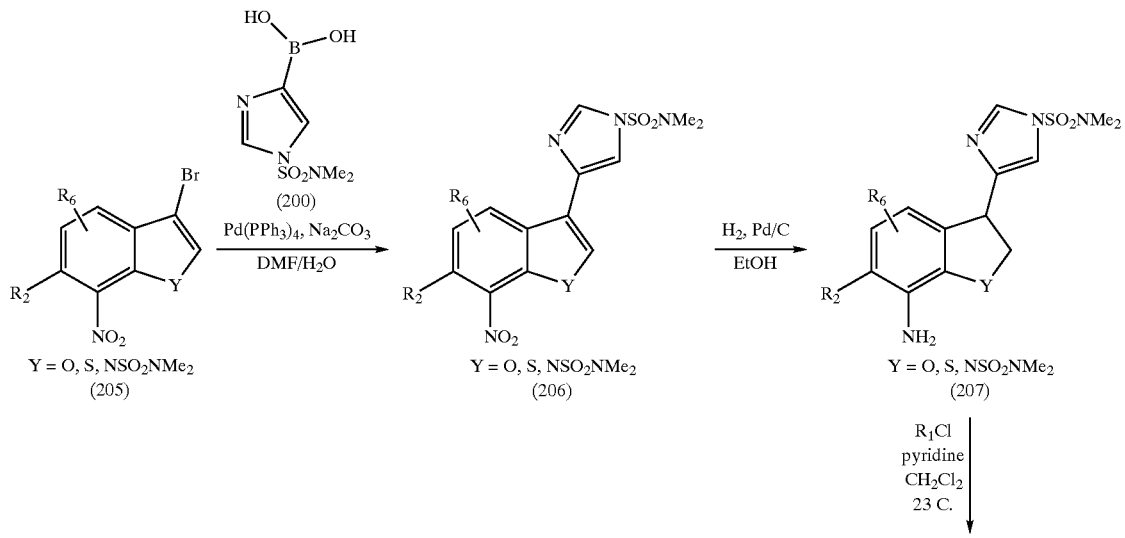

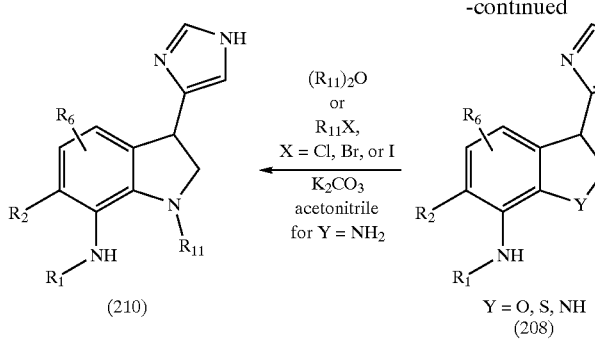
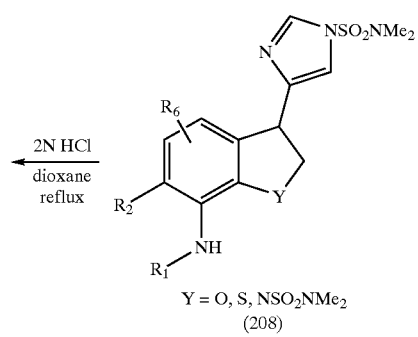

Compounds of general formula (209) and (210), wherein $R_1$, $R_2$, $R_4$, and $R_{11}$ are as defined in formula I and Y is selected from O, S, and NH, can be prepared as illustrated in Scheme 34. Compounds of general formula (205), wherein Y is selected from O, S, and $NSO_2NMe_2$ prepared as described in Schemes 30–32, can be treated with boronic acid (200) (prepared as described in Scheme 33), palladium tetrakistriphenylphosphine, and sodium carbonate in water and DMF to provide nitroimidazoles of general formula (206), wherein Y is selected from O, S, and $NSO_2NMe_2$. Nitroimidazoles of general formula (206), wherein Y is selected from O, S, and $NSO_2NMe_2$, can be reduced with hydrogen and Pd/C in a solution of ethanol to provide anilines of general formula (207), wherein Y is selected from O, S, and $NSO_2NMe_2$. Anilines of general formula (207) wherein Y is selected from O, S, and $NSO_2NMe_2$, can be processed as described in previous Schemes, in particular Scheme 1 and Scheme 2, to provide compounds of general formula (208), wherein Y is selected from O, S, and $NSO_2NMe_2$. Compounds of general formula (208), wherein Y is selected from O, S, and $NSO_2NMe_2$, can be treated with 2N HCl and dioxane at reflux to remove both the BOC and sulfamoyl protecting groups to provide compounds of general formula (209), wherein Y is selected from O, S, and NH. Indoles of general formula (209), wherein Y is NH, can be treated with acylating agents, sulfonating agents, or alkylating agents to provide indoles of general formula (210).

Scheme 35

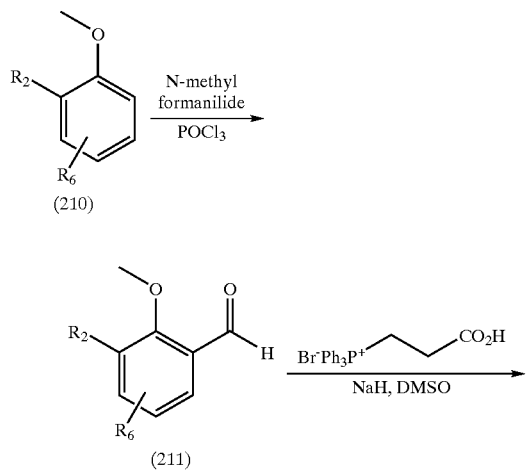

5-Methoxy tetralones of general formula (214), wherein $R_2$ and $R_6$ are as defined in formula I, can be prepared as illustrated in Scheme 40. Anisoles of general formula (210) can be treated with N-methylformanilide in phosphorous oxychloride as described in (Hunsberger, J.Amer.Chem.Soc. (1955), 77, 2466,2474) to provide aldehydes of general formula (211). Alternatively, anisoles of general formula (210) can be deprotonated with butyllithium in a solvent such as ether and the resulting anion quenched with a formamide such as dimethylformamide as described in (Murray, P. J. Bioorg.Med.Chem.Lett (1996), 6, 403–408) to provide aldehydes of general formula (211) Aldehydes of general formula (211) can be treated with (2-carboxyethyl)triphenylphosphonium bromide as described in (Abdukakharov, V. S. Chem.Nat.Compd.(Engl.Transl.) (1990), 4, 486–487) in the presence of sodium hydride in a solvent such as dimethylsulfoxide to provide acids of general formula (212). Acids of general formula (212) can be hydrogenated using a catalyst such as palladium in a solvent such as ethyl acetate to provide butyric acids of general formula (213). Butyric acids of general formula (213) can be cyclizated to provide 5-methoxytetralones of general formula (214) under acidic conditions (such as heating in polyphosphoric acid for example). 5-Methoxytetralones of general formula (214) can be processed as in Scheme 5 to provide compounds of the present invention.

Scheme 36

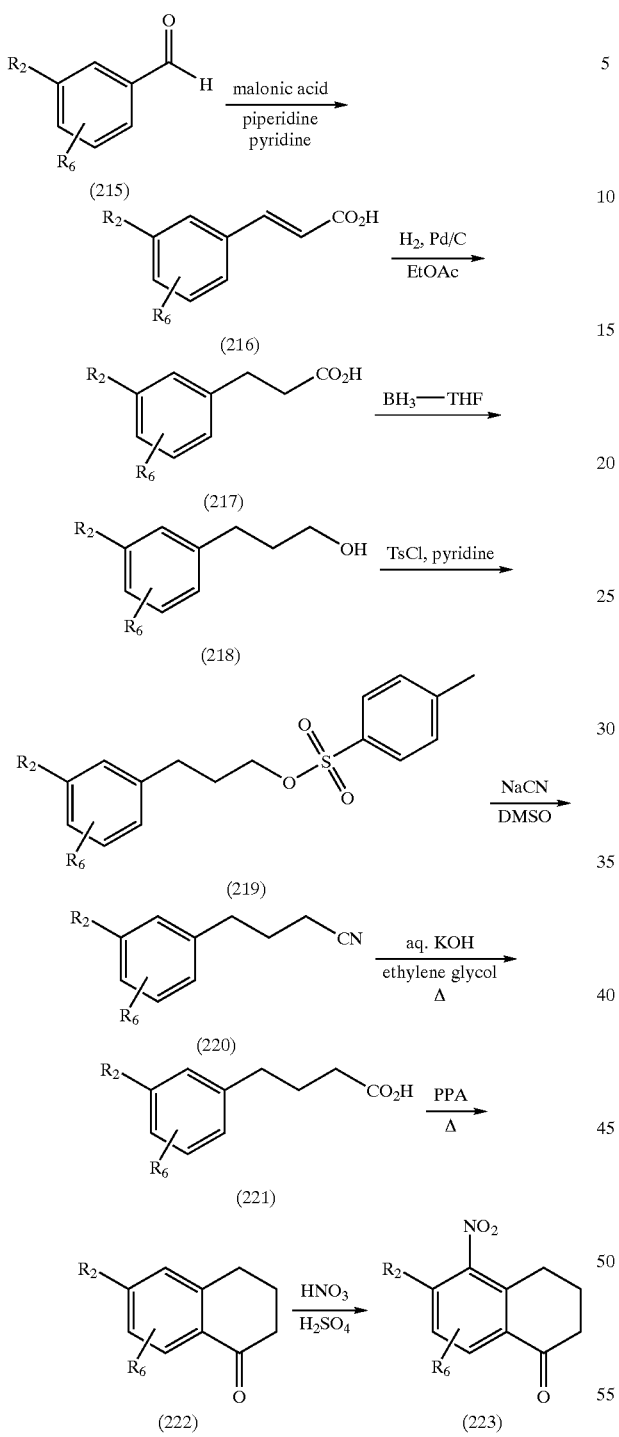

tetrahydrofuran complex in a solvent such as THF. Alcohols of general formula (218) can be treated with para-toluenesulfonyl chloride to provide tosylates of general formula (219) which can be converted to nitriles of general formula (220) using sodium cyanide (for example) in a solvent such as dimethyl sulfoxide. Nitriles of general formula (220) can be converted to the corresponding butyric acids of general formula (221) under basic (heating in aqueous potassium hydroxide with ethylene glycol as a solvent for example) or acidic (heating in aqueous sulfuric acid with acetic acid as a solvent for example) conditions. Butyric acids of general formula (221) can be cyclized tetralones of general formula (222) by heating in polyphosphoric acid for example. The tetralones of general formula (222) can be nitrated using nitric acid in sulfuric acid for example to provide nitrotetralones of general formula (223). Nitrotetralones of general formula (223) can be processed as described in previous Schemes, in particular Schemes 1, 2 or 4, to provide compounds of the present invention.

Scheme 37

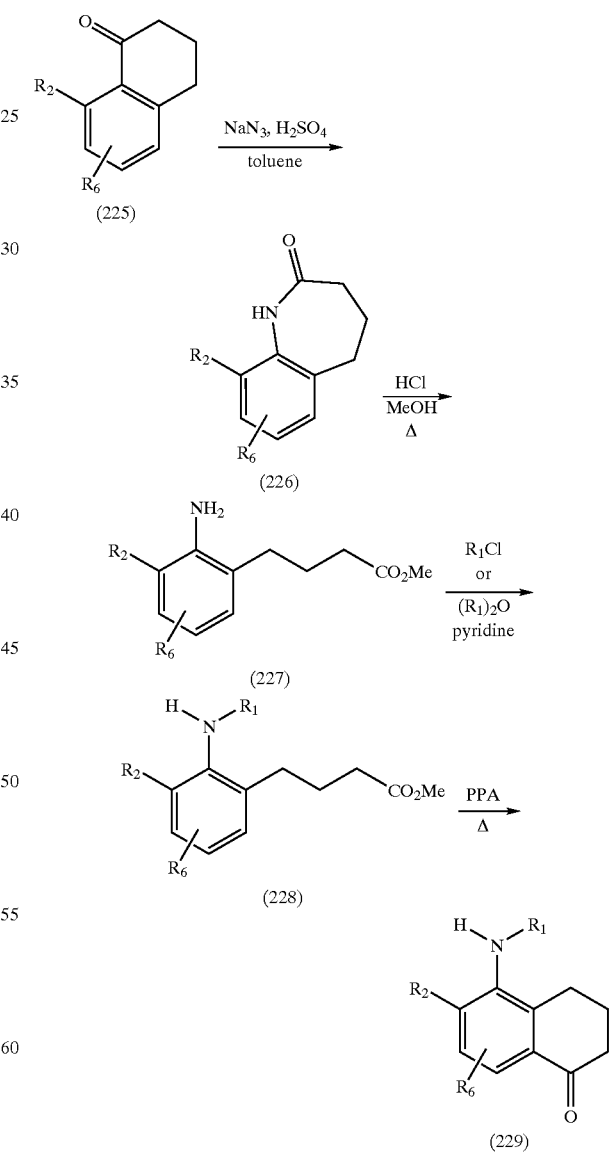

Nitrotetralones of general formula (223), wherein $R_2$ and $R_6$ are as defined in formula I, can be prepared as illustrated in Scheme 36. Substituted aldehydes of general formula (215) can be treated with malonic acid in the presence of a base such as piperidine in a solvent such as pyridine to provide unsaturated propionic acids of general formula (216). Unsaturated propionic acids of general formula (216) can be hydrogenated using a catalyst such as palladium in a solvent such as ethyl acetate to provide saturated acids of general formula (217). Acids of general formula (217) can be reduced to alcohols of general formula (218) with borane- Tetralones of general formula (229), wherein $R_1$, $R_2$, and $R_6$, are as defined in formula I, can be prepared as illustrated in Scheme 37. Substituted tetralones of general formula (225), available from Scheme 36, can be treated with sodium azide in the presence of sulfuric acid in a solvent such as toluene to provide lactams of general formula (226). Lactams of general formula (226) can be treated with hydrochloric acid in methanol with heat to provide anilines of general formula (227). Anilines of general formula (227) can be treated with acylating or sulfonating agents in a solvent such pyridine to provide esters of general formula (228). Esters of general formula (228) can be cyclized to tetralones of general formula (229) by heating in an acid such as polyphosphoric acid. Tetralones of general formula (229) can be processed as described in previous Schemes, in particular Schemes 4 and 12, to provide compounds of the present invention.

Scheme 38

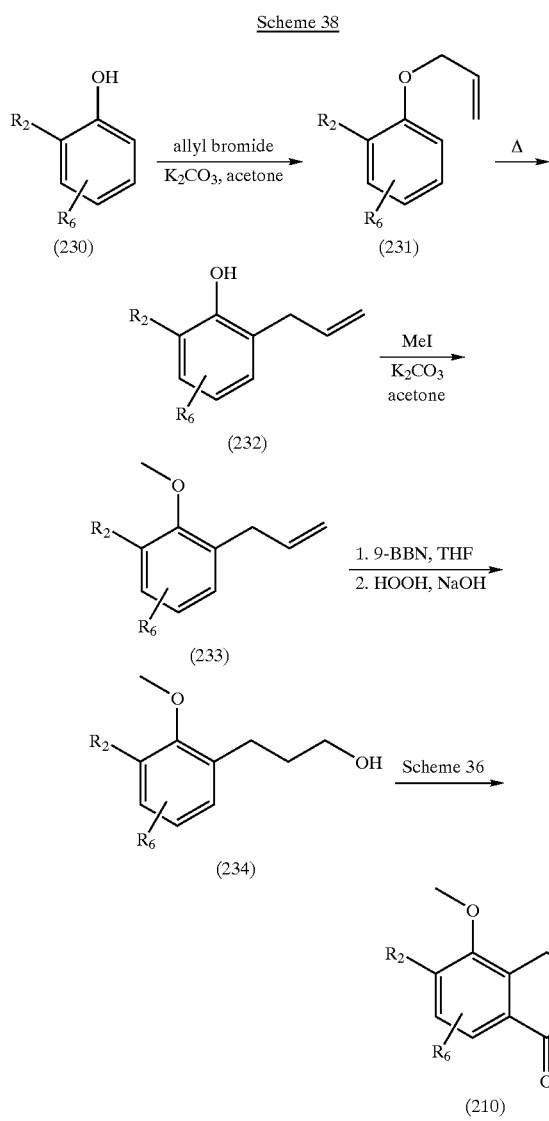

An alternate method for preparing methoxy tetralones of general formula (210), wherein $R_2$ and $R_6$ are defined as in formula I, is illustrated in scheme 38. Phenols of general formula (230) can be treated with allyl bromide in the presence of a base such as potassium carbonate in a solvent such as acetone to provide allylic ethers of general formula (231). Claisen rearrangement of ethers of general formula (231) via heating with or without a solvent such as N,N-diethylaniline provides phenols of general formula (232). Phenols of general formula (232) can be methylated with methyl iodide or the like using a base such as potassium carbonate in a solvent such as acetone to provide anisoles of general formula (233). Anisoles of general formula (233) can be treated with a hydroborating agent such as 9-borabicyclo[3.3.1]nonane or the like in a solvent such as THF fllowed by oxidation with hydrogen peroxide in aqueous sodium hydroxide or the like to provide alcohols of general formula (234). Alcohols of general formula (234) can be processed to tetralones of general formula (210) using the procedures described in Scheme 36. Tetralones of general formula (210) can be processed as described in previous Schemes, in particular Scheme 5, to provide compounds of the present invention.

EXAMPLE 1

N-[5-(1H-imidazol-4-yl)-2-methoxy-5,6,7,8-tetrahydro-1-naphthalenyl]methanesulfonamide, hydrochloride

EXAMPLE 1A 4-(1-hydroxy-6-methoxy-5-nitro-1,2,3,4-tetrahydro-1-naphthalenyl)-N,N-dimethyl-1H-imidazole-1-sulfonamide A solution of 4-iodo-N,N-dimethyl-1H-imidazole-1-sulfonamide (3.0 g, 10 mmol) (R. M. Turner, J. Org. Chem. (1991), 56, 5739–5740) in dichloromethane (40 mL) was treated with ethyl magnesium bromide (3.0M in diethyl ether, 3.3 mL) over 5 minutes, stirred for 30 minutes, treated with 6-methoxy-5-nitro-1-tetralone (2.6 g, 11.8 mmol), stirred for 16 hours, treated with ammonium chloride solution and extracted with dichloromethane. The extract was dried (MgSO$_4$), filtered and concentrated to provide the desired compound.

MS (DCI/NH$_3$) m/z 397 (M+H)$^+$.

EXAMPLE 1B 4-(6-methoxy-5-nitro-3,4-dihydro-1-naphthalenyl)-1H-imidazole

A suspension of Example 1A (1.1 g, 2.2 mmol) in 1M HCl (30 mL) was heated to 90° C. for 16 hours, cooled to ambient temperature, treated with Na$_2$CO$_3$ solution and extracted with 5:1 dichloromethane/ethanol. The extract was dried (MgSO$_4$), filtered, and concentrated. Purification of the residue on silica gel with 2% ethanol/ammonia-saturated dichloromethane provided the desired compound.

MS (DCI/NH$_3$) m/z 272 (M+H)$^+$.

EXAMPLE 1C 5-(1H-imidazol-4-yl)-2-methoxy-5,6,7,8-tetrahydro-1-naphthalenamine

A mixture of Example 1B and 10% palladium on carbon (60 mg) in methanol (40 mL) was stirred under a hydrogen atmosphere for 16 hours, filtered through Celite,® and concentrated. Purification of the residue on silica gel with 2% ethanol/ammonia-saturated dichloromethane provided the desired compound.

MS (DCI/NH$_3$) m/z 244 (M+H)$^+$.

EXAMPLE 1D tert-butyl 4-(5-amino-6-methoxy-1,2,3,4-tetrahydro-1-naphthalenyl)-1H-imidazole-1-carboxylate A suspension of Example 1C (370 mg, 1.5 mmol) in acetonitrile (25 mL) was treated with di-tert-butyl dicarbonate (370 mg, 1.7 mmol), stirred at ambient temperature for 5 hours, stored at 0° C. for 16 hours, and concentrated. Purification of the residue on silica gel with 3:2 hexanes-:ethyl acetate provided the desired compound.

MS (DCI/NH$_3$) m/z 344 (M+H)$^+$.

EXAMPLE 1E

N-[5-(1H-imidazol-4-yl)-2-methoxy-5,6,7,8-tetrahydro-1-naphthalenyl]methanesulfonamide, hydrochloride A solution of Example 1D (460 mg, 1.34 mmol) in dichloromethane (20 mL) was treated sequentially with pyridine (0.16 mL, 2.0 mmol) and methanesulfonyl chloride (0.12 mL, 1.6 mmol), stirred for 60 hours allowing the solvent to evaporate. Purification of the residue on silica gel with 2% ethanol/ammonia-saturated dichloromethane provided an oil which was converted to the hydrochloride salt to provide the title compound.

mp 209–211° C.;

$^1$H NMR (300 MHz, DMSO-d$_6$) δ 1.65–1.72 (m, 2H), 1.88–2.01 (m, 2H), 1.88 (t, 2H), 3.00 (s, 3H), 3.79 (s, 3H), 4.27 (t, 1H), 6.88 (q, 2H), 7.20 (s, 1H), 8.66 (s, 1H) 9.03 (s, 1H), 14.33 (bs, 2H);

MS (DCI/NH$_3$) m/z 322 (M+H)$^+$;

Anal. calcd for C$_{15}$H$_{20}$N$_3$O$_3$S C, 50.35; H, 5.63; N, 11.74. Found: C, 50.12; H, 5.80; N, 11.65.

EXAMPLE 2

N-[2-hydroxy-5-(1H-imidazol-4-yl)-5,6,7,8-tetrahydro-1-naphthalenyl]methanesulfonamide, hydrochloride A suspension of Example 1E (320 mg, 1.0 mmol) in dichloromethane (100 mL) at 0° C. was treated with BBr$_3$ (1.0M in dichloromethane, 4.0 mL) over 5 minutes, stirred at 0° C. for 2 hours, cooled to −78° C., treated with methanol (10 mL), warmed to ambient temperature, and concentrated. Purification of the residue on silica gel with 20% ethanol/ammonia-saturated dichloromethane provided an oil which was converted to the hydrochloride salt to provide the title compound.

mp 135–137° C. (foam);

$^1$H NMR (300 MHz, DMSO-d$_6$) δ 1.61–1.74 (m, 2H), 1.88–2.00 (m, 2H), 2.86 (t, 2H), 3.03 (s, 3H), 4.21 (t, 1H), 6.69 (d, 1H), 6.75 (d, 1H), 7.18 (d, 1H), 8.58 (s, 1H), 9.05 (d, 1H), 9.85 (s, 1H), 14.38 (bs, 2H);

MS (DCI/NH$_3$) m/z 308 (M+H)$^+$;

Anal. calcd for C$_{14}$H$_{18}$ClN$_3$O$_3$S.CH$_3$CH$_2$OH: C, 49.29; H, 6.20; N, 10.78. Found: C, 48.98; H, 5.73; N, 10.70.

EXAMPLE 3

N-[2-hydroxy-5-(2-methyl-1H-imidazol-4-yl)-5,6,7,8-tetrahydro-1-naphthalenyl]methanesulfonamide, hydrochloride

EXAMPLE 3A 4-(6-methoxy-5-nitro-3,4-dihydro-1-naplhthalenyl)-N,N-dimethyl-1H-imidazole-1-sulfonamide A solution of 4-iodo-N,N-dimethyl-1H-imidazole-1-sulfonamide (4.8 g, 16 mmol) in dichloromethane (65 mL) was treated with ethyl magnesium bromide (3.0M in diethyl ether, 5.4 mL) over 5 minutes, stirred for 30 minutes, treated with 6-methoxy-5-nitro-1-tetralone (3.9 g, 18 mmol), stirred for 16 hours, and concentrated. The residue was treated with 1M HCl (100 mL), heated to 100° C. for 1 hour, cooled to ambient temperature and filtered. The filtrate was neutralized with Na$_2$CO$_3$ and extracted with 5:1 dichloromethane/ ethanol. The extract was dried (MgSO$_4$), filtered, and concentrated. The residue was combined with the filtered solid and purified on silica gel with a gradient of 20%–33% ethyl acetate/dichloromethane to provide the desired compound. Further elution with 10% ethanol/dichloromethane provided Example 1B.

MS (DCI/NH$_3$) m/z 379 (M+H)$^+$.

EXAMPLE 3B 4-(6-methoxy-5-nitro-3,4-dihydro-1-naphthalenyl)-2-methyl-1H-imidazole A solution of diisopropylamine (0.60 mL, 4.3 mmol) in THF (10 mL) at −78° C. was treated with n-butyllithium (2.5M in hexane, 1.4 mL), stirred at −78° C. for 30 minutes, treated with Example 3A in THF (20 mL) over 5 minutes, stirred at −78° C. for 2 hours, treated with methyl iodide (1 mL), stirred at ambient temperature for 1hour, treated with saturated ammonium chloride solution, and extracted with ethyl acetate. The extract was dried (MgSO$_4$), filtered, and concentrated. The residue was treated with 1M HCl, heated to 100° C. for 12 hours, cooled to ambient temperature, neutralized with NaHCO$_3$, and extracted with dichloromethane. The extract was dried (MgSO$_4$), filtered, and concentrated. Purification of the residue on silica gel with 2% ethanol/ammonia-saturated dichloromethane provided the desired compound.

MS (DCI/NH$_3$) m/z 286 (M+H)$^+$.

EXAMPLE 3C tert-butyl 4-(6-methoxy-5-nitro-3,4-dihydro-1-naphthalenyl)-2-methyl-1H-imidazole-1-carboxylate A solution of Example 3B (400 mg, 1.4 mmol) in DMF (20 mL) was treated with di-tert-butyl dicarbonate (1 g, 4.6 mmol), stirred for 30 minutes, heated to 75° C. for 15 minutes and concentrated. Purification of the residue on silica gel with 3:2 hexanes:ethyl acetate provided the desired compound.

MS (DCI/NH$_3$) m/z 386 (M+H)$^+$.

EXAMPLE 3D tert-butyl 4-(5-amino-6-methoxy-1,2,3,4-tetrahydro-1-naphthalenyl)-2-methyl-1H-imidazole-1-carboxylate Example 3C was processed as in Example 1C to provide the desired compound.

MS (DCI/NH$_3$) m/z 358 (M+H)$^+$.

EXAMPLE 3E tert-butyl 4-{6-methoxy-5-[(methylsulfonyl)amino]-1,2,3,4-tetrahydro-1-naphthalenyl}-2-methyl-1H-imidazole-1-carboxylate A solution of Example 3D (440 mg, 1.2 mmol) in dichloromethane (15 mL) was treated sequentially with pyridine (0.30 mL, 3.7 mmol), and methanesulfonyl chloride (0.14 mL, 1.8 mmol) and stirred for 16 hours, treated with NaHCO$_3$ solution and extracted with dichloromethane. The extract was dried (MgSO$_4$), filtered, and concentrated. Purification of the residue on silica gel with 2:3 hexanes:ethyl acetate provided the desired compound.

MS (DCI/NH$_3$) m/z 436 (M+H)$^+$.

EXAMPLE 3F

N-[2-hydroxy-5-(2-methyl-1H-imidazol-4-yl)-5,6,7, 8-tetrahydro-1-naphthalenyl]methanesulfonamide, hydrochloride Example 3E was processed as in Example 2 to provide the desired compound.

mp 233–235° C.;

$^1$H NMR (300 MHz, DMSO-d$_6$) δ 1.61–1.78 (m, 2H), 1.82–1.97 (m, 2H), 2.52 (s, 3H), 2.86 (t, 211), 3.03 (s, 3H), 4.13 (t, 1H), 6.73 (q, 2H), 7.04 (s, 1H), 8.58 (s, 1H), 9.83 (s, 1H), 13.98 (bs, 2H);

MS (DCI/NH$_3$) m/z 322 (M+H)$^+$;

Anal. calcd for C$_{15}$H$_{20}$N$_3$O$_3$SCl C, 50.35; H, 5.63; N, 11.74. Found: C, 50.07; H, 5.67; N, 11.55.

EXAMPLE 4

N-[2-hydroxy-5-(1-methyl-1H-imidazol-5-yl)-5,6,7, 8-tetrahydro-1-naphthalenyl]methanesulfonamide, hydrochloride

EXAMPLES 4A AND 4B

4A (Minor)

5-(3,4-dihydro-6-methoxy-5-nitro-1-naphthalenyl)-1-methyl-1H-imidazole 4B (Major)

4-(3,4-dihydro-6-methoxy-5-nitro-1-naphthalenyl)-1-methyl-1H-imidazole

A solution of Example 1B (1.14 g, 4.2 mmol) in DMF (5 mL) was treated with sodium hydride (60% dispersion, 200 mg, 5.0 mmol), stirred for 30 minutes, treated with methyl iodide (0.32 mL, 5.0 mmol), stirred for 1.5 hours, treated with water (300 mL) and extracted with diethyl ether. The extract was washed sequentially with water and brine, dried (MgSO$_4$), filtered, and concentrated. Purification of the residue on silica gel with 12:1:1 ethyl acetate/water/formic acid provided (after conversion of each to the free base by partitioning between dichloromethane and sodium bicarbonate solution and then drying (MgSO$_4$), filtering and concentrating each of the dichloromethane layers) the less polar isomer (designated 4A) and the more polar isomer (designated 4B).

MS (DCI/NH$_3$) m/z 286 (M+H)$^+$ for each product.

EXAMPLE 4C 2-methoxy-5-(1-methyl-1H-imidazol-5-yl)-5,6,7,8-tetrahydro-1-nahthalenamine Example 4A was processed as in Example 1C to provide the desired compound.

MS (DCI/NH$_3$) m/z 258 (M+H)$^+$.

EXAMPLE 4D

N-[2-methoxy-5-(1-methyl-1H-imidazol-5-yl)-5,6,7, 8-tetrahydro-1-naphthalenyl]methanesulfonamide Example 4C was processed as in Example 1E to provide the desired compound.

MS (DCI/NH$_3$) m/z 336 (M+H)$^+$.

EXAMPLE 4E

N-[2-hydroxy-5-(1-methyl-1H-imidazol-5-yl)-5,6,7, 8-tetrahydro-1-naphthalenyl]methanesulfonamide, hydrochloride A solution of Example 4D (0.27 g, 0.80 mmol) in dichloromethane (50 mL) at −78° C. was treated with BBr$_3$ (1M) in dichloromethane (3.2 mL), stirred at 0° C. for 1.5 hours, cooled to −78° C., treated with methanol (5 mL), warmed to ambient temperature and concentrated. Purification of the residue on silica gel with 10% ethanol in ammonia-saturated dichloromethane provided an oil which was converted to the hydrochloride salt provide the desired compound.

mp 260° C.;

$^1$H NMR (300 MHz, DMSO-d$_6$) δ 1.62–1.73 (m, 2H), 1.71–1.85 (m, 1H), 1.88–2.01 (m, 1H), 2.77–2.94 (m, 2H), 3.03 (s, 3H), 3.80 (s, 3H), 4.33 (t, 1H), 6.73 (q, 2H), 6.97 (d, 1H), 8.59 (s, 1H), 9.03 (s, 1H), 9.86 (s, 1H), 14.25 (bs, 1H);

MS (DCI/NH$_3$) m/e 322 (M+H)$^+$;

Anal. calcd for C$_{15}$H$_{19}$N$_3$O$_3$SCl: C, 50.35; H, 5.63; N, 11.74. Found: C, 50.34; H, 5.60; N, 11.53.

EXAMPLE 5

N-[2-hydroxy-5-(1-methyl-1H-imidazol-4-yl)-5,6,7, 8-tetrahydro-1-naphthalenyl]methanesulfonamide, hydrochloride

EXAMPLE 5A 2-methoxy-5-(1-methyl-1H-imidazol-4-yl)-5,6,7,8-tetrahydro-1-naphthalenamine Example 4B was processed as in Example 1C to provide the desired compound.

MS (DCI/NH$_3$) m/z 258 (M+H)$^+$.

EXAMPLE 5B

N-[2-methoxy-5-(1-methyl-1H-imidazol-4-yl)-5,6,7, 8-tetrahydro-1-naphthalenyl]methanesulfonamide Example 5A was processed as in Example 1E to provide the desired compound.

MS (DCI/NH$_3$) m/z 336 (M+H)$^+$.

EXAMPLE 5C

N-[2-hydroxy-5-(1-methyl-1H-imidazol-4-yl)-5,6,7, 8-tetrahydro-1-naphthalenyl]methanesulfonamide, hydrochloride Example 5B was processed as in Example 2 to provide the desired compound.

mp 256–258° C.;

$^1$H NMR (300 MHz, DMSO-d$_6$) δ 1.61–1.72 (m, 2H), .1.87–1.98 (m, 2H), 2.85 (t, 2H), 3.03 (s, 3H), 3.78 (s, 3H), 4.20 (t, 1H), 6.75 (q, 2H), 7.17 (s, 1H), 8.59 (s, 1H), 9.00 (s, 1H),

MS (DCI/NH$_3$) m/z 322 (M+H)$^+$;

Anal. calcd. for C$_{15}$H$_{20}$N$_3$O$_3$SCl: C, 50.35; H, 5.63; N, 11.74. Found: C, 50.15; H, 5.57; N, 11.45.

EXAMPLE 6

N-[5-(1-ethyl-1H-imidazol-4-yl)-2-hydroxy-5,6,7,8-tetrahydro-1-naphthalenyl]methanesulfonamide, hydrochloride

EXAMPLE 6A 1-ethyl-4-(6-methoxy-5-nitro-3,4-dihydro-1-naphthalenyl)-1H-imidazole A solution of Example 1B (1.5 g, 5.5 mmol) in DMF (25 mL) was treated with sodium hydride (60% dispersion, 270 mg, 6.6 mmol), stirred for 30 minutes, treated with ethyl iodide (0.53 mL, 6.6 mmol), stirred for 1 hour, treated with water (300 mL) and extracted with diethyl ether (200 mL). The extract was washed sequentially with water, and brine, dried (MgSO$_4$), filtered and concentrated. Purification of the residue on silica gel with ammonia-saturated ethyl acetate provided, as the less polar isomer, 0.95 g (57%) of the desired compound.

MS (DCI/NH$_3$) m/z 300 (M+H)$^+$.

EXAMPLE 6B 5-(1-ethyl-1H-imidazol-4-yl)-2-methoxy-5,6,7,8-tetrahydro-1-naphthalenamine Example 6A (0.91 g, 3.0 mmol) was processed as in Example 1C to provide the desired compound.

MS (DCI/NH$_3$) m/z 272 (M+H)$^+$.

EXAMPLE 6C

N-[5-(1-ethyl-1H-imidazol-4-yl)-2-methoxy-5,6,7,8-tetrahydro-1-naphthalenyl]methanesulfonamide Example 6B was processed as in Example 1E to provide the desired compound.

MS (DCI/NH$_3$) m/z 350 (M+H)$^+$.

EXAMPLE 6D

N-[5-(1-ethyl-1H-imidazol-4-yl)-2-hydroxy-5,6,7,8-tetrahydro-1-naphthalenyl]methanesulfonamide, hydrochloride Example 6C was processed as in Example 2 to provide the desired compound.

mp 230–234° C. (decomp.);

$^1$H NMR (300 MHz, DMSO-d$_6$) δ 1.40 (t, 3H), 1.62–1.73 (m, 2H), 1.88–2.01 (m, 2H), 2.85 (t, 2H), 3.03 (s, 3H), 4.13 (q, 2H), 4.20 (t, 1H), 6.77 (q, 2H), 7.29 (d, 1H), 8.61 (s, 1H), 9.12 (d, 1H), 9.91 (s, 1H), 14.64 (bs, 1H);

MS (DCI/NH$_3$) m/z 336 (M+H)$^+$;

Anal. calcd for C$_{16}$H$_{22}$ClN$_3$O$_3$S: C, 51.68; H, 5.96; N, 11.30. Found: C, 51.64; H, 5.91; N, 11.10.

EXAMPLE 7

N-[2-hydroxy-5-(1-propyl-1H-imidazol-4-yl)-5,6,7,8-tetrahydro-1-naphthalenyl]methanesulfonamide, hydrochloride

EXAMPLE 7A 4-(3,4-dihydro-6-methoxy-5-nitro-1-nahthalenyl)-1-propyl-1H-imidazole Example 1B was processed as in Example 6A but substituting propyl iodide for ethyl iodide to provide the less polar isomer as the desired compound.

MS (DCI/NH$_3$) m/z 314 (M+H)$^+$.

EXAMPLE 7B 2-methoxy-5-(1-propyl-1H-imidazol-4-yl)-5,6,7,8-tetrahydro-1-naphthalenamine Example 7A was processed as in Example 1C to provide the desired compound.

MS (DCI/NH$_3$) m/z 286 (M+H)$^+$.

EXAMPLE 7C

N-[2-methoxy-5-(1-propyl-1H-imidazol-4-yl)-5,6,7,8-tetrahydro-1-naphthalenyl]methanesulfonamide Example 7B was processed as in Example 1E to provide the desired compound.

MS (DCI/NH$_3$) m/z 364 (M+H)$^+$.

EXAMPLE 7D

N-[2-hydroxy-5-(1-propyl-1H-imidazol-4-yl)-5,6,7,8-tetrahydro-1-naphthalenyl]methanesulfonamide, hydrochloride Example 7C was processed as in Example 2 to provide the desired compound.

mp 128–133° C. (foam);

$^1$H NMR (300 MHz, DMSO-d$_6$) δ 0.83 (t, 3H), 1.61–1.72 (m, 2H), 1.72–1.85 (m, 2H), 1.86–2.02 (m, 2H), 2.85 (t, 2H), 3.03 (s, 3H), 4.07 (t, 2H), 4.20 (t, 1H), 6.75 (q, 2H), 7.28 (s, 1H), 8.59 (s, 1H), 9.10 (d, 1H), 9.83 (s, 1H), 14.59 (bs, 1H);

MS (DCI/NH$_3$) m/z 350 (M+H)$^+$;

Anal. calcd for C$_{17}$H$_{24}$ClN$_3$O$_3$S 0.75 CH$_3$OH :C, 52.01; H, 6.64; N, 10.25. Found: C, 52.15; H, 6.24; N, 9.84

EXAMPLE 8

N-[5-(1H-imidazol-4-yl)-5,6,7,8-tetrahydro-1-naphthalenyl]methanesulfonamide, hydrochloride

EXAMPLE 8A

N-benzyl-N-(5-oxo-5,6,7,8-tetrahydro-1-naphthalenyl)methanesulfonamide

5-Amino-1-tetralone was processed as in Meyer, M. D, J. Med. Chem. (1997), 40, 1049–1062 to provide the desired compound.

EXAMPLE 8B

N-benzyl-N-[5-(1H-imidazol-4-yl)-7,8-dihydro-1-naphthalenyl]methanesulfonamide

A solution of 4-iodo-N,N-dimethyl-1H-imidazole-1-sulfonamide (1.3 g, 4.2 mmol) in dichloromethane (17 mL) was treated with ethylmagnesium bromide (3.0 M in diethyl ether, 1.4 mL) over 2 minutes, stirred for 30 minutes, treated with Example 8A (1.1 g, 3.5 mmol), stirred for 16 hours and concentrated. The residue was treated with 2 M HCl (30 mL), heated for 2 hours at 100° C., cooled to ambient temperature, neutralized with NaHCO$_3$ and extracted with dichloromethane. The extract was dried (MgSO$_4$), filtered, and concentrated. Purification of the residue on silica gel with 2% ethanol/ammonia-saturated dichloromethane provided the desired compound.

EXAMPLE 8C

N-[5-(1H-imidazol-4-yl)-5,6,7,8-tetrahydro-1-naphthalenyl]methanesulfonamide, hydrochloride Example 8B was processed as in Example 1C to provide the desired compound.

mp 113–114° C. (foam);

$^1$H NMR (300 MHz, DMSO-d$_6$) δ 1.70–1.82 (m, 2H), 1.92–2.04 (m, 2H), 2.83 (t, 2H), 3.03 (s, 3H), 4.34 (t, 1H), 6.82 (d, 1H), 7.14 (t, 1H), 7.23 (d, 1H), 7.26 (s, 1H), 9.03 (s, 1H), 9.07 (s, 1H), 14.36 (bs, 2H);

MS (DCI/NH$_3$) m/z 292 (M+H)$^+$;
Anal. calcd for C$_{14}$H$_{18}$ClN$_3$O$_2$S.0.25 H$_2$O: C, 50.60; H, 5.61; N, 12.64. Found: 50.7; H, 5.74; N, 12.31.

EXAMPLE 9

(+)-N-[(5R)-5-(1H-imidazol-4-yl)-5,6,7,8-tetrahydro-1-naphthalenyl]methanesulfonamide

EXAMPLE 9A tert-butyl 4-{5-[(methylsulfonyl)amino]-1,2,3,4-tetrahydro-1-naphthalenyl}-1H-imidazole-1-carboxylate A solution of the free base of Example 8C (3.6 g, 12 mmol) in DMF (50 mL) was treated with di-tert-butyl dicarbonate (3.0 g, 14 mmol), stirred for 8 hours, treated with diethyl ether (500 mL), washed sequentially with water, and brine, dried (MgSO$_4$), filtered, and concentrated. Purification of the residue on silica gel with 2:1 hexanes:ethyl acetate provided 3.6 g (74%) of the desired compound.

MS (DCI/NH$_3$) m/z 392 (M+H)$^+$.

EXAMPLE 9B (+)-tert-butyl 4-{5-[(methylsulfonyl)amino]-1,2,3,4-tetrahydro-1-naphthalenyl}-1H-imidazole-1-carboxylate The enantiomers of Example 9A were separated by chiral chromatography on a Chiralcel OJ column (5.0 cm inner diameter, 50 cm length, 20 micron packing) using 90:10 hexanes:ethanol at a flow rate of 200 mL/minute as the mobile phase. Four separate injections of 150 mg each in 95:5 ethanol:dichloromethane (6 mL) provided 320 mg of the faster moving enantiomer.

$[\alpha]^{23}_D$ +71.50 (c 1.0, MeOH);
MS (DCI/NH$_3$) m/z 392 (M+H)$^+$.

EXAMPLE 9C (+)-N-[(5R)-5-(1H-imidazol-4-yl)-5,6,7,8-tetrahydro-1-naphthalenyl]methanesulfonamide A solution of Example 9B (130 mg, 0.33 mmol) in methanol (10 mL) was treated with 1N HCl (5 mL), stirred for 1.5 hours, concentrated at 45° C., and dried under vacuum for 30 minutes. The residue was dissolved in methanol, filtered through cotton, concentrated and dried under vacuum for 3 hours to provide the desired compound.

mp 118–123° C. (foam);
$[\alpha]^{23}_D$ +41.8° (c 1.0, MeOH);
MS (DCI/NH$_3$) m/z 292 (M+H)$^+$;
$^1$H NMR (300 MHz, DMSO-d$_6$) δ 1.70–1.82 (m, 2H), 1.92–2.04 (m, 2H), 2.83 (t, 2H), 3.03 (s, 3H), 4.34 (t, 1H), 6.82 (d, 1H), 7.14 (t, 1H), 7.23 (d, 1H), 7.26 (s, 1H), 9.03 (s, 1H), 9.07 (s, 1H), 14.36 (bs, 2H);
Anal. calcd for C$_{14}$H$_{18}$ClN$_3$O$_2$S.0.5 H$_2$O.0.5 MeOH: C, 49.36; H, 6.00; N, 11.91. Found: C, 49.36; H, 6.00; N, 11.91.

EXAMPLE 10

(−)-N-[(5S)-5-(1H-imidazol-4-yl)-5,6,7,8-tetrahydro-1-naphthalenyl]methanesulfonamide

EXAMPLE 10A (−)-tert-butyl 4-{5-[(methylsulfonyl)amino]-1,2,3,4-tetrahydro-1-naphthalenyl}-1H-imidazole-1-carboxylate The title compound (340 mg) was provided as the slower moving enantiomer from the procedure described in Example 9B.

$[\alpha]^{23}_D$ −69.40° (c 1.0, MeOH);
MS (DCI/NH$_3$) m/z 392 (M+H)$^+$.

EXAMPLE 10B (−)-N-[(5S)-5-(1H-imidazol-4-yl)-5,6,7,8-tetrahydro-1-naphthalenyl]methanesulfonamide A solution of the Example 10A (95 mg, 0.24 mmol) in methanol (10 mL) was treated with 1N HCl (5 mL) then processed as in Example 9C to provide the desired compound.

mp 118–123° C. (foam);
$[\alpha]^{23}_D$ −40.80° (c 1.0, MeOH);
$^1$H NMR (300 MHz, DMSO-d$_6$) δ 1.70–1.82 (m, 2H), 1.92–2.04 (m, 2H), 2.83 (t, 2H), 3.03 (s, 3H), 4.34 (t, 1H), 6.82 (d, 1H), 7.14 (t, 1H), 7.23 (d, 1H), 7.26 (s, 1H), 9.03 (s, 1H), 9.07 (s, 1H), 14.36 (bs, 2H);
MS (DCI/NH$_3$) m/z 292 (M+H)$^+$;
Anal. calcd for C$_{14}$H$_{18}$ClN$_3$O$_2$S.0.5 CH$_3$OH.0.5 H$_2$O: C, 49.36; H, 6.00; N, 11.91. Found: C, 49.63; H, 6.04; N, 11.65.

EXAMPLE 11

N-[2-hydroxy-5-(1H-imidazol-4-ylmethyl)phenyl]methanesulfonamide, hydrochloride

EXAMPLE 11A 1H-imidazol-4-yl(4-methoxy-3-nitrophenyl)methanol

A solution of 4-iodo-N,N-dimethyl-1H-imidazole-1-sulfonamide (3.0 g, 10 mmol) in dichloromethane (40 mL) under nitrogen was treated with ethylmagnesium bromide (3.0 M in diethyl ether, 3.3 mL) over 2 minutes, stirred for 30 minutes, treated with 4-methoxy-5-nitrobenzaldehyde (2.0 g, 11 mmol), stirred for 1 hour, stored at 0° C. for 16 hours, concentrated to dryness, treated with 1M HCl(100 mL), heated to 100° C. for 16 hours, cooled to ambient temperature, neutralized with NaHCO$_3$ and extracted with 3:1 dichloromethane:ethanol (5×). The combined extractions were dried (MgSO$_4$), filtered and concentrated. Purification on silica gel with 10% and then 20% ethanol/ammonia-saturated dichloromethane provided the desired compound.

MS (DCI/NH$_3$) m/z 250 (M+H)$^+$.

EXAMPLE 11B (3-amino-4-methoxyyphenyl)(1H-imidazol-4-yl)methanol

Example 11A (3.2 g, 13 mmol) was processed as in Example 1C to provide the desired compound.

MS (DCI/NH$_3$) m/z 220 (M+H)$^+$.

EXAMPLE 11C

N-{5-[hydroxy(1H-imidazol-4-yl)methyl]-2-methoxyphenyl}methanesulfonamide, fumarate A solution of Example 11B (1.5 g, 6.8 mmol) in 8:1 pyridine:dichloromethane (45 mL) was treated with methanesulfonyl chloride (0.56 mL, 7.2 mmol) over 10 minutes and the mixture was concentrated. Purification of the residue on silica gel using 8:1:1 ethyl acetate:H$_2$O:HCOOH provided the formic acid salt of the desired compound which was converted to the free base with silica gel 20% ethanol/ammonia-saturated dichloromethane provided the desired compound which was converted to the fumaric acid salt.

mp 90–93° C. (foam);

$^1$H NMR (300 MHz, DMSO-d$_6$) δ 2.93 (s, 3H), 3.80 (s, 3H), 5.57 (s, 1H), 6.61 (s, 1H) 6.72 (s, 1H), 6.99 (d, 1H), 7.18 (dd, 1H), 7.30 (d, 1H), 7.55 (d, 1H), 8.72 (bs, 1H):

MS (DCI/NH$_3$) m/z 298 (M+H)$^+$.

Anal. calcd for C$_{12}$H$_{15}$N$_3$O$_4$S.C$_4$H$_4$O$_4$.0.75 (C$_2$H$_6$O): C, 47.75; H, .5.56; N, 10.78. Found: C, 47.40; H, 5.32; N, 10.52.

EXAMPLE 11D

N-[5-(1H-imidazol-4-ylmethyl)-2-methoxyphenyl]
methanesulfonamide, hydrochloride A solution of the free base of Example 11C (0.59 g, 2.0 rnmol) in trifluoroacetic acid was treated with triethylsilane (3 mL, 20 rnmol), stirred for 30 minutes and concentrated to dryness. Purification of the residue on silica gel using 10% ethanol/ammonia-saturated dichloromethane provided the desired compound which was converted to the hydrochloric acid salt.

mp 206–208° C.;

$^1$H NMR (300 MHz, DMSO-d$_6$) δ 2.91 (s, 3H), 3.76 (s, 3H), 3.93 (s, 2H), 6.99 (d, 1H), 7.07 (dd, 1H), 7.10 (d, 1H), 7.37 (d, 1H), 8.84 (s, 1H), 8.97 (d, 1H), 14.33 (bs, 2H);

MS (DCI/NH$_3$) m/z 282 (M+H)$^+$;

Anal. calcd for C$_{12}$H$_{16}$ClN$_3$O$_3$S: C, 45.35; H, 5.07; N, 13.22. Found: C, 45.45; H, 5.27; N, 13.05.

EXAMPLE 11E

N-[2-hydroxy-5-(1H-imidazol-4-ylmethyl)phenyl]
methanesulfonamide, hydrochloride Example 11D was processed as in Example 2 to provide the desired compound.

mp 167–169° C.;

$^1$H NMR (300 MHz, DMSO-d$_6$) δ 2.94 (s, 3H), 3.92 (s, 2H), 6.87 (d, 1H), 6.96 (dd, 1H), 7.10 (d, 1H), 7.40 (s, 1H), 8.77 (s, 1H), 9.00 (s, 1H), 9.93 (s, 1H), 14.31 (bs, 2H);

MS (DCI/NH$_3$) m/z 268 (M+H)$^+$;

Anal. calcd for C$_{11}$H$_{14}$ClN$_3$O$_3$S: C, 43.49; H, 4.65; N, 13.83. Found: C, 43.58; H, 4.76; N, 13.80.

EXAMPLE 12

N-[5-(1H-imidazol-4-yl)-5,6,7,8-tetrahydro-1-
naphthalenyl]ethanesulfonamide, maleate

EXAMPLE 12A 4-(5-nitro-3,4-dihydro-1-naphthalenyl)-1H-
imidazole

A solution of 4-iodo-1-trityl-1H-imidazole (5.5 g, 13 mmol) (prepared as described by Kirk, K. J. Heterocyclic Chem. (1985), 22, 57–59) in dichloromethane (50 mL) was treated with ethylmagnesium bromide (3.0 M in diethyl ether, 4.2 mL) over 4 minutes, stirred for 30 minutes, treated with 5-nitrotetralone (prepared as described by Zhang, M J. Amer. Chem. SoC, (1994), 116, 4852–4857), stirred for 6 hours, treated with ammonium chloride solution (50 mL) and extracted with a mixture of diethyl ether (300 mL) and ethyl acetate (50 mL). The organic layer was isolated, treated with dichloromethane (500 mL) to dissolve the product which started to crystallize, dried (MgSO$_4$), filtered, concentrated, treated with trifluoroacetic acid (80 mL), stirred for 48 hours, concentrated to an oil, neutralized with sodium bicarbonate solution and extracted twice with dichloromethane. The combined dichloromethane layers were dried (MgSO$_4$), filtered and concentrated. The residue was purified on silica gel with a gradient of 5%–10% methanol/dichloromethane to provide the desired compound.

MS (DCI/NH$_3$) m/z 242 (M+H)$^+$.

EXAMPLE 12B tert-butyl 4-(5-nitro-3,4-dihydro-1-naphthalenyl)-
1H-imidazole-1-carboxylate A solution of Example 12A (1.9 g, 7.9 mmol) in N,N-dimethylformamide (25 mL) was treated with di-tert-butyl bicarbonate (3.4 g, 16 mmol), stirred at ambient temperature for 2 hours, heated to 50° C. for 15 minutes, cooled, diluted with diethyl ether (250 mL), washed with water (2×, 100 mL), washed with brine, dried (MgSO$_4$), filtered and concentrated. Purification of the residue on silica gel with 3:1 hexanes:ethyl acetate provided the desired compound.

MS (DCI/NH$_3$) m/z 342 (M+H)$^+$.

EXAMPLE 12C tert-butyl 4-(5-amino-1,2,3,4-tetrahydro-1-
naphthalenyl)-1H-imidazole-1-carboxylate Example 12B was processed as in Example 1C substituting ethyl acetate for methanol as the solvent. Purification of the residue on silica gel with 1:1 hexanes:ethyl acetate provided the desired compound.

MS (DCI/NH$_3$) m/z 314 (M+H)$^+$.

EXAMPLE 12D

N-[5-(1H-imidazol-4-yl)-5,6,7,8-tetrahydro-1-
naphthalenyl]ethanesulfonamide, maleate A solution of Example 12C (260 mg, 0.83 mmol) in dichloromethane (5 mL) was treated sequentially with pyridine (0.20 mL, 2.5 mmol) and ethanesulfonyl chloride (0.087 mL, 0.91 mmol), stirred for 16 hours, treated with trifluoroacetic acid (3 mL), stirred for 30 minutes and concentrated. Purification of the residue on silica gel with a gradient of 5%–10% ethanol in ammonia-saturated dichloromethane provided a solid which was converted to the maleic acid salt to provide the desired compound.

mp 129–132° C.;

$^1$H NMR (DMSO-d$_6$) δ 1.28 (t, 3H), 1.67–1.85 (m, 2H), 1.87–2.06 (m, 2H), 2.83 (t, 2H), 3.13 (q, 2H), 4.30 (t, 1H), 6.05 (s, 2H), 6.80 (d, 1H), 7.12 (t, 1H), 7.16–7.23 (m, 2H),

MS (DCI/NH$_3$) m/z 306 (M+H)$^+$;

Anal. calcd for C$_{15}$H$_{19}$N$_3$O$_2$S.C$_4$H$_4$O$_4$: C, 54.15; H, 5.50; N, 9.97. Found: C, 54.24; H, 5.53; N, 9.87.

EXAMPLE 14

N-[5,6,7,8-tetrahydro-5-(1-methyl-1H-imidazol-4-
yl)-1-naphthalenyl]methanesulfonamide,
hydrochloride

EXAMPLE 14A

N-benzyl-N-[5-(1-methyl-1H-imidazol-4-yl)-7,8-
dihydro-1-naphthalenyl]methanesulfonamide Example 8B was processed as in Example 4A and 4B to provide the desired product as the more polar isomer.

MS (DCI/NH$_3$) m/z 394 (M+H)$^+$.

EXAMPLE 14B

N-[5,6,7,8-tetrahydro-5-(1-methyl-1H-imidazol-4-yl)-1-naphthalenyl]methanesulfonamide, hydrochloride Example 14A was processed as in Example 1C to provide the desired product which was converted to the hydrochloride salt.

mp 130–135° C.;

$^1$H NMR (DMSO-$d_6$) δ 1.68–1.79 (m, 2H), 1.93–2.03 (m, 2H), 2.88 (t, 2H), 3.03 (s, 3H), 3.79 (s, 3H), 4.33 (t, 1H), 6.87 (d, 1H), 7.15 (t, 1H), 7.20–7.26 (m, 2H), 9.01 (s, 1H), 9.06 (s, 1H), 14.57 (bs, 1H);

MS (DCI/NH$_3$) m/z 306 (M+H)$^+$;

Anal. calcd for $C_{15}H_{19}N_3O_2S \cdot HCl \cdot 0.5 H_2O$: C, 51.35; H, 6.03; N, 11.98. Found: C, 51.10; H, 5.98; N, 11.82.

EXAMPLE 15

N-[5,6,7,8-tetrahydro-5-(1H-imidazol-4-yl)-1-naphthalenyl]-N-methylmethanesulfonmamide, maleate

EXAMPLE 15A

N-(5-oxo-5,6,7,8-tetrahydro-1-naphthalenyl)methanesulfonamide

5-Amino-1-tetralone (Itoh, K. Chem. Pharm. Bull. (1984), 32, 130–151) was processed as in Meyer, M. d. J. Med. Chem. (1997), 40, 1049–1062 to provide the desired product.

EXAMPLE 15B

N-(methoxymethyl)-N-(5-oxo-5,6,7,8-tetrahydro-1-naphthalenyl)methanesulfonamide

A solution of Example 15A (4.0 g, 17 mmol) in anhydrous DMF (40 mL) under a nitrogen atmosphere was treated with a 60% dispersion of sodium hydride (0.74 g, 18 mmol) in portions over 5 minutes, stirred for 45 minutes, cooled to 0° C., treated dropwise with chloromethyl methyl ether (1.3 mL, 18 mmol), stirred at ambient temperature for 2 hours, treated with cold water (250 mL) and extracted with diethyl ether (3x). The combined diethyl ether extracts were washed with water, washed with brine, dried (MgSO$_4$), filtered and concentrated. Purification of the residue on silica gel with 1:1 hexanes:ethyl acetate provided the desired product.

MS (DCI/NH$_3$) m/z 265 (M+NH$_4$)$^+$.

EXAMPLE 15C

N,N-dimethyl-4-{5-[(methylsulfonyl)amino]-3,4-dihydro-1-naphthalenyl}-1H-imidazole-1-sulfonamide Example 15B was processed as in Example 3A to provide the desired product.

MS (DCI/NH$_3$) m/z 397 (M+H)$^+$.

EXAMPLE 15D

N,N-dimethyl-4-{5-[(methylsulfonyl)amino]-1,2,3,4-tetrahydro-1-naphthalenyl}-1H-imidazole-1-sulfonamide Example 15C was processed as in Example 1C to provide the desired product.

MS (DCI/NH$_3$) m/z 399 (M+H)$^+$.

EXAMPLE 15E

N,N-dimethyl-4-{5-[methyl(methylsulfonyl)amino]-1,2,3,4-tetrahydro-1-naphthalenyl}-1H-imidazole-1-sulfonamide A solution of Example 15D (0.30 g, 0.75 mmol) in anhydrous DMF (3 mL) under nitrogen was treated with 60% sodium hydride (0.033 g, 0.83 mmol), stirred for 15 minutes, treated with iodomethane (0.056 mL, 0.90 mmol), stirred for 16 hours, diluted with diethyl ether (100 mL), washed with water, washed with brine, dried (MgSO$_4$), filtered and concentrated. Purification of the residue on silica gel with ethyl acetate provided the desired product.

MS (DCI/NH$_3$) m/z 413 (M+H)$^+$.

EXAMPLE 15F

N-[5-(1H-imidazol-4-yl)-5,6,7,8-tetrahydro-1-naphthalenyl]-N-methylmethanesulfonamide, maleate A solution of Example 15E (0.28 mg, 0.68 mmol) in 1M HCl (10 mL) and THF (10 mL) was refluxed for 48 hours, cooled to ambient temperature, treated with dichloromethane, washed with sodium bicarbonate solution, dried (MgSO$_4$), filtered and concentrated. Purification of the residue on silica gel with 4% ethanol/ammonia-saturated dichloromethane provided a solid which was converted to the maleic acid salt to provide the desired product.

mp 146–147° C.;

$^1$H NMR (DMSO-$d_6$) δ 1.67–2.07 (m, 4H), 2.70–2.86 (m, 1H), 2.87–3.01 (m, 1H), 3.08 and 3.09 (s and s, 3H), 3.12 and 3.13 (s and s, 3H), 4.24–4.35 (m, 1H), 6.05 (s, 2H), 6.94 (t, 1H), 7.13–7.24 (m, 2H), 7.37 (d, 1H), 8.85 (s, 1H);

MS (DCI/NH$_3$) m/z 306 (M+H)$^+$;

Anal. calc'd for $C_{15}H_{19}N_3O_2S \cdot C_4H_4O_4$: C, 54.15; H, 5.50; N, 9.97. Found: C, 54.15; H, 5.67; N, 9.77.

EXAMPLE 16

N-[5,6,7,8-tetrahydro-5-(1H-imidazol-4-yl)-1-naphthalenyl]acetamide, maleate

Example 12C was processed as in Example 12D but substituting acetic anhydride for ethanesulfonyl chloride to provide the desired product which was converted to the maleic acid salt.

mp 159–160° C.;

$^1$H NMR (DMSO-$d_6$) δ 1.67–1.86 (m, 2H), 1.88–2.04 (m, 2H), 2.06 (s, 3H), 2.68 (t, 2H), 4.30 (t, 1H), 6.05 (s, 2H), 6.73 (d, 1H), 7.19 (t, 1H), 7.21 (s, 1H), 7.30 (d, 1H), 8.86 (s, 1H), 9.22 (s, 1H);

MS (DCI/NH$_3$) m/z 256 (M+H)$^+$;

Anal. calcd for $C_{15}H_{17}N_3O \cdot C_4H_4O_4$: C, 61.45; H, 5.70; N, 11.31. Found: C, 61.47; H, 5.87; N, 11.33.

EXAMPLE 17

2,2,2-trifluoro-N-[5-(1H-imidazol-4-yl)-5,6,7,8-tetrahydro-1-naphthalenyl]acetamide, maleate Example 12C was processed as in Example 12D but substituting trifluoroacetic anhydride for ethanesulfonyl chloride to provide the desired product which was converted to the maleic acid salt.

mp 181–182° C.;

¹H NMR (DMSO-d₆) δ 1.67–1.85 (m, 2H), 1.92–2.06 (m, 2H), 2.65 (t, 2H), 4.33 (t, 1H), 6.05 (s, 2H), 6.93 (dd, 1H), 7.16–7.23 (m, 3H), 8.83 (s, 1H), 10.92 (s, 1H);

MS (DCI/NH₃) m/z 310 (M+H)⁺;

Anal. calcd for $C_{15}H_{14}N_3OF_3 \cdot C_4H_4O_4$: C, 53.65; H, 4.27; N, 9.88. Found: C, 53.53; H, 4.17; N, 9.87.

EXAMPLE 18

N-[5,6,7,8-tetrahydro-5-(1H-imidazol-4-yl)-1-naphthalenyl]-2-methylethanesulfonamide, maleate Example 12C was processed as in Example 12D but substituting isopropylsulfonyl chloride for ethanesulfonyl chloride to provide the desired product which was converted to the maleic acid salt.

mp 124–125° C.;

¹H NMR (DMSO-d₆) δ 1.30 (d, 6H), 1.69–1.83 (m, 2H), 1.89–2.02 (m, 2H), 2.83 (t, 2H), 3.25–3.36 (m, 1H), 4.28 (t, 1H), 6.04 (s, 2H), 6.79 (d, 1H), 7.10 (t, 1H), 7.16–7.23 (m, 2H), 8.82 (bs, 1H), 8.94 (s, 1H);

MS (DCI/NH₃) m/z 320 (M+H)⁺;

Anal. calcd for $C_{16}H_{21}N_3O_2S \cdot C_4H_4O_4$: C, 55.16; H, 5.79; N, 9.65. Found: C, 55.12; H, 5.82; N, 9.56.

EXAMPLE 19

N-[4-(1H-imidazol-4-yl)-3,4-dihydro-2H-chromen-8-yl]methanesulfonamide, maleate

EXAMPLE 19A 4-(8-nitro-2H-chromen-4-yl)-1H-imidazole

8-Nitrochroman-4-one (Chakravarti, D. J.Indian Chem. Soc. (1939), 16, 639–644) was processed as in Example 12A to provide the desired product.

MS (DCI/NH₃) m/z 244 (M+H)⁺.

EXAMPLE 19B tert-butyl 4-(8-nitro-2H-chromen-4-yl)-1H-imidazole-1-carboxylate Example 19A was processed as described in Example 12B to provide the desired product.

MS (DCI/NH₃) m/z 344 (M+H)⁺.

EXAMPLE 19C tert-butyl 4-(8-amino-3,4-dihydro-2H-chromen-4-yl)-1H-imidazole-1-carboxylate Example 19B was processed as in Example 1C but substituting ethyl acetate for methanol as the solvent to provide the desired product.

MS (DCI/NH₃) m/z 299 (M+H)⁺.

EXAMPLE 19D

N-[4-(1H-imidazol-4-yl)-3,4-dihydro-2H-chromen-8-yl]methanesulfonamide, maleate

Example 19C was processed as in Example 12D but substituting methanesulfonyl chloride for ethanesulfonyl chloride to provide the desired product which was converted to the maleic acid salt.

mp 172–174° C.;

¹H NMR (DMSO-d₆) δ 2.22 (m, 2H), 2.99 (s, 3H), 4.25 (m, 2H), 4.40 (t, 1H), 6.06 (s, 2H), 6.78 (dd, 1H), 6.83 (t, 1H), 7.16 (dd, 1H), 7.29 (s, 1H), 8.80 (s, 1H), 8.88 (s, 1H);

MS (APCI+) m/z 294 (M+H)⁺;

Anal. calcd for $C_{13}H_{15}N_3O_3S \cdot C_4H_4O_4$: C, 49.87; H, 4.68; N, 10.26. Found: C, 50.03; H, 4.88; N, 10.24.

EXAMPLE 20

N-[5,6,7,8-tetrahydro-5-(1H-imidazol-4-yl)-1-naphthalenyl]-2,2,2-trifluoroethanesulfonamide, maleate

EXAMPLE 20A tert-butyl 4-(5-{[(2,2,2-trifluoroethyl)sulfonyl]amino}-1,2,3,4-tetrahydro-1-naphthalenyl)-1H-imidazole-1-carboxylate Example 12C was processed as in Example 33A but substituting 2,2,2-trifluoroethanesulfonyl chloride for ethanesulfonyl chloride to provide the desired product.

MS (DCI/NH₃) m/z 460 (M+H)⁺.

EXAMPLE 20B

N-[5,6,7,8-tetrahydro-5-(1H-imidazol-4-yl)-1-naphthalenyl]-2,2,2-trifluoroethanesulfonamide, maleate A solution of Example 20A in trifluoroacetic acid (10 mL) was mixed for 15 minutes, concentrated, dissolved in 5:1 methanol:water (6 mL) and applied to an ion exchange resin (25 g of Dowex® 50×8–200 ion-exchange resin). The resin was washed with water until neutral, washed with methanol and the desired product was then flushed from the resin using 5% ammonium hydroxide solution in 1:1 methanol-:dichloromethane. Concentration of the product containing fraction provided a solid which was converted to the maleic acid salt providing the desired product.

mp 138–140° C.;

¹H NMR (DMSO-d₆) δ 1.68–1.82 (m, 2H), 1.90–2.05 (m, 2H), 2.81 (t, 2H), 4.30 (t, 1H); 4.52 (q, 2H), 6.05 (s, 2H), 6.88 (d, 1H), 7.10–7.20 (m, 2H), 7.21 (d, 1H), 8.83 (s, 1H);

MS (DCI/NH₃) m/z 360 (M+H)⁺;

Anal. calcd for $C_{15}H_{16}N_3O_2SF_3 \cdot C_4H_4O_4$: C, 48.00; H, 4.24; N, 8.84. Found: C, 47.99; H, 4.35; N, 9.09.

EXAMPLE 21

N-[3-(1H-imidazol-4-ylmethyl)phenyl]methanesulfonamide, maleate

EXAMPLE 21A

4-[hydroxy(3-nitrophenyl)methyl]-N,N-dimethyl-1H-imidazole-1-sulfonamide

3-Nitrobenzaldehyde was substituted for 6-methoxy-5-nitro-1-tetralone and processed as in Example 1A to provide the desired product.

EXAMPLE 21B

4-[(3-aminophenyl)(hydroxy)methyl]-N,N-dimethyl-1H-imidazole-1-sulfonamide

Example 21A was processed as in Example 1C but substituting ethyl acetate for methanol to provide the desired product.

MS (DCI/NH₃) mIz 297 (M+H)⁺.

EXAMPLE 21C 4-(3-aminobenzyl)-N,N-dimethyl-1H-imidazole-1-sulfonamide

A solution of Example 21B (0.72 g, 2.4 mmol) in trifluoroacetic acid (20 mL) was treated with triethylsilane (3.5 mL), refluxed for 3 hours and concentrated. Purification of the residue on silica gel using 2% ethanol/ammonia-saturated dichloromethane provided a product which was purified on silica gel using ethyl acetate to provide the desired product.

MS (DCI/NH$_3$) m/z 281 (M+H)$^+$.

EXAMPLE 21D

N-[3-(1H-imidazol-4-ylmethyl)phenyl]methanesulfonamide, maleate

A solution of Example 21C (0.22 g, 0.78 mmol) in dichloromethane (3 mL) was treated with pyridine (0.19 mL, 2.4 mmol), treated with methanesulfonyl chloride (0.067 mL, 0.86 mmol), stirred for 1 hour, concentrated to dryness, treated with 1M HCl (5 mL) and tetrahydrofuran (2 mL), refluxed for 2 hours and concentrated. Purification of the residue on silica gel with 10% and then 20% ethanol/ammonia-saturated dichloromethane provided a product which was converted to the maleic acid salt to provide the desired product.

mp 142–144° C.;
$^1$H NMR (DMSO-d$_6$) δ 2.99 (s, 3H), 3.99 (s, 2H), 6.05 (s, 2H), 6.98 (d, 1H), 7.08 (m, 2H), 7.30 (t, 1H), 7.39 (s, 1H), 8.83 (s, 1H), 9.75 (s, 1H);
MS (DCI/NH$_3$) m/z 352 (M+H)$^+$;
Anal. calcd for C$_{11}$H$_{13}$N$_3$O$_2$S.C$_4$H$_4$O$_4$: C, 49.04; H, 4.66; N, 11.44. Found: C, 49.02; H, 4.67; N, 11.24.

EXAMPLE 22

N-[1-(1H-imidazol-4-yl)-2,3-dihydro-1H-inden-4-yl]methanesulfonamide, maleate

EXAMPLE 22A 4-(7-nitro-1H-inden-3-yl)-1H-imidazole

4-Nitroindanone (Hasbun, J. A. J. Med. Chem. (1973), 16, 847–847) was processed as in Example 26B to provide the desired product.

MS (DCI/NH$_3$) m/z 228 (M+H)$^+$.

EXAMPLE 22B tert-butyl 4-(7-nitro-1H-inden-3-yl)-1H-imidazole-1-carboxylate

Example 22A was processed as in Example 38C to provide the desired product.

EXAMPLE 22C tert-butyl 4-(4-amino-2,3-dihydro-1H-inden-1-yl)-1H-imidazole-1-carboxylate Example 22B was processed as in Example 1C but substituting ethyl acetate for methanol as the solvent to provide the desired product.

MS (DCI/NH$_3$) m/z 300 (M+H)$^+$.

EXAMPLE 22D

N-[1-(1H-imidazol-4-yl)-2,3-dihydro-1H-inden-4-yl]methanesulfonamide, maleate

Example 22C was processed as in Example 12D but substituting methanesulfonyl chloride for ethanesulfonyl chloride and substituting triethyl amine for pyridine to provide the desired product which was converted to the maleic acid salt.

mp 168–169° C.;
$^1$H NMR(CD$_3$OD) δ 2.17 (m, 1H), 2.64 (m, 1H), 2.97–3.09 (m, 1H), 3.01 (s, 3H), 3.19 (m, 1H), 4.62 (t, 1H), 6.25 (s, 2H), 6.95 (d, 1H), 7.23 (t, 1H), 7.29 (d, 1H), 7.31 (d, 1H), 8.75 (d, 1H);
MS (DCI/NH$_3$) m/z 278 (M+H)$^+$;
Anal. calcd for C$_{13}$H$_{15}$N$_3$O$_2$S.C$_4$H$_4$O$_4$: C, 51.90; H, 4.87; N, 10.68. Found: C, 52.12; H, 4.72; N, 10.57.

EXAMPLE 23

N-[5,6,7,8-tetrahydro-5-(1H-imidazol-4-yl)-4-methyl-1-naphthalenyl]methanesulfonamide, maleate

EXAMPLE 23A

N-(4-methyl-5-oxo-5,6,7,8-tetrahydro-1-naphthalenyl)methanesulfonamide

A solution of 5-amino-8-methyltetralone (De, B. Synth. Commun. (1988), 18, 481–486) (0.25 g, 1.4 mmol) in dichloromethane (7 mL) was treated with pyridine (0.35 mL, 4.3 mmol), treated with methanesulfonyl chloride (0.12 mL, 1.5 mmol), stirred at ambient temperature for 1.5 hours, treated with aqueous ammonium chloride solution (20 mL) and extracted with dichloromethane (4×25 mL). The combined dichloromethane extracts were washed with brine, dried (Na$_2$SO$_4$) and concentrated. Purification of the residue on silica gel with ethyl acetate:hexanes 1:1 provided the desired product.

MS (APCI+) m/z 244 (M+H)$^+$.

EXAMPLE 23B

N-(methoxymethyl)-N-(4-methyl-5-oxo-5,6,7,8-tetrahydro-1-naphthalenyl)methanesulfonamide Example 23A was processed as in Example 15B to provide the desired product.

MS (APCI+) m/z 298 (M+H)$^+$.

EXAMPLE 23C

N-[5-(1H-imidazol-4-yl)-4-methyl-7,8-dihydro-1-naphthalenyl]methanesulfonamide

A solution of 4-iodo-1-trityl-1H-imidazole (0.44 g, 1.0 mmol) (prepared as described by Kirk, K. J. J. Heterocyclic Chem. (1985), 22, 57–59) in dichloromethane (5 mL) under nitrogen was treated with ethylmagnesium bromide (0.33 mL, 1.0 mmmol) over 4 minutes, stirred for 1 hour, cooled to 0° C., treated with Example 23B, stirred at ambient temperature for 2 hours, treated with water and extracted with ethyl acetate (3×50 mL). The combined ethyl acetate extracts were washed with brine, dried (Na$_2$SO$_4$), concentrated, treated with trifluoroacetic acid (20 mL), stirred for 1.5 hours, treated with water (7 mL), stirred over night and concentrated. Purification of the residue on silica gel with 7% ethanol/ammonia-saturated dichloromethane provided the desired product.

MS (APCI+) m/z 304 (M+H)$^+$.

EXAMPLE 23D

N-[5,6,7,8-tetrahydro-5-(1H-imidazol-4-yl)-4-methyl-1-naphthalenyl]methanesulfonamide, maleate Example 23C was processed as in Example 1C to provide the desired product which was converted to the maleic acid salt.

mp 192–195° C.;

¹H NMR (DMSO-d₆) δ 1.38 (m, 1H), 1.69–2.07 (m, 3H), 2.01 (s, 3H), 2.66 (m, 1H), 2.94 (m, 1H), 3.00 (s, 3H), 4.31 (m, 1H), 6.06 (s, 2H), 6.75 (s, 1H), 7.05 (d, 1H), 7.19 (d, 1H), 8.92 (s, 2H);

MS (APCI+) m/z 306 (M+H)⁺;

MS (APCI−) m/z 304 (M−H)⁻, 340 (M+Cl)⁻;

Anal. calcd for $C_{15}H_{19}N_3O_2S \cdot C_4H_4O_4 \cdot 0.5\ H_2O \cdot 0.25\ C_4C_8O_2$: C, 53.09; H, 5.79; N, 9.29. Found: C, 52.87; H, 5.58; N, 9.20.

EXAMPLE 24

N-[5,6,7,8-tetrahydro-4-hydroxy-5-(1H-imidazol-4-yl)-1-naphthalenyl]methanesulfonamide, maleate Example 26F was processed as in Example 2 to provide the desired product which was converted to the maleic acid salt.

mp 127–131° C.;

¹H NMR (DMSO-d₆) δ 1.44 (m, 1H), 1.74 (m, 1H), 1.85 (m, 1H), 1.96 (m, 1H), 2.62 (m, 1H), 2.91 (m, 1H), 2.95 (s, 3H), 4.29 (d, 1H), 6.04 (s, 2H), 6.66 (d, 1H), 6.85 (s, 1H), 7.07 (d, 1H), 8.75 (s, 1H), 8.85 (s, 1H);

MS (DCI/NH₃) m/z 308 (M+H)⁺;

Anal. calcd for $C_{14}H_{17}N_3O_2S \cdot C_4H_4O_4$: C, 49.99; H, 5.13; N, 9.72. Found: C, 49.96; H, 5.21; N, 9.60.

EXAMPLE 25

N-[5,6,7,8-tetrahydro-(1H-imidazol-4-yl)-4-methoxy-1-naphthalenyl]ethanesulfonamide, maleate Example 26D was processed as in Example 12D to provide the desired product which was converted to the maleic acid salt.

mp 149–151° C.;

¹H NMR (DMSO-d₆) δ 1.28 (t, 3H), 1.42 (m, 1H), 1.74 (m, 1H), 1.84 (m, 1H), 1.98 (m, 1H), 2.66 (m, 1H), 2.94 (m, 1H), 3.08 (q, 2H), 3.63 (s, 3H), 4.33 (d, 1H), 6.04 (s, 2H), 6.78 (s, 1H), 6.84 (d, 1H), 7.20 (d, 1H), 8.83 (s, 2H);

MS (DCI/NH₃) m/z 336 (M+H)⁺;

Anal. calcd for $C_{16}H_{21}N_3O_3S \cdot C_4H_4O_4$: C, 53.21; H, 5.58; N, 9.31. Found: C, 53.11; H, 5.72; N, 9.14.

EXAMPLE 26

N-[5,6,7,8-tetrahydro-(1H-imidazol-4-yl)-4-methoxyy-1-naphthalenyl]methanesulfonamide, maleate

EXAMPLE 26A 8-methoxy-5-nitro-3,4-dihydro-1(2H)-naphthalenone

A solution of 8-methoxy-1-tetralone (2.26 g, 13 mmol) (prepared as described in Chatterjee, A. Tetrahedron, (1980), 36, 2513–2520) in acetic anhydride (11.5 mL) was cooled to 0° C., treated with a mixture of fuming nitric acid (0.90 mL) in acetic acid (0.70 mL) dropwise over 1 hour, stirred at 0° C. for 1.5 hours, treated with water (150 mL) and extracted with diethyl ether (300 mL). The diether ether layer was washed with water (150 mL), washed with sodium bicarbonate solution (3×), washed with brine, dried (MgSO₄), filtered and concentrated. Purification of the residue on silica gel using a gradient of 2:1 and then 3:2 and finally 1:1 hexanes:ethyl acetate provided the desired product as the more polar isomer.

mp 65–71° C.;

¹H NMR (CDCl₃) δ 2.09 (m, 2H), 2.68 (7, 2H), 3.21 (t, 2H), 4.00 (s, 3H), 6.96 (d, 1H), 8.13 (d, 1H);

MS (DCI/NH₃) m/z 222 (M+H)⁺.

EXAMPLE 26B 4-(8-methoxy-5-nitro-3,4-dihydro-1-naphthalenyl)-1H-imidazole

A solution of 4-iodo-1-trityl-1H-imidazole (prepared as described by Kirk, K. J. J. Heterocyclic Chem. (1985), 22, 57–59) (2.2 g, 5.1 mmol), in dichloromethane (20 mL) under nitrogen was treated with ethylmagnesium bromide (1.7 mL, 5.1 mmol) over 2 minutes, stirred for 30 minutes, treated with Example 26A (0.94 g, 4.2 mmol) in dichloromethane (5 mL), stirred for 2 hours, treated with ammonium chloride solution and extracted with dichloromethane (×2). The combined dichloromethane layers were dried (MgSO₄), filtered, concentrated, treated with ethyl acetate and hexane at which time the product was allowed to crystallize for 15 minutes. The crystals were collected by filtration, washed with 5:1 hexanes:ethyl acetate, dried under vacuum, treated with trifluoroacetic acid (25 mL), heated to reflux for 30 minutes, concentrated, treated with sodium bicarbonate solution and extracted with dichloromethane (×2). The combined dichloromethane extracts were dried (MgSO₄), filtered and concentrated to provide the desired product.

EXAMPLE 26C tert-butyl 4-(8-methoxy-5-nitro-3,4-dihydro-1-naphthalenyl)-1H-imidazole-1-carboxylate A suspension of the product from Example 26B in acetonitrile (20 mL) was treated with di-tert-butyl dicarbonate (1 g, 4.6 mmol), heated on a steam bath for 20 minutes and concentrated. Purification of the residue on silica gel with 1:1 hexanes:ethyl acetate provided the desired product.

MS (DCI/NH₃) m/z 372 (M+H)⁺.

EXAMPLE 26D tert-butyl 4-(5-amino-8-methoxy-1,2,3,4-tetrahydro-1-naphthalenyl)-1H-imidazole-1-carboxylate Example 26C was processed as in Example 1C substituting ethyl acetate for methanol as the solvent to provide the desired crude product.

MS (DCI/NH₃) mn/z 344 (M+H)⁺.

EXAMPLE 26E tert-butyl 4-{8-methoxy-5-[(methylsulfonyl)amino]-1,2,3.4-tetrahydro-1-naphthalenyl}-1H-imidazole-1-carboxylate A solution of Example 26D (0.50 g, 1.5 mmol) in dichloromethane (5 mL) was treated with pyridine (0.34 mL, 4.4 mmol), treated with methanesulfonyl chloride (0.17 mL, 2.2 mmol) and stirred for 1.5 hours. Purification of the mixture on silica gel eluting with ammonia-saturated dichloromethane and then with 10% ethyl acetate/ammonia-saturated dichloromethane provided the desired product which was dried under vacuum.

MS (DCI/NH₃) m/z 422 (M+H)⁺.

EXAMPLE 26F

N-[5,6,7,8-tetrahydro-(1H-imidazol-4-yl)-4-methoxy-1-naphthalenyl]methanesulfonamide, maleate Example 26E was processed as in Example 33C to provide the desired product which was converted to the maleic acid salt.

mp 181–184° C.;

¹H NMR (DMSO-d$_6$) δ 1.43 (m, 1H), 1.75 (m, 1H), 1.85 (m, 1H), 1.97 (m, 1H), 2.66 (m, 1H), 2.93 (m, 1H), 2.98 (s, 3H), 3.64 (s, 3H), 4.34 (d, 1H), 6.04 (s, 2H), 6.82 (s, 1H), 6.86 (d, 1H), 7.24 (d, 1H), 8.85 (s, 1H), 8.87 (s, 1H);

MS (DCI/NH$_3$) m/z 322 (M+H)$^+$;

Anal. calcd for C$_{15}$H$_{19}$N$_3$O$_3$S.C$_4$H$_4$O$_4$: C, 52.17; H, 5.30; N, 9.61. Found: C, 51.95; H, 5.34; N, 9.31.

EXAMPLE 27

N-[5,6,7,8-tetrahydro-(1H-imidazol-4-yl)-1-naphthalenyl]cyclopropanesulfonamide, maleate Example 12C was processed as in Example 12D but substituting cyclopropylsulfonyl chloride (prepared as described in King, J. F. J. Org. Chem., (1993), 58, 1128–1135) for ethanesulfonyl chloride to provide the desired product which was converted to the maleic acid salt.

mp 156–157° C.;

¹H NMR (DMSO-d$_6$) δ 0.88 (m, 2H), 0.97 (m, 2H), 1.76 (m, 2H), 1.97 (m, 2H), 2.65 (m, 1H), 2.87 (t, 2H), 4.30 (t, 1H), 6.04 (s, 2H), 6.82 (d, 1H), 7.12 (t, 1H), 7.17 (s, 1H), 7.24 (d, 1H), 8.85 (s, 1H), 9.07 (s, 1H);

MS (DCI/NH$_3$) m/z 318 (M+H)$^+$;

Anal. calcd for C$_{16}$H$_{19}$N$_3$O$_2$S.C$_4$H$_4$O$_4$: C, 55.42; H, 5.35; N, 9.69. Found: C, 55.40; H, 5.35; N, 9.67.

EXAMPLE 28

N-[3-(1H-imidazol-4-ylmethyl)-2-methylphenyl]methanesulfonamide, maleate

EXAMPLE 28A 2-methyl-3-nitrobenzaldehyde o-Tolualdehyde was nitrated and the majority of the undesired 2-methyl-5-nitrobenzaldehyde was removed as described in (Pitzele, B. S. J. Med. Chem., (1988), 31, 138–144) to provide a 2.7:1 ratio of 2-methyl-3-nitrobenzaldehyde: 2-methyl-5-nitrobenzaldehyde.

EXAMPLE 28B

4-[hydroxy(2-methyl-3-nitrophenyl)methyl]-N,N-dimethyl-1H-imidazole-1-sulfonamide Example 28A (0.66 g) was processed as in Example 1A but was purified by recrystallization from ethyl acetate instead of by chromatography to provide the desired products as a mixture enriched in the 3-nitro isomer.

MS (DCI/NH$_3$) m/z 341 (M+H)$^+$.

EXAMPLE 28C

N,N-dimethyl-4-(2-methyl-3-nitrobenzyl)-1H-imidazole-1-sulfonamide

A solution of Example 28B in trifluoroacetic acid (15 mL) was treated with triethyl silane (1.5 mL), heated to reflux for 16 hours, cooled, concentrated, tritrated with hexanes, treated with sodium bicarbonate solution and extracted with dichloromethane (×2). The combined dichloromethane layers were dried (MgSO$_4$), filtered and concentrated. Purification of the residue on silica gel with ether provided the desired product enriched in the 3-nitro isomer.

MS (DCI/NH$_3$) m/z 325 (M+H)$^+$.

EXAMPLE 28D 4-(3-amino-2-methylbenzyl)-N,N-dimethyl-1H-imidazole-1-sulfonamide Example 28C was processed as in Example 1C substituting ethyl acetate for methanol as the solvent. Purification of the residue on silica gel with 2% ethyl acetate/ammonia-saturated dichloromethane provided the desired product as the less polar isomer.

MS (DCI/NH$_3$) m/z 295 (M+H)$^+$.

EXAMPLE 28E

N-[3-(1H-imidazol-4-ylmethyl)-2-methylphenyl]methanesulfonamide, maleate

Example 28D was processed as in Example 31D to provide the desired product which was converted to the maleic acid salt.

mp 143–144° C.;

¹H NMR (DMSO-d$_6$) δ 2.25 (s, 3H), 2.96 (s, 3H), 4.02 (s, 2H), 6.05 (s, 2H), 7.05 (dd, 1H), 7.18 (t, 1H), 7.22 (dd, 1H), 7.26 (s, 1H), 8.83 (d, 1H), 9.12 (s, 1H);

MS (DCI/NH$_3$) m/z 266 (M+H)$^+$;

Anal. calcd for C$_{12}$H$_{15}$N$_3$O$_2$S.C$_4$H$_4$O$_4$: C, 50.39; H, 5.02; N, 11.02. Found: C, 50.32; H, 4.86; N, 10.90.

EXAMPLE 29

N-[3-(1H-imidazol-4-ylmethyl)-2-methylphenyl]ethanesulfonamide, maleate

Example 28D was processed as in Example 31D but substituting ethanesulfonyl chloride for methanesulfonyl chloride to provide the desired product which was converted to the maleic acid salt.

mp 146–147° C.;

¹H NMR (DMSO-d$_6$) δ 1.26 (t, 3H), 3.25 (s, 3H), 3.06 (q, 2H), 4.01 (s, 2H), 6.05 (s, 2H), 7.02 (dd, 1H), 7.17 (m, 2H), 7.24 (d, 1H), 8.80 (d, 1H), 9.07 (s, 1H);

MS (DCI/NH$_3$) m/z 280 (M+H)$^+$;

Anal. calcd for C$_{13}$H$_{17}$N$_3$O$_2$S.C$_4$H$_4$O$_4$: C, 51.64; H, 5.35; N, 10.63. Found: C, 51.64; H, 5.08; N, 10.45.

EXAMPLE 30

N-[3-(1H-imidazol-4-ylmethyl)phenyl]ethanesulfonamide, maleate

Example 21C was processed as in Example 21D but substituting ethanesulfonyl chloride for methanesulfonyl chloride to provide the desired product which was converted to the maleic acid salt.

mp 107–109° C.;

¹H NMR (DMSO-d$_6$) δ 1.18 (t, 3H), 3.08 (q, 2H), 3.99 (s, 2H), 6.05 (s, 2H), 6.96 (d, 1H), 7.08 (m, 2H), 7.28 (m, 1H), 7.37 (d, 1H), 8.80 (d, 1H), 9.77 (s, 1H);

MS (DCI/NH$_3$) m/z 266 (M+H)$^+$;

Anal. calcd for C$_{12}$H$_{15}$N$_3$O$_2$S.C$_4$H$_4$O$_4$: C, 50.39; H, 5.02; N, 11.02. Found: C, 50.44; H, 4.91; N, 10.89.

EXAMPLE 31

N-[3-[1-(1H-imidazol-4-yl)ethyl]phenyl]methanesulfonamide, maleate

EXAMPLE 31A

4-[1-hydroxy-1-(3-nitropheyl)ethyl]-N,N-dimethyl-1H-imidazole-1-sulfonamide 3-nitroacetophenone was processed as in Example 1A to provide the desired product.

MS (DCI/NH$_3$) m/z 341 (M+H)$^+$.

EXAMPLE 31B

N,N-dimethyl-4-[1-(3-nitrophenyl)vinyl]-1H-imidazole-1-sulfonamide

Example 31A was treated with trifluoroacetic acid (30 mL), heated briefly on a steam bath, stirred at ambient temperature for 16 hours, heated to reflux for 1 hour, concentrated, treated with sodium bicarbonate solution and extracted with dichloromethane (2×). The combined dichloromethane extracts were dried (MgSO$_4$), filtered and concentrated. Purification of the residue on silica gel with 4:1 ethyl acetate:hexanes and then ethyl acetate provided the desired product.

MS (DCI/NH$_3$) m/z 323 (M+H)$^+$.

EXAMPLE 31C

4-[1-(3-aminophenylaethyl]-N,N-dimethyl-1H-imidazole-1-sulfonamide

Example 31B was processed as in Example 1C but substituting ethyl acetate for methanol as the solvent to provide the desired product.

MS (DCI/NH$_3$) m/z 295 (M+H)$^+$.

EXAMPLE 31D

N-[3-[1-(1H-imidazol-4-yl)ethyl]phenyl]methanesulfonamide, maleate

A solution of Example 31C (0.19 g, 0.55 mmol) in dichloromethane (7 mL) was treated with pyridine (0.14 mL, 1.7 mmol), treated with methanesulfonyl chloride (0.65 mL, 0.83 mmol), stirred for 16 hours at room temperature, concentrated to dryness, treated with 2M HCl (7 mL), refluxed for 16 hours and concentrated. Purification of the residue on silica gel with 10% ethanol/ammonia-saturated dichloromethane provided the desired product which was converted to the maleic acid salt.

mp 135–136° C.;

$^1$H NMR (DMSO-d$_6$) δ 1.55 (d, 3H), 2.98 (s, 3H), 4.20 (q, 1H), 6.05 (s, 2H), 6.98 (d, 1H), 7.05 (s, 1H), 7.08 (d, 1H), 7.30 (t, 1H), 7.47 (s, 1H), 8.84 (s, 1H), 9.75 (s, 1H);

MS (DCI/NH$_3$) m/z 266 (M+H)$^+$;

Anal. calcd for C$_{12}$H$_{15}$N$_3$O$_2$S.C$_4$H$_4$O$_4$: C, 50.39; H, 5.02; N, 11.02. Found: C, 50.27; H, 4.99; N, 10.90.

EXAMPLE 33

(+)-N-[5-(1H-imidazol-4-yl)-5,6,7,8-tetrahydro-1-naphthalenyl]ethanesulfonamide, maleate

EXAMPLE 33A tert-butyl 4-{5-[(ethylsulfonyl)amino]-1,2,3,4-tetrahydro-1-naphthalenyl}-1H-imidazole-1-carboxylate A solution of Example 12C (2.0 g, 6.4 mmol) in dichloromethane (30 mL) was treated with pyridine (1.6 mL, 19 mmol), treated with ethanesulfonyl chloride (0.91 mL, 9.6 mmol), stirred for 16 hours, diluted with dichloromethane and washed with 1M HCl. The aqueous layer was extracted with dichloromethane (2×) and the combined dichloromethane layers were dried (MgSO$_4$), filtered and concentrated. Purification of the residue on silica gel with 2:1:1 ethyl acetate:dichloromethane:hexane provided the desired product.

MS (DCI/NH$_3$) m/z 406 (M+H)$^+$.

EXAMPLE 33B (+)-tert-butyl 4-{(1R)-5-[(ethylsulfonyl)amino]-1,2,3,4-tetrahydro-1-naphthalenyl}-1H-imidazole-1-carboxylate The enantiomers of Example 33A were separated by chiral chromatography on a Chiracel OJ column (5.0 cm inner diameter, 50 cm length, 20 micron packing) using 95:5 hexanes:ethanol at a flow rate of 117 mL/minute as the mobile phase.

$[\alpha]^{23}_D$ +59.9 (c 1.1, CHCl$_3$).

EXAMPLE 33C (+)-N-[5-(1H-imidazol-4-yl)-5,6,7,8-tetrahydro-1-naphthalenyl]ethanesulfonamide, maleate A solution of the faster moving enantiomer from Example 33B (0.26 g, 0.64 mmol) in dichloromethane (4 mL) was treated with trifluoroacetic acid (5 mL), heated on a steam bath for 1 minute and concentrated. Purification of the residue on silica gel using 5% and then 10% methanol/ammonia-saturated dichloromethane provided a solid which was converted to the maleic acid salt.

mp 129–130° C.;

$[\alpha]^{23}_D$ (free base)+55.2 (c 1.1, 1:1 methanol:chloroform);

$^1$H NMR (DMSO-d$_6$) δ 1.28 (t, 3H), 1.67–1.85 (m, 2H), 1.87–2.06 (m, 2H), 2.83 (t, 2H), 3.13 (q, 2H), 4.30 (t, 1H), 6.05 (s, 2H), 6.80 (d, 1H), 7.12 (t, 1H), 7.16–7.23 (m, 2H);

MS (DCI/NH$_3$) m/z 306 (M+H)$^+$;

Anal. calcd for C$_{15}$H$_{19}$N$_3$O$_2$S.C$_4$H$_4$O$_4$: C, 54.15; H, 5.50; N, 9.97. Found: C, 54.03; H, 5.40; N, 9.87.

EXAMPLE 34

(−)-N-[5-(1H-imidazol-4-yl)-5,6,7,8-tetrahydro-1-naphthalenyl]ethanesulfonamide, maleate

EXAMPLE 34A (−)-tert-butyl 4-{(1R)-5-[(ethylsulfonyl)amino]-1,2,3,4-tetrahydro-1-naphthalenyl}-1H-imidazole-1-carboxylate The title compound was provided by Example 33B as the slower moving enantiomer.

$[\alpha]^{23}_D$ −60.4 (c 1.1, CHCl$_3$).

EXAMPLE 34B (−)-N-[5-(1H-imidazol-4-yl)-5,6,7,8-tetrahydro-1-naphthalenyl]ethanesulfonamide, maleate Example 34A was processed as described in 33C to provide the desired product which was converted to the maleic acid salt.

mp 129–130° C.;

$[\alpha]^{23}_D$ (free base)−56.1° (c 1.0, 1:1 methanol:chloroform);

$^1$H NMR (DMSO-d$_6$) δ 1.28 (t, 3H), 1.67–1.85 (m, 2H), 1.87–2.06 (m, 2H), 2.83 (t, 2H), 3.13 (q, 2H), 4.30 (t, 1H), 6.05 (s, 2H), 6.80 (d, 1H), 7.12 (t, 1H), 7.16–7.23 (m, 2H);

MS (DCI/NH$_3$) m/z 306 (M+H)$^+$;

Anal. calcd for C$_{15}$H$_{19}$N$_3$O$_2$S.C$_4$H$_4$O$_4$: C, 54.15; H, 5.50; N, 9.97. Found: C, 54.44; H, 5.70; N, 9.97.

EXAMPLE 35

(−)-N-[5,6,7,8-tetrahydro-5-(1H-imidazol-4-yl)-1-naphthalenyl]-2,2,2-trifluoroethanesulfonamide

EXAMPLE 35A (−)-tert-butyl 4-(-5-{[(2,2,2-trifluoroethyl)sulfonyl]amino}-1,2,3,4-tetrahydro-1-naphthalenyl)-1H-imidazole-1-carboxylate The enantiomers of Example 20A were separated by chiral chromatography on a Chiralpak AD column (5.0 cm inner diameter, 26 cm length, 20 uDp) using 96:4 hexanes:ethanol at a flow rate of 117 mL/minute as the mobile phase to provide the title compound as the faster moving enantiomer.

$[\alpha]^{23}_D$ −48.9° (c 0.95, CHCl$_3$).

EXAMPLE 35B (−)-N-[5,6,7,8-tetrahydro-5-(1H-imidazol-4-yl)-1-naphthalenyl-2,2,2-trifluoroethanesulfonamide A solution of Example 35A (0.20 g, 0.44 mmol) in dichloromethane (4 mL) was treated with trifluoroacetic acid (5 mL), heated on a steam bath for 1 minute and concentrated. Purification of the residue on silica gel using 10% and then 20% methanol/ammonia-saturated dichloromethane provided the desired product.

mp >260° C.;
$^1$H NMR (DMSO-d$_6$) δ 1.61–1.83 (m, 2H), 1.83–2.06 (m, 2H), 2.67–2.87 (m, 2H), 4.06 (t, 1H), 4.48 (q, 2H), 6.64 (s, 1H), 6.95 (d, 1H), 7.08 (t, 1H), 7.17 (d, 1H), 7.54 (s, 1H), 9.8 (bs, 1H), 11.5 (bs, 1H);
$[\alpha]^{23}_D$ −30.20 (c 0.95, acetic acid);
MS (DCI/NH$_3$) m/z 360 (M+H)$^+$;
Anal. calcd for C$_{15}$H$_{16}$N$_3$O$_2$SF$_3$: C, 50.13; H, 4.49; N, 11.69. Found: C, 50.30; H, 4.52; N, 11.51.

EXAMPLE 36

(+)-N-[5,6,7,8-tetrahydro-5-(1H-imidazol-4-yl)-1-naphthalenyl]-2,2,2-trifluoroethanesulfonamide The slower moving enantiomer from Example 35A was processed as in Example 35B to provide the title compound.

mp >260° C.;
$[\alpha]^{23}_D$ +30.4° (c 0.97, acetic acid);
$^1$H NMR (DMSO-d$_6$) δ 1.61–1.83 (m, 2H), 1.83–2.06 (m, 2H), 2.67–2.87 (m, 2H), 4.06 (t, 1H), 4.48 (q, 2H), 6.64 (s, 1H), 6.95 (d, 1H), 7.08 (t, 1H), 7.17 (d, 1H), 7.54 (s, 1H), 9.8 (bs, 1H), 11.5 (bs, 1H);
MS (DCI/NH$_3$) m/z 360 (M+H)$^+$;
Anal. calcd for C$_{15}$H$_{16}$N$_3$O$_2$SF$_3$: C, 50.13; H, 4.49; N, 11.69. Found: C, 50.26; H, 4.47; N, 11.49.

EXAMPLE 37

N-{3-[1-(1H-imidazol-4-yl)ethyl]phenyl}ethanesulfonamide, maleate

Example 31C was processed as in Example 21D but substituting ethanesulfonyl chloride for methanesulfonyl chloride to provide the desired product which was converted to the maleic acid salt.

mp 114–119° C.;
$^1$H NMR (DMSO-d$_6$) δ 1.17 (t, 3H), 1.55 (d, 3H), 3.07 (q, 2H), 4.20 (q, 1H), 6.05 (s, 2H), 6.96 (d, 1H), 7.04–7.12 (m, 2H), 7.28 (t, 1H), 7.45 (s, 1H), 8.82 (d, 1H), 9.76 (s, 1H), 14.00 (bs, 1H);
MS (DCI/NH$_3$) m/z 280 (M+H)$^+$;
Anal. calc'd for C$_{13}$H$_{17}$N$_3$O$_2$S.C$_4$H$_4$O$_4$.0.25 H$_2$O: C, 51.05; H, 5.52; N, 10.51. Found: C, 51.20; H, 5.53; N, 10.31.

EXAMPLE 38

N-[5-(1H-imidazol-4-yl)-6,7,8,9-tetrahydro-5H-benzo[a]cyclohepten-1-yl]methanesulfonamide, maleate

EXAMPLE 38A 1-nitro-6,7,8,9-tetrahydro-5H-benzo[a]cyclohepten-5-one 6,7,8,9-Tetrahydro-5H-benzo[a]cyclohepten-5-one (18.5 g, 11.5 mmol) was mechanically stirred at −15° C. and treated with concentrated sulfuric acid (41 mL) over 5 minutes, stirred 10 minutes, treated dropwise over 10 minutes with a mixture of fuming nitric acid (9 mL) and concentrated sulfuric acid (14 mL), stirred at −15° C. for 15 minutes and poured carefully onto a mixture of ice (200 g) and water (200 mL). The resulting solid was collected by filtration, washed with water (100 mL, 2×), dried and recrystallized from ethanol (200 mL). The resulting solid was removed by filtration and the filtrate was suspended on silica gel and purified on silica gel eluting with ethyl acetate:hexanes 12:88 to provide the desired product.

$^1$H NMR (CDCl$_3$) δ 1.78–1.87 (m, 2H), 1.97–2.06 (m, 2H), 2.74 (7, 2H), 2.98 (t, 2H), 7.44(t, 1H), 7.82 (dd, 1H), 7.91 (dd, 1H).

EXAMPLE 38B 4-(4-nitro-6,7-dihydro-5H-benzo[a]cyclohepten-9-yl)-1H-imidazole Example 38A was processed as in Example 26B to provide the desired product which was carried onto the next step without purification.

EXAMPLE 38C tert-butyl 4-(4-nitro-6,7-dihydro-5H-benzo[a]cyclohepten-9-yl)-1H-imidazole-1-carboxylate Example 38B was processed as in Example 3C but instead of concentrating the dimethylformamide, the mixture was partitioned between ether and water. The ether layer was isolated, washed with water, brine, dried (MgSO$_4$), filtered and concentrated.

MS (DCI/NH$_3$) m/z 356 (M+H)$^+$.

EXAMPLE 38D tert-butyl 4-(1-amino-6,7,8,9-tetrahydro-5H-benzo[a]cyclohepten-5-yl)-1H-imidazole-1-carboxylate Example 38C was processed as in Example 1C but substituting ethyl acetate for methanol as the solvent to provide the desired product.

MS (DCI/NH$_3$) m/z 328 (M+H)$^+$.

EXAMPLE 38E

N-[5-(1H-imidazol-4-yl)-6,7,8,9-tetrahydro-5H-benzo[a]cyclohepten-1-yl]methanesulfonamide, maleate Example 38D was processed as in Example 12D but substituting methanesulfonyl chloride for ethanesulfonyl chloride to provide the desired product which was converted to the maleic acid salt.

mp 162–164° C.;
$^1$H NMR (CD$_3$OD) δ 1.58 (m, 1H), 1.83 (m, 3H), 2.06 (m, 1H), 2.17 (m, 1H), 2.97 (s, 3H), 3.00 (m, 1H), 3.18 (m, 1H), 4.54 (dd, 1H), 6.25 (s, 2H), 7.69 (d, 1H), 7.14 (t, 1H), 7.26 (dd, 1H), 7.29 (s, 1H), 8.81 (d, 1H);
MS (DCI/NH$_3$) m/z 306 (M+H)$^+$;
Anal. calcd for C$_{15}$H$_{19}$N$_3$O$_2$S.C$_4$H$_4$O$_4$.0.5 C$_4$H$_8$O$_2$: C, 54.18; H, 5.85; N, 9.03. Found: C, 53.97; H, 5.82; N, 8.86.

EXAMPLE 39

N-[1-(1H-imidazol4-yl)-2,3-dihydro-1H-inden-4-yl]ethanesulfonamide, maleate

Example 22C was processed as in Example 12D but substituting triethylamine for pyridine to provide the desired product which was converted to the maleic acid salt.

mp 148–149° C.;

$^1$H NMR (CD$_3$OD) δ 1.36 (t, 3H), 2.16 (m, 1H), 2.64 (m, 1H), 2.96–3.24 (m, 2H), 3.14 (q, 2H), 4.62 (t, 1H), 6.25 (s, 2H), 6.92 (d, 1H), 7.21 (t, 1H), 7.29 (m, 2H), 8.76 (d, 1H);

MS (DCI/NH$_3$) m/z 292 (M+H)$^+$;

Anal. calcd for C$_{14}$H$_{17}$N$_3$O$_2$S.C$_4$H$_4$O$_4$: C, 53.06; H, 5.20; N, 10.31. Found: C, 53.06; H, 5.17; N, 10.30.

EXAMPLE 40

N-[5-(1H-imidazol-4-yl)-6,7,8,9-tetrahydro-5H-benzo[a]cyclohepten-1-yl]ethanesulfonamide, maleate Example 38D was processed as in Example 12D to provide the desired product which was converted to the maleic acid salt.

mp 155–156° C.;

$^1$H NMR (CD$_3$OD) δ 1.39 (t, 3H), 1.58 (m, 1H), 1.73–1.92 (m, 3H), 2.05 (m, 1H), 2.18 (m, 1H), 2.99 (m, 1H), 3.10 (q, 2H), 3.19 (m, 1H), 4.54 (dd, 1H), 6.25 (s, 2H), 6.67 (d, 1H), 7.13 (t, 1H), 7.24 (dd, 1H), 7.29 (s, 1H), 8.81 (d, 1H);

MS (DCI/NH$_3$) m/z 320 (M+H)$^+$;

Anal. calcd for C$_{16}$H$_{21}$N$_3$O$_6$S.C$_4$H$_4$O$_4$: C, 55.16; H, 5.79; N, 9.65. Found: C, 54.96; H, 5.67; N, 9.47.

EXAMPLE 41

N-[4-fluoro-3-(1H-imidazol-4-ylmethyl)phenyl]methanesulfonamide, maleate

EXAMPLE 41A

4-[(2-fluoro-5-nitrophenyl)(hydroxy)methyl]-N,N-dimethyl-1H-imidazole-1-sulfonamide 2-Fluoro-5-nitrobenzaldehyde was substituted for 6-methoxy-5-nitro-1-tetralone and processed as described in Example 1A to provide the desired product.

MS (DCI/NH$_3$) m/z 345 (M+H)$^+$.

EXAMPLE 41B 4-(2-fluoro-5-nitrobenzyl)-N,N-dimethyl-1H-imidazole-1-sulfonamide A mixture of Example 41A (0.45 g, 1.3 mmol) and triethylsilane (0.5 g, 4.3 mmol) in trifluoroacetic acid (5 mL) was refluxed for 6 hours, cooled to ambient temperature, concentrated, neutralized with aqueous sodium bicarbonate and extracted (2x) with dichloromethane. The combined dichloromethane extracts were dried (MgSO$_4$), filtered and concentrated. Purification of the residue on silica gel eluting with ethyl acetate:hexanes 1:1 provided the desired product.

MS (DCI/NH$_3$) m/z 329 (M+H)$^+$.

EXAMPLE 41C 4-(5-amino-2-fluorobenzyl)-N,N-dimethyl-1H-imidazole-1-sulfonamide Example 41B was processed as in Example 1C but substituting ethyl acetate for methanol as the solvent to provide the desired product.

MS (DCI/NH$_3$) m/z 299 (M+H)$^+$.

EXAMPLE 41D

N-[4-fluoro-3-(1H-imidazol-4-ylmethyl)phenyl]methanesulfonamide, maleate

Example 41C was processed as described in Example 31D to provide the desired product which was converted to the maleic acid salt.

mp 146–147° C.;

$^1$H NMR (DMSO-d$_6$) δ 2.95 (s, 3H), 4.01 (s, 2H), 6.06 (s, 2H), 7.12 (m, 2H), 7.21 (t, 1H), 7.32 (s, 1H), 8.75 (s, 1H), 9.65 (s, 1H);

MS (DCI/NH$_3$) m/z 270 (M+H)$^+$;

Anal. calcd for C$_{11}$H$_{12}$N$_3$O$_2$SF.C$_4$H$_4$O$_4$: C, 46.75; H, 4.18; N, 10.90. Found: C, 46.63; H, 4.32; N, 10.85.

EXAMPLE 42

N-[4-chloro-5-(1H-imidazol-4-yl)-5,6,7,8-tetrahydro-1-naphthalenyl]ethanesulfonamide, maleate

EXAMPLE 42A 5-amino-8-chloro-3,4-dihydro-1(2H)-naphthalenone

A solution of 5-amino-1-tetralone (Itoh, K. Chem. Pharm. Bull. (1984), 32, 130–151) (0.50 g, 3.1 mmol) in dimethylformamide (15 mL) was treated with N-chlorosuccinimide (0.49 g, 3.7 mmol), stirred for 60 hours, treated with water and extracted with ether (4×30 mL). The combined ether extracts were washed with brine, dried (Na$_2$SO$_4$) and concentrated. Purification of the residue on silica gel with ethyl acetate:hexanes 1:1 provided the desired product.

$^1$H NMR (CDCl$_3$) δ 2.16 (m, 2H), 2.67 (m, 4H), 3.72 (s, 2H), 6.75 (d, 1H), 7.14 (d, 1H);

MS (APCI+) m/z 196 (+H)$^+$.

EXAMPLE 42B

N-(4-chloro-5-oxo-5,6,7,8-tetrahydro-1-naphthalenyl)ethanesulfonamide

A solution Example 42A (0.14 g, 0.72 mmol) in dichloromethane (5 mL) was treated with pyridine (0.18 mL, 2.2 mL), treated with ethanesulfonyl chloride (0.11 mL, 1.1 mmol), stirred for 16 hours, treated with pyridine (1 mL), treated with ethanesulfonyl chloride (0.5 mL), stirred for 3 hours and concentrated. Purification of the residue on silica gel with 5% ethanol/ammonia-saturated dichloromethane provided the desired product.

MS (ESI–) m/z 286 (M–H)$^-$.

EXAMPLE 42C

N-(4-chloro-5-oxo-5,6,7,8-tetrahydro-1-naphthalenyl)-N-(methoxymethyl)ethanesulfonamide Example 42B was processed as described in Example 15B to provide the desired product.

MS (ESI+) m/z 332 (M+H)$^+$, 349 (M+NH$_4$)$^+$.

EXAMPLE 42D

N-[4-chloro-5-(1H-imidazol-4-yl)-7,8-dihydro-1-naphthalenyl]ethanesulfonamide

Example 42C was processed as described in Example 8B except that the 2M HCl mixture was heated to reflux for 16 hours and the mixture was then concentrated to dryness and used without further purification.

EXAMPLE 42E

N-[4-chloro-5-(1H-imidazol-4-yl)-5,6,7,8-tetrahydro-1-naphthalenyl]ethanesulfonamide, maleate Example 42D was processed as described in Example 43D to provide the desired product which was converted to the maleic acid salt.

mp 151–155° C.;
$^1$H NMR (DMSO-d$_6$) δ 1.28 (t, 3H), 1.36–1.49 (m, 1H), 1.72–2.06 (m, 3H), 2.57–2.74 (m, 1H), 2.96 (dd, 1H), 3.16 (q, 2H), 4.43 (d, 1H), 6.05 (s, 2H), 6.80 (s, 1H), 7.31 (s, 2H), 8.81 (s, 1H), 9.12 (s, 1H);
MS (DCI/NH$_3$) m/z 340 (M+H)$^+$;
Anal. calcd for C$_{15}$H$_{18}$N$_3$O$_2$SCl.C$_4$H$_4$O$_4$.0.25 C$_4$H$_8$O$_2$: C, 50.26; H, 5.06; N, 8.79. Found: C, 50.44; H, 5.11; N, 8.70.

EXAMPLE 43

N-[4-chloro-5-(1H-imidazol-4-yl)-5,6,7,8-tetrahydro-1-naphthalenyl]methanesulfonamide, maleate

EXAMPLE 43A

N-(4-chloro-5-oxo-5,6,7,8-tetrahydro-1-naphthalenyl)methanesulfonamide

Example 42A was processed as in Example 42B but substituting methanesulfonyl chloride for ethanesulfonyl chloride to provide the desired product.
MS (APCI−) m/z 272 (M−H)$^−$.

EXAMPLE 43B

N-(4-chloro-5-oxo-5,6,7,8-tetrahydro-1-naphthalenyl)-N-(methoxymethyl)methanesulfonamide Example 43A was processed as in Example 15B to provide the desired product.
MS (APCI+) m/z 318 (M+H)$^+$, 335 (M+NH$_4$)$^+$.

EXAMPLE 43C

N-[4-chloro-5-(1H-imidazol-4-yl)-7,8-dihydro-1-naphthalenyl]methanesulfonamide

Example 43B was processed as described in Example 8B except that the 2M HCl mixture was heated to reflux for 16 hours and the mixture was then concentrated to dryness and used without further purification.

EXAMPLE 43D

N-[4-chloro-5-(1H-imidazol-4-yl)-5,6,7,8-tetrahydro-1-naphthalenyl]methanesulfonamide, maleate A mixture of Example 43C (0.16 g, 0.50 mmol) and 10% Pd/C in 5:1 tetrahydrofuran:5 M HCl (6 mL) was stirred under a hydrogen (1 atmosphere) for 1 hour, filtered and concentrated. Purification of the residue on silica gel with 10% methanol/ammonia-saturated dichloromethane provided the desired product which was converted to the maleic acid salt.
mp 175–178° C.;
$^1$H NMR (DMSO-d$_6$) δ 1.30–1.85 (m, 2H), 1.86–2.08 (m, 2H), 2.60–3.00 (m, 2H), 3.06 (s, 3H), 4.44 (m, 1H), 6.05 (s, 2H), 6.82 (s, 1H), 7.32 (s, 2H), 8.80 (s, 1H), 9.15 (s, 1H);
MS (APCI+) m/z 326 (M+H)$^+$;MS (APCI−) m/z 324 (M−H)$^−$;
Anal. calcd for C$_{14}$H$_{16}$N$_3$O$_2$SCl.C$_4$H$_4$O$_4$: C, 48.91; H, 4.56; N, 9.51. Found: C, 48.62; H, 4.51; N, 9.26.

EXAMPLE 44

N-[4-fluoro-5-(1H-imidazol-4-yl)-5,6,7,8-tetrahydro-1-naphthalenyl]methanesulfonamide, maleate

EXAMPLE 44A 8-fluoro-5-hydroxy-3,4-dihydro-1 (2H)-naphthalenone

A solution of 8-fluoro-5-methoxytetralone (Owton, W. M. J. Chem. Soc., Perkin Trans. 1 (1994), 2131–2135) (7.0 g, 36 mmol) in 1,2-dichlorethane (150 mL) was treated with aluminum chloride-(21 g, 157 mmol), refluxed for 3.5 hours, cooled to ambient temperature, poured carefully into 4M HCl (500 mL), stirred for 16 hours, treated with dichloromethane (400 mL) and thoroughly shaken. A black solid was removed by filteration through Celite®. The dichloromethane layer was isolated, combined with the black solid and extracted with 5% sodium hydroxide solution (3×150 mL). The combined sodium hydroxide extracts were acidified with 4M hydrochloric acid and the resulting solid was collected by filtration to provide the desired product as a brown solid.
MS (APCI+) m/z 181 (M+H)$^+$.

EXAMPLE 44B 4-fluoro-5-oxo-5,6,7,8-tetrahydro-1-naphthalenyl trifluoromethanesulfonate A solution of Example 44A (1.0 g, 5.5 mmol) in pyridine (3 mL) under nitrogen was cooled to 0° C., treated dropwise with trifluoromethanesulfonic anhydride (1.0 mL, 6.2 mmol), stirred for 16 hours at ambient temperature, treated with 2M HCl (25 mL), stirred for 30 minutes and extracted with ethyl acetate (3×70 mL). The combined ethyl acetate extracts were washed with brine and concentrated. Purification of the residue on silica gel with 40% ethyl acetate/hexanes provided the desired product.
MS (APCI+) m/z 330 (M+NH$_4$)$^+$.

EXAMPLE 44C 5-(benzylamino)-8-fluoro-3,4-dihydro-1(2H)-naphthalenone

A mixture of tris(dibenzylideneacetone)dipalladium(0) (0.36 g, 0.34 mmol) under nitrogen in toluene (136 mL) was treated with (R)-(+)-2,2'-bis(diphenylphosphino)-1,1'-binaphthyl (0.96 g, 1.5 mmol), treated with sodium tert-butoxide (0.98 g, 10 mmol), treated with benzyl amine (1.1 mL, 10 mmol), warmed to 85° C., treated dropwise over 45 minutes with a solution of Example 44B (2.1 g, 6.8 mmol) in toluene (30 mL), stirred at 85° C. for 1 hour and treated with water (50 mL). The organic layer was isolated and the aqueous layer was extracted with ethyl acetate. The combined organic layers were washed with brine, dried (Na$_2$SO$_4$) and concentrated. Purification of the residue on silica gel with 30% ethyl acetate/hexanes provided the desired product.
MS (APCI+) m/z 348 (M+H)$^+$, 365 (M+NH$_4$)$^+$.

EXAMPLE 44D

N-benzyl-N-(4-fluoro-5-oxo-5,6,7,8-tetrahydro-1-naphthalenyl)methanesulfonamide

A solution of Example 44C (0.40 g, 1.5 mmol) in dichloromethane (9 mL) was treated with pyridine (0.36 mL, 4.4 mmol), treated with methanesulfonyl chloride (0.13 mL, 1.6 mmol), stirred for 4 hours, treated with pyridine (0.2 mL, 2.5 mmol), treated with methanesulfonyl chloride (0.10 mL, 1.3 mmol), stirred for 16 hours,refluxed for 9 hours, cooled to ambient temperature, treated with water (25 mL) and extracted with dichloromethane (3×20 mL). The combined dichloromethane extracts were washed with brine, dried (Na$_2$SO$_4$) and concentrated. Purification of the residue on silica gel with 1:1 ethyl acetate:hexanes provided the desired product.

EXAMPLE 44E

N-benzyl-N-[4-fluoro-5-(1H-imidazol-4-yl)-7,8-dihydro-1-naphthalenyl]methanesulfonamide Example 44D was processed as in Example 8B to provide the desired product.
MS (APCI+) m/z 398 (M+H)$^+$.

EXAMPLE 44F

N-[4-fluoro-5-(1H-imidazol-4-yl)-5,6,7,8-tetrahydro-1-naphthalenyl]methanesulfonamide, maleate Example 44E was processed as in Example 1C to provide the desired product which was converted to the maleic acid salt.

mp 182–186° C.;
$^1$H NMR (DMSO-d$_6$) δ 1.50 (m, 1H), 1.76 (m, 1H), 1.95 (m, 2H), 2.70 (m, 1H), 2.92 (m, 1H), 3.02 (s, 3H), 4.42 (m, 1H), 6.07 (s, 2H), 6.99 (s, 1H), 7.05 (t, 1H), 7.30 (dd, 1H), 8.86 (s, 1H), 9.08 (s, 1H);
MS (APCI+) m/z 310 (M+H)$^+$;
MS (APCI–) m/z 308 (M–H)$^-$;
Anal. calcd for $C_{14}H_{16}N_3O_2SF \cdot C_4H_4O_4$: C, 50.81; H, 4.74; N, 9.87. Found: C, 50.71; H, 4.87; N, 9.72.

EXAMPLE 45

N-{3-[1-(1H-imidazol-4-yl)vinyl]phenyly}ethanesulfonamide, maleate

EXAMPLE 45A

4-[1-(3-aminophenyl)vinyl]-N,N-dimethyl-1H-imidazole-1-sulfonamide

Example 31B was processed as in Example 46B to provide the desired product.
MS (APCI+) m/z 293 (M+H)$^+$.

EXAMPLE 45B

N-{3-[1-(1H-imidazol-4-yl)vinyl]phenyl}ethanesulfonamide, maleate

Example 45A was processed as in Example 31D except ethanesulfonyl chloride was used instead of methanesulfonyl chloride to provide the desired product which was converted to the maleic acid salt.

mp 151–155° C.;
$^1$H NMR (DMSO-d$_6$) δ 1.20 (t, 3H), 3.11 (q, 2H), 5.44 (s, 1H), 5.81 (s, 1H), 6.11 (s, 2H), 7.15 (d, 1H), 7.25 (d, 1H), 7.27 (s, 1H), 7.34 (s, 1H), 7.38 (dd, 1H), 8.65 (s, 1H), 9.89 (s, 1H);
MS (APCI+) m/z 278 (M+H)$^+$;
MS (APCI–) m/z 276 (M–H)$^-$;
Anal. calcd for $C_{13}H_{15}N_3O_2S \cdot C_4H_4O_4$: C, 51.31; H, 4.94; N, 10.56. Found: C, 51.37; H, 5.07; N, 10.22.

EXAMPLE 46

N-{3-[(Z)-1-(1H-imidazol-4-yl)-2-methoxyethenyl]phenyl}ethanesulfonamide, maleate

EXAMPLE 46A

4-[(Z)-2-methoxy-1-(3-nitrophenyl)ethenyl]-N,N-dimethyl-1H-imidazole-1-sulfonamide A solution of (methoxymethyl)triphenylphosphonium chloride (0.67 g, 1.9 mmol) in tetrahydrofuran (6.4 mL) under a nitrogen atmosphere was treated with a solution of 2.5M n-butyllithium in hexanes (0.78 mL, 1.9 mmol), treated with a solution of Example 55B (0.67 g, 2.0 mmol) in THF (30 mL), stirred for 16 hours, treated with ammonium chloride solution and extracted with ethyl acetate (3×60 ML). The combined ethyl acetate extracts were washed with brine, dried (Na$_2$SO$_4$) and concentrated. Purification of the residue on silica gel with ethyl acetate provided the desired product as the less polar isomer.

$^1$H NMR (CDCl$_3$) δ 2.90 (s, 6H), 3.94 (s, 3H), 6.49 (s, 1H), 7.50 (dd, 1H), 7.66 (d, 1H), 7.74 (m, 1H), 7.83 (d, 1H), 8.12 (m, 1H), 8.24 (t, 1H);
MS (APCI+) m/z 353 (M+H)$^+$.

EXAMPLE 46B

4-[(Z)-1-(3-aminophenyl)-2-methoxyethenyl]-N,N-dimethyl-1H-imidazole-1-sulfonamide A solution of Example 46A (0.15 g, 0.43 mmol) in methanol (0.70 mL) was cooled to 0° C., treated with concentrated HCl (0.35 mL), treated with zinc (0.28 g, 4.3 mmol) in portions, stirred at ambient temperature for 20 minutes, neutralized with aqueous sodium bicarbonate solution (15 mL) and extracted with ethyl acetate (4×20 mL). The combined ethyl acetate extracts were dried (Na$_2$SO$_4$) and concentrated to provide the desired product.

MS (APCI+) m/z 323 (M+H)$^+$.

EXAMPLE 46C 4-((Z)-1-{3-[(ethylsulfonyl)amino]-phenyl}-2-methoxyethenyl)-N,N-dimethyl-1H-imidazole-1-sulfonamide A solution of Example 46B (0.32 g, 0.99 mmol) in dichloromethane (5 mL) was treated with pyridine (0.24 mL, 3.0 mmol), treated with ethanesulfonyl chloride (0.10 mL, 1.1 mmol), stirred for 5 hours, treated with 1M HCl and extracted with dichloromethane (3×). The combined dichloromethane extractions were dried (Na$_2$SO$_4$) and concentrated to provide the title compound.

MS (APCI+) m/z 415 (M+H)$^+$.

EXAMPLE 46D

N-{3-[(Z)-1-(1H-imidazol-4-yl)-2-methoxyethenyl]phenyl}ethanesulfonamide, maleate A solution of Example 46C (0.13 g, 0.32 mmol) in tetrahydrofuran (10 mL) was treated with 1M HCl (15 mL), heated to 50° C. for 16 hours, cooled to ambient temperature, neutralized with sodium bicarbonate solution and extracted with ethyl acetate (2×). The combined ethyl acetate extracts were washed with brine, dried (Na$_2$SO$_4$) and concentrated. Purification of the residue on silica gel with 10% methanol/dichloromethane provided the desired product which was converted to the maleic acid salt.

mp 146–148° C.;
$^1$H NMR (DMSO-d$_6$) δ 1.20 (t, 3H), 3.10 (q, 2H), 3.88 (s, 3H), 6.05 (s, 2H), 6.81 (s, 1H), 7.06 (d, 1H), 7.11 (s, 1H), 7.15 (d, 1H), 7.34 (dd, 1H), 7.42 (s, 1H), 8.81 (s, 1H), 9.81 (s, 1H);
MS (APCI+) m/z 308 (M+H)$^+$;
MS (APCI–) m/z 306 (M–H)$^-$;
Anal. calcd for $C_{14}H_{17}N_3O_3S \cdot C_4H_4O_4$: C, 51.06; H, 5.00; N, 9.92. Found: C, 51.03; H, 5.05; N, 9.79.

EXAMPLE 47

N-[5-(1H-imidazol-4-yl)-7,8-dihydro-1-naphthalenyl]methanesulfonamide, maleate

Example 15B was processed as in Example 8B except that after addition of the 2M HCl, the mixture was heated to reflux for 6 hours. Purification of the residue on silica gel with 10% ethanol/ammonia saturated dichloromethane provided the desired product which was converted to the maleic acid salt.

mp 161–165° C.;

$^1$H NMR (DMSO-d$_6$) δ 2.28–2.38 (m, 2H), 2.85 (t, 2H), 2.98 (s, 3H), 6.07 (s, 2H), 6.49 (t, 1H), 7.11 (dd, 1H), 7.19–7.29 (m, 2H), 7.61 (s, 1H), 8.78 (s, 1H), 9.21 (s, 1H);

MS (DCI/NH$_3$) m/z 290 (M+H)$^+$, 307 (M+NH$_4$)$^+$;

Anal. calcd for C$_{14}$H$_{15}$N$_3$O$_2$S.C$_4$H$_4$O$_4$: C, 53.33; H, 4.72; N. 10.36. Found: C, 53.28; H, 4.83; N, 10.20.

EXAMPLE 55

N-[3-(1-hydroxy-1-(1H-imidazol-4-yl)propyl) phenyl]ethanesulfonamide

EXAMPLE 55A

4-[hydroxy(3-nitrophenyl)methyl]-N,N-dimethyl-1H-imidazole-1-sulfonamide

3-Nitrobenzaldehyde was substituted for 6-methoxy-5-nitro-1-tetralone and processed as described in Example 1A to provide the desired product.

MS (DCI/NH$_3$) m/z 327 (M+H)$^+$.

EXAMPLE 55B

N,N-dimethyl-4-(3-nitrobenzoyl)-1H-imidazole-1-sulfonamide

A mixture of Example 55A (9.78 g, 30 mmol) and barium manganate (40 g, 150 mmol) in toluene (200 mL) was refluxed for 30 minutes. The solid was filtered off and washed with dioxane (500 mL). The filtrate and washings were combined and were concentrated under reduced pressure to provide 9.7 g (84%) of the title compound.

$^1$H NMR (300 MHz, DMSO-d$_6$) δ 2.92 (s, 6H), 7.87 (t, J=9 Hz, 1H), 8.50 (m, 3H), 8.59 (m, 1H), 9.08 (m, 1H);

MS (APCI+) m/z 325 (M+H)$^+$; MS (APCI−) m/z 359 (M+Cl)$^-$.

EXAMPLE 55C 4-(3-aminobenzoyl)-N,N-dimethyl-1H-imidazole-1-sulfonamide

To a mixture of Example 55B (3.24 g, 10 mmol) and NH$_4$Cl (540 mg, 10 mmol) in water (15 mL) and ethanol (35 mL) was added iron powder (3.92 g, 70 mmol) and the mixture was refluxed for 1 hour. The mixture was filtered, the solid was washed with THF, and the combined filtrate and washings were removed under vacuum to provide 3 g (~100%) of the title compound.

EXAMPLE 55D

4-{3-[(ethylsulfonyl)amino]-benzoyl}-N,N-dimethyl-1H-imidazole-1-sulfonamide

A solution of Example 55C in pyridine (30 mL) was treated with ethanesulfonyl chloride (0.11 mL, 11 mmol) at 0° C. The mixture was stirred at room temperature for the next 16 hours and then concentrated under vacuum. The residue was purified by column chromatography (silica gel, ethyl acetate) to provide 2.31 g (57%) of the title compound.

MS (APCI+) m/z 387 (M+H)$^+$; MS (APCI−) m/z 385 (M−H)$^-$, m/z 421 (M+Cl)$^-$.

EXAMPLE 55E

N-[3-(1H-imidazol-4-ylcarbonyl)phenyl] ethanesulfonamide

Example 55D (193 mg, 0.5 mmol) in dioxane (5 mL), methanol (5 mL), and water (5 mL) was treated with 1N HCl (5 mL) and the resulting mixture was refluxed for 35 minutes. The mixture was concentrated under vacuum and the residue was passed through Dowex® 50×8–400 ion exchange resin and eluted with 5% NH$_4$OH. The ammonia solution was concentrated under vacuum and the residue was purified on column (silica gel, 4:1 CH$_2$Cl$_2$-methanol) to provide 85 mg (60%) of the title compound.

MS (APCI+) m/z 280 (M+H)$^+$; MS (APCI−) m/z 278 (M−H)$^-$, m/z 314 (M+Cl)$^-$.

EXAMPLE 55F

N-[3-(1-hydroxy-1-(1H-imidazol-4-yl)propyl) phenyl]ethanesulfonamide

To a solution of Example 55E (84 mg, 0.3 mmol) in THF (10 mL) at 0° C. was added dropwise a 2M solution of ethyl magnesium bromide in ether (0.6 mL, 1.2 mmol) and the resulting mixture was allowed to warm to room temperature for 6 hours. The mixture was quenched with saturated NH$_4$Cl and concentrated under vacuum. The residue was passed through a Dowex® 50×8–400 ion exchange resin with 5% NH$_4$OH as eluent. The ammonia solution was concentrated under vacuum and purified again by chromatography (silica gel, 9:1 CH$_2$Cl$_2$:ethanol) to provide 20 mg of the desired product.

mp 120–124° C.;

$^1$H NMR (300 MHz, DMSO-d$_6$) δ 0.71 (t, J=7 Hz, 3H), 1.15 (t, J=7 Hz, 3H), 2.12 (m, 1H), 3.04 (q, J=7 Hz, 2H), 5.67 (bs, 1H), 7.09 (m, 3H), 7.22 (m, 2H), 7.38 (m, 1H), 8.20 (bs, 1H), 9.71 (bs, 1H);

MS (APCI+) m/z 310 (M+H)$^+$; MS (APCI−) m/z 308 (M−H)$^-$, m/z 344 (M+Cl)$^-$.

EXAMPLE 56

N-[3-(cyclohexylidene-(1H-imidazol-4-ylmethyl) phenyl]ethanesulfonamide

EXAMPLE 56A 4-(cyclohexyl{3-[(ethylsulfonyl)amino]-phenyl}hydroxymethyl)-N,N-dimethyl-1H-imidazole-1-sulfonamide To a solution of Example 55D (154 mg, 0.4 mmol) in THF (10 mL) at 0° C. was added 1M solution in Et$_2$O of cyclohexylmagnesium chloride (1 mL, 1 mmol) and the mixture was left at room temperature for 6 hours. The mixture was quenched with saturated NH$_4$Cl and concentrated under vacuum. The residue was extracted with ethyl acetate, dried (MgSO$_4$) and concentrated under vacuum. Column chromatography (silica gel, 3:5 hexanes:ethyl acetate) provided 160 mg (68%) of alcohol.

MS (APCI+) m/z 471 (M+H)$^+$; MS (APCI−) m/z 469 (M−H)$^-$, m/z 505 (M+Cl)$^-$.

EXAMPLE 56B

N-{3-[cyclohexyl(hydroxy)1H-imidazol-4-ylmethyl] phenyl}ethanesulfonamide

Example 56A was dissolved in dioxane (10 mL) and treated with 2% KOH (2 mL) at reflux for 48 hours. The mixture was concentrated under vacuum and the residue was chromatographed (silica gel, 9:1 CH$_2$Cl$_2$:ethanol and a few drops of concentrated NH$_4$OH) to provide 90 mg (62%) of the title compound.

MS (APCI+) m/z 364 (M+H)$^+$; MS (APCI−) m/z 362 (M−H)$^−$, m/z 398 (M+Cl)$^−$.

EXAMPLE 56C

N-[3-(cyclohexylidene-(1H-imidazol-4-ylmethyl)phenyl]ethanesulfonamide

Example 56B was first acetylated with acetic anhydride (2 mL) in pyridine (5 mL) at 0° C. for 6 hours. The mixture was concentrated under vacuum and then immediately treated with 1N HCl (10 mL) at reflux for 15 hours. The mixture was concentrated under vacuum, and the residue was treated with 5% NH$_4$OH and concentrated under vacuum. The residue was purified by column chromatography (silica gel, 9:1 CH$_2$Cl$_2$:methanol) to provide 20 mg (24%) of the desired product.

mp 75–78° C.;

$^1$H NMR (300 MHz, DMSO-d$_6$) δ 1.16 (t, J=7 Hz, 3H), 1.55 (m, 6H), 2.06 (m, 2H), 2.55 (m, 2H), 3.03 (q, J=7 Hz, 2H), 6.61 (s, 1H), 6.80 (m, 1H), 6.98 (m, 1H), 7.07 (m, 1H), 7.24 (t, J=9 Hz, 1H), 7.55 (m, 1H), 9.72 (s, 1H);

MS (APCI+) m/z 346 (M+H)$^+$; MS (APCI−) m/z 344 (M−H)$^−$, m/z 380 (M+Cl)$^−$.

EXAMPLE 61

N-[5-(1H-imidazol-5-yl)-5,6,7,8-tetrahydro-1-naphthalenyl]-3,5-dimethyl-4-isoxazolesulfonamide

EXAMPLE 61A tert-butyl 4-(5-{[(3,5-dimethyl-4-isoxazolyl)sulfonyl]amino}-1,2,3,4-tetrahydro-1-naphthalenyl)-1H-imidazole-1-carboxylate To a manually agitated 23° C. solution of Example 12C (100 mg, 0.32 mmol) in methylene chloride (5 mL) was added pyridine (0.078 mL, 0.96 mmol) and 3,5-dimethylisoxazole-4-sulfonyl chloride (65.4 mg, 0.34 mmol), and the homogeneous reaction mixture allowed to stand for 10 minutes. The methylene chloride was removed under vacuum. The resultant thick oil was allowed to stand and additional 2 hours and was then chromatographed on flash silica gel (1:1 ethyl acetate/hexanes) to provide the title compound (150 mg, 0.318 mmol, >99% yield).

EXAMPLE 61B

N-[5-(1H-imidazol-4-yl)-5,6,7,8-tetrahydro-1-naphthalenyl]-3,5-dimethyl-4-isoxazolesulfonamide A 0° C. solution of Example 61A (150 mg, 0.318 mmol) in methylene chloride (10 mL) was treated with trifluoroacetic acid (3.2 mL) and stirred for 1.5 hours. The reaction mixture was warmed to room temperature for 2 hours and then cooled to −20° C. for 16 hours. The reaction mixture was warmed to ambient temperature and diluted with methylene chloride and water and neutralized with aqueous saturated NaHCO$_3$. The methylene chloride layer was separated and the aqueous phase extracted twice more with methylene chloride. The combined extracts were dried (MgSO$_4$), filtered, and concentrated under vacuum. The residue was chromatographed on flash silica gel (79:20:1 methylene chloride/methanol/ammonium hydroxide) to provide the title compound (87 mg, 0.23 mmol, 74% yield).

mp 85–210° C.;

$^1$H NMR (300 MHz, CD$_3$OD) δ 1.67 (m, 2H), 1.98 (m, 2H), 2.17 (s, 3H), 2.29 (m, 3H), 6.62 (m, 2H), 4.12 (dd, J=6.9, 6.9 Hz, 1H), 6.52 (bs, 1H), 7.01 (m, 3H), 7.61 (d, J=1.2 Hz, 1H);

MS (APCI+) m/z 373 (M+H)$^+$.

EXAMPLE 63

N-[5-(1H-imidazol-5-yl)-5,6,7,8-tetrahydro-1-naphthalenyl]-1-propanesulfonamide

To a solution of 1-propanesulfonyl chloride (20.5 mg, 0.14 mmol) in dichloromethane (250 mL) was added pyridine (78 mL, 0.96 mmol) followed 5-(1H-imidazol-4-yl)-5,6,7,8-tetrahydro-1-naphthalenamine (30 mg, 0.096 mmol) dissolved in CH$_2$Cl$_2$ (1 mL). The CH$_2$Cl$_2$ was removed under vacuum and the reaction gently shaken at ambient temperature overnight. To the reaction was added 1.0 mL of CH$_2$Cl$_2$ followed by 200 mg of polymer supported trisamine (Argonaut laboratories). The reaction was shaken at room temperature for 30 minutes, the filtrate collected and the volume brought to 5 mL with dichloromethane. The organic layer was extracted with 10% aqueous citric acid (3×4 mL), brine (2×4 mL), filtered (Varian CE1000M)® and the solvent removed under vacuum. The resulting oil was dissolved in 2 mL of acetonitrile and 0.5 g of Amberlyst resin was added. The reaction was shaken at room temperature for 72 hours and filtered. The resin was washed with acetonitrile (2×2 mL), methanol (2×2 mL), and suspended in 2 M methanolic ammonia (2 mL) for 2 hours. The resin was filtered, washed with 0.5 mL of methanol and then retreated with ammonia as described. The ammonia and methanol filtrates were combined and the solvent removed under vacuum. The crude material was purified using reverse phase preparative HPLC. (6.7 mg, 21.9% yield).

$^1$H NMR (500 MHz, DMSO-d$_6$) δ 0.99 (t, J=7.5 Hz, 3H), 1.67 (m, 1H), 1.74 (m, 3H), 1.88 (m, 1H), 2.02 (m, 1H), 2.74 (m, 1H), 2.79 (m, 1H), 3.06 (t, J=7.7 Hz, 2H), 4.00 and 4.12 (2 m, 2.4:1, 1H), 6.44 and 6.54 (2 bs, 1:2.4, 1H), 6.75 and 6.91 (2 bd, 1:2.4, J=7.7, 1H), 7.02 (m, 1H), 7.10 (m, 1H), 7.49 and 7.51 (2 bs, 1:2.4, 1H), 8.85 (bs, 1H), 11.7 and 11.84 (2 bs, 2.4:1, 1H);

MS (APCI−) m/z 319 (M−H)$^−$.

EXAMPLE 64

N-[5-(1H-imidazol-5-yl)-5,6,7,8-tetrahydro-1-naphthalenyl]-1-butanesulfonamide

The desired product was prepared according to the method of Example 63 above substituting 1-butanesulfonyl chloride for 1-propanesulfonyl chloride (7.5 mg, 23.5% yield).

$^1$H NMR (500 MHz, DMSO-d$_6$) δ 0.88 (t, J=7.4 Hz, 3H), 1.40 (m, 2H), 1.69 (m, 3H), 1.76 (m, 1H), 1.89 (m, 1H), 2.02 (m, 1H), 2.74 (m, 1H), 2.79 (m, 2H), 3.08 (t, J=7.77 Hz, 2H), 4.00 and 4.13 (2 m, 2:1, 1H), 6.43 and 6.53 (2 bs, 1:2, 1H), 6.76 and 6.92 (2 bd, 1:2, J=7.7, 1H), 7.03 (m, 1H), 7.10 (m, 1H), 7.49 and 7.51 (2 bs, 1:2, 1H), 8.85 (bs, 1H), 11.70 and 11.85 (2 bs, 2:1, 1H);

MS (APCI−) m/z 333 (M−H)$^−$.

EXAMPLE 65

3-Chloro-N-[5-(1H-imidazol-5-yl)-5,6,7,8-tetrahydro-1-naphthalenyl]-1-propanesulfonamide The desired product was prepared according to the method of Example 63 above substituting 2-chloropropanesulfonyl chloride for 1-propanesulfonyl chloride (7.4 mg, 21.8% yield).

$^1$H NMR (500 MHz, DMSO-d$_6$) δ 1.68 (m, 1H), 1.77 (m, 1H), 1.89 (m, 1H), 2.00 (m, 1H), 2.18 (q, J=6.8 Hz, 2H), 2.80 (m, 2H), 3.25 (m, 2H), 3.77 (t, J=5.0 Hz, 2H), 4.05 (m, 1H), 6.51 (m, 1H), 6.91 (m, 1H), 7.05 (t, J=7.0 Hz, 1H), 7.10 (d, J=7.0 Hz, 1H), 7.51 (d, J=1.9 Hz, 1H), 9.02 (s, 1H), 11.72 and 11.91 (2 bs, 1:2, 1H);

MS (APCI−) m/z 705 (2M−H)$^-$.

EXAMPLE 66

N-[5-(1H-imidazol-5-yl)-5,6,7,8-tetrahydro-1-naphthalenyl]-1-methyl-1H-imidazole-4-sulfonamide The desired product was prepared according to the method of Example 63 above substituting 1-methyl-1H-imidazole-4-sulphonyl chloride for 1-propanesulfonyl chloride (5.0 mg, 14.6% yield).

$^1$H NMR (500 MHz, DMSO-d$_6$) δ 1.56 (m, 1H), 1.64 (m, 1H), 1.80 (m, 1H), 1.97 (m, 1H), 2.63 (m, 1H), 2.67 (m, 1H), 3.65 (s, 3H), 3.97 (m, 1H), 6.34 and 6.43 (bs, 1:1, 1H), 6.46 (s, 1H), 6.9 (m, 2H), 7.49 (m, 1H), 7.57 (s, 1H), 7.77 (s, 1H), 9.15 (bs, 1H), 11.67 and 11.82 (2 bs, 1:1, 1H);

MS (APCI−) m/z 357 (M−H)$^-$.

EXAMPLE 67

N-[5-(1H-imidazol-5-yl)-5,6,7,8-tetrahydro-1-nahthalenyl](phenyl)methanesulfonamide The desired product was prepared according to the method of Example 63 above substituting phenylmethanesulfonyl chloride for 1-propanesulfonyl chloride (6.4 mg, 18.2% yield).

$^1$H NMR (500 MHz, DMSO-d$_6$) δ 1.64 (m, 1H), 1.73 (m, 1H), 1.88 (m, 1H), 2.02 (m, 1H), 2.63 (m, 1H), 2.67 (m, 1H), 4.00 and 4.13 (m, 2:1,1H), 4.43 (s, 2H), 6.45 and 6.54 (2 bs, 1:2, 1H), 6.83 (m, 1H), 7.02 (m, 1H), 7.10 (m, 1H), 7.35 (s, 5H), 7.49 and 7.52 (2 bs, 1:2, 1H), 8.85 (bs, 1H), 11.70 and 11.83 (2 bs, 2:1, 1H);

MS (APCI−) m/z 367 (M−H)$^-$.

EXAMPLE 68

N-[5-(1H-imidazol-5-yl)-5,6,7,8-tetrahydro-1-naphthalenyl]-4-methylbenzenesulfonamide The desired product was prepared according to the method of Example 63 above substituting p-toluenesulfonyl chloride for 1-propanesulfonyl chloride (10.9 mg, 31.0% yield).

$^1$H NMR (500 MHz, DMSO-d$_6$) δ 1.50 (m, 2H), 1.78 (m, 1H), 1.93 (m, 1H), 2.36 (s, 3H), 2.41 (m, 1H), 2.46 (m, 1H), 4.00 (m, 1H), 6.33 and 6.42 (2 bs, 1:2, 1H), 6.77 (m, 1H), 6.86 (m, 1H), 6.92 (m, 1H), 7.33 (d, J=8.1 Hz, 2H), 7.48 (m, 1H), 7.54 (d, J=8.0 Hz, 2H), 9.31 (bs, 1H), 11.68 and 11.80 (2 bs, 2:1, 1H);

MS (APCI−) m/z 367 (M−H)$^-$.

EXAMPLE 69

N-[5-(1H-imidazol-5-yl)-5,6,7,8-tetrahydro-1-naphthalenyl]-2-methylbenzenesulfonamide The desired product was prepared according to the method of Example 63 above substituting o-toluenesulfonyl chloride for 1-propanesulfonyl chloride (10.8 mg, 30.7% yield).

$^1$H NMR (500 MHz, DMSO-d$_6$) δ 1.59 (m, 1H), 1.65 (m, 1H), 1.86 (m, 1H), 2.01 (m, 1H), 2.62 (s, 3H), 4.15 (m, 1H), 6.49(bs, 1H), 6.79 and 6.87 (m, 2:1, 1H), 6.99 (m, 2H), 7.5 (m, 5H), 7.77 (d, J=5.6 Hz, 1H), 9.47 (bs, 1H), 11.75 and 11.80 (2 bs, 2:1, 1H);

MS (APCI−) m/z 367 (M−H)$^-$.

EXAMPLE 70

N-[5-(1H-imidazol-5-yl)-5,6,7,8-tetrahydro-1-naphthalenyl]-2-phenyl-1-ethenesulfonamide The desired product was prepared according to the method of Example 63 above substituting (E)-2-phenylethenesulfonyl chloride for 1-propanesulfonyl chloride (12.2 mg, 33.6% yield).

$^1$H NMR (500 MHz, DMSO-d$_6$) δ 1.63 (m, 1H), 1.70 (m, 1H), 1.84 (m, 1H), 1.95 (m, 1H), 2.80 (m, 2H), 4.00 (bs, 1H), 6.45 (bs, 1H), 6.89 (bs, 1H), 7.01 (t, J=7.5 Hz, 1H), 7.08 (m, 1H), 7.24 (d, J=15.3 Hz, 1H), 7.30 (d, J=15.4 Hz, 1H), 7.42 (m, 3H), 7.49 (bs, 1H), 7.68 (m, 2H), 9.15 (bs, 1H); 11.67 and 11.82 (2 bs, 2:1, 1H);

MS (APCI−) m/z 379 (M−H)$^-$.

EXAMPLE 71

N-[5-(1H-imidazol-5-yl)-5,6,7,8-tetrahydro-1-naphthalenyl]-4-methoxybenzenesulfonamide The desired product was prepared according to the method of Example 63 above substituting 4-methoxybenzenesulfonyl chloride for 1-propanesulfonyl chloride (3.0 mg, 8.2% yield).

$^1$H NMR (500 MHz, DMSO-d$_6$) δ 1.50 (m, 2H), 1.78 (m, 1H), 1.94 (m, 1H), 2.44 (m, 2H), 3.80 (s, 3H), 4.00 (m, 1H), 6.32 and 6.42 (2 bs, 1:2, 1H), 6.79 (m, 1H), 6.87 (m, 1H), 6.93 (m, 1H), 7.05 (d, J=8.8 Hz, 2H), 7.49 (m, 1H), 7.58 (d, J=8.8 Hz, 2H), 9.24 (bs, 1H), 11.67 and 11.80 (2 bs, 2:1, 1H);

MS (APCI−) m/z 383 (M−H)$^-$.

EXAMPLE 72

5-Chloro-N-[5-(1H-imidazol-5-yl)-5,6,7,8-tetrahydro-1-naphthalenyl]-2-thiophenesulfonamide The desired product was prepared according to the method of Example 63 above substituting 5-chlorothiophene-2-sulfonyl chloride for 1-propanesulfonyl chloride (2.8 mg, 7.4% yield).

$^1$H NMR (500 MHz, DMSO-d$_6$) δ 1.54 (m, 1H), 1.60 (m, 1H), 1.82 (m, 1H), 1.93 (m, 1H), 2.50 (m, 2H), 4.00 (m, 1H), 6.43 (s, 1H), 6.89 (m, 2H), 7.02 (t, J=7.9 Hz, 1H), 7.20 (d, J=4.0 Hz, 1H), 7.30 (d, J=4.0 Hz, 1H), 7.51 (d, J=1.1 Hz, 1H), 9.86 (bs, 1H), 11.70 (bs, 1H);

MS (APCI−) m/z 393 (M−H)$^-$.

EXAMPLE 73

N-[5-(1H-imidazol-5-yl)-5,6,7,8-tetrahydro-1-naphthalenyl]-8-quinolinesulfonamide The desired product was prepared according to the method of Example 63 above substituting 8-quinolinesulfonyl chloride for 1-propanesulfonyl chloride (4.0 mg, 10.3% yield).

$^1$H NMR (500 MHz, DMSO-d$_6$) δ 1.49 (m, 1H), 1.58 (m, 1H), 1.78 (m, 1H), 1.91 (m, 1H), 2.58 (m, 1H), 2.65 (m, 1H), 3.89 and 4.02 (m, 2:1, 1H), 6.32 and 6.42 (m, 1:2, 1H), 6.56 (m, 1H), 6.63 (m, 1H), 6.78 (m, 2H), 7.47 (s, 1H), 7.72 (t, J=6.4 Hz, 1H), 7.76 (dd, J=3.2, 6.8 Hz, 1H), 8.25 (dd, J=1.2, 6.0 Hz, 1H), 8.31 (d, J=6.4 Hz, 1H), 8.58 (dd, J=1.6, 6.8 Hz, 1H), 9.2 (bs, 1H), 9.13 (dd, J=1.2, 3.2 Hz, 1H), 11.66 and 11.80 (2 bs, 2:1, 1H);

MS (APCI−) m/z 404 (M−H)−.

EXAMPLE 74

5-Chloro-N-[5-(1H-imidazol-5-yl)-5,6,7,8-tetrahydro-1-naphthalenyl]-1,3-dimethyl-1H-pyrazole-4-sulfonamide The desired product was prepared according to the method of Example 63 above substituting 5-chloro-1,3-dimethyl-4-pyrazolosulfonyl chloride for 1-propanesulfonyl chloride (9.6 mg, 24.7% yield).

$^1$H NMR (500 MHz, DMSO-$d_6$) δ 1.55 (m, 2H), 1.82 (m, 1H), 1.98 (m, 1H), 2.08 (s, 3H), 2.52 (m, 2H), 3.71 (s, 3H), 3.97 and 4.08 (m, 2:1, 1H), 6.28 and 6.39 (m, 1:2, 1H), 6.97 (m, 3H), 7.50 (s, 1H), 9.45 (m, 1H), 11.69 and 11.84 (bs, 1:1, 1H);

MS (APCI−) m/z 405 (M−H)−.

EXAMPLE 75

Methyl 2-({[5-(1H-imidazol-5-yl)-5,6,7,8-tetrahydro-1-naphthalenyl]amino}sulfonyl)-3-thiophenecarboxylate The desired product was prepared according to the method of Example 63 above substituting 2-methoxycarbonyl-3-thiophenesulfonyl chloride for 1-propanesulfonyl chloride (3.6 mg, 9.0% yield).

$^1$H NMR (500 MHz, DMSO-$d_6$) δ 1.46 (m, 1H), 1.54 (m, 1H), 1.69 (m, 1H), 1.80 (m, 1H), 2.48 (m, 2H), 3.70 (s, 3H), 3.86 (m, 1H), 6.32 (bs, 1H), 6.66 (d, J=8.1 Hz, 1H), 6.72 (m, 1H), 6.81 (t, J=7.7 Hz, 1H), 7.19 (dd, J=5.1 Hz, J=0.8 Hz, 1H), 7.36 (s, 1H), 7.87 (d, J=5.1 Hz, 1H), 8.89 (bs, 1H), 11.58 (bs, 1H);

MS (APCI−) m/z 417 (M−H)−.

EXAMPLE 76

N-[5-({[5-(1H-imidazol-5-yl)-5,6,7,8-tetrahydro-1-naphthalenyl]amino}sulfonyl)-4-methyl-1,3-thiazol-2-yl]acetamide The desired product was prepared according to the method of Example 63 above substituting 2-acetamido-4-methyl-5-thiazolesulfonyl chloride for 1-propanesulfonyl chloride (6.3 mg, 15.3% yield).

$^1$H NMR (500 MHz, DMSO-$d_6$) δ 1.54 (m, 1H), 1.58 (m, 1H), 1.81 (m, 1H), 1.90 (s, 3H), 1.93 (m, 1H), 2.13 (s, 3H), 2.15 (s, 3H), 2.56 (m, 2H), 4.00 (m, 1H), 6.38 (bs, 1H), 6.82 (bs, 1H), 6.87 (d, J=6.0 Hz, 1H), 6.96 (t, J=6.0 Hz, 1H), 7.49 (d, J=1.0 Hz, 1H), 10.3 (bs, 1H), 11.7 (bs, 1H);

MS (APCI−) m/z 431 (M−H)−.

EXAMPLE 77

5-Chloro-N-[5-(1H-imidazol-5-yl)-5,6,7,8-tetrahydro-1-naphthalenyl]-3-methyl-2,3-dihydro-1-benzothiophene-2-sulfonamide The desired product was prepared according to the method of Example 63 above substituting 5-chloro-3-methylbenzo[2,3-b]thiopene-2-sulphonyl chloride for 1-propanesulfonyl chloride (5.8 mg, 13.2% yield).

$^1$H NMR (500 MHz, DMSO-$d_6$) δ 1.36 (m, 1H), 1.42 (m, 1H), 1.73 (m, 1H), 1.85 (m, 1H), 2.29 (s, 3H), 2.41 (m, 1H), 2.55 (m, 1H), 3.97 (m, 1H), 6.41 (bs, 1H), 6.87 (m, 2H), 6.96 (m, 1H), 7.49 (d, J=0.8 Hz, 1H), 7.55 (dd, J=0.8, 6.8 Hz, 1H), 7.96 (s, 1H), 8.06 (d, J=6.8 Hz, 1H), 9.9 (bs 1H), 11.7 (bs, 1H);

MS (APCI−) m/z 379 (M−H)−.

EXAMPLE 78

2,2,2-trifluoro-N-[3-(1H-imidazol-4-ylmethyl)phenyl]ethanesulfonamide, maleate

Example 21C was processed as in Example 21D but substituting 2,2,2-trifluoroethanesulfonyl chloride for methanesulfonyl chloride to provide the title compound which was converted to the maleic acid salt.

mp 161–162° C.;

$^1$H NMR (DMSO-$d_6$) δ 4.00 (s, 2H), 4.51 (q, 2H), 6.05 (s, 2H), 7.03 (d, 1H), 7.07–7.13 (m, 2H), 7.28–7.34 (m, 1H), 7.36 (d, 1H), 8.81 (d, 1H), 10.46 (bs, 1H), 14.10 (bs, 1H);

MS (DCI/NH$_3$) m/z 320 (M+H)+;

Anal. Calcd for $C_{12}H_{12}N_3O_2SF_3 \cdot C_4H_4O_4$: C, 44.14; H, 3.70; N, 9.65. Found: C, 44.18; H, 3.72; N, 9.59.

EXAMPLE 79

N-[4-(1H-imidazol-4-yl)-3,4-dihydro-2H-chromen-8-yl]ethanesulfonamide

Example 19C was processed as in Example 12D to provide the title compound.

$^1$H NMR (DMSO-$d_6$) δ 1.25 (t, 3H), 2.05–2.30 (m, 2H), 3.01 (q, 2H), 4.06 (t, 1H), 4.22 (m, 2H), 6.69 (s, 1H), 6.74 (t, 1H), 6.89 (d, 1H), 7.08 (d, 1H), 7.56 (s, 1H), 8.75 (s, 1H);

MS (APCI+) m/z 308 (M+H)+;

Anal. Calcd for $C_{14}H_{17}N_3O_3S$: C, 54.71; H, 5.57; N, 13.67. Found: C, 54.43; H, 5.63; N, 13.54.

EXAMPLE 80

N-[6-fluoro-4-(1H-imidazol-4-yl)-3,4-dihydro-2H-chromen-8-yl]ethanesulfonamide maleate

EXAMPLE 80A 6-fluoro-8-nitro-2,3-dihydro-4H-chromen-4-one

Concentrated sulfuric acid (5 mL) was cooled to −15° C., treated with 6-fluoro-2,3-dihydro-4H-chromen-4-one (1.0 g, 6.0 mmol), treated with a mixture of 70% nitric acid (1.8 mL) and concentrated sulfuric acid (2.8 mL), stirred at 0° C. for 2 hours and poured into water. The resulting solid was collected by filtration, washed with water and dried under vacuum. Purification of the residue on silica gel eluting with 1:1 ethyl acetate:hexanes provided the title compound.

MS (APCI−) 210 (M−H)−.

EXAMPLE 80B 4-(6-fluoro-4-hydroxy-8-nitro-3,4-dihydro-2H-chromen-4-yl)-N,N-dimethyl-1H-imidazole-1-sulfonamide Example 80A was processed as in Example 1A to provide the title compound.

EXAMPLE 80C 4-(6-fluoro-8-nitro-2H-chromen-4-yl)-N,N-dimethyl-1H-imidazole-1-sulfonamide Example 80B was processed as in Example 31B to provide the title compound.

MS (APCI+) m/z 369 (M+H)+;

EXAMPLE 80D 4-(8-amino-6-fluoro-3,4-dihydro-2H-chromen-4-yl)-N,N-dimethyl-1H-imidazole-1-sulfonamide Example 80C was processed as in Example 1C but substituting ethyl acetate for methanol as the solvent to provide the title compound.

EXAMPLE 80E

N-[6-fluoro-4-(1H-imidazol-4-yl)-3,4-dihydro-2H-chromen-8-yl]ethanesulfonamide, maleate Example 80D was processed as in Example 31D but substituting ethanesulfonyl chloride for methanesulfonyl chloride to provide the title compound which was converted to the maleic acid salt.

$^1$H NMR (DMSO-d6) δ 1.25 (t, 3H), 2.19 (m, 2H), 3.12 (q, 2H), 4.22 (m, 2H), 4.35 (t, 1H), 6.06 (s, 2H), 6.62 (dd, 1H), 7.01 (dd, 1H), 7.27 (s, 1H), 8.69 (s, 1H), 9.12 (s, 1H);

MS (APCI+) m/z 308 (M+H)+;

Anal. Calcd for $C_{14}H_{16}N_3O_3SF \cdot C_4H_4O_4$: C, 48.98; H, 4.57; N, 9.52. Found: C, 49.25; H, 4.73; N, 9.33.

EXAMPLE 81

N-{3-[(E)-1-(1H-imidazol-4-yl)-2-methoxyethenyl]phenyl}ethanesulfonamide

EXAMPLE 81A

4-[(E)-1-(3-aminophenyl)-2-methoxyethenyl]-N,N-dimethyl-1H-imidazole-1-sulfonamide The more polar product from Example 46A was processed as described in Example 46B except that the product was purified on silica gel eluting with 9:1 hexanes:ethyl acetate to provide the title compound.

MS (APCI+) m/z 323 (M+H)+;

EXAMPLE 81B 4-((E)-1-{3-[(ethylsulfonyl)amino]-phenyl}-2-methoxyethenyl)-N,N-dimethyl-1H-imidazole-1-sulfonamide The product from Example 81A was processed as described in Example 46C except that the residue was kept at room temperature for 77 days during which time a portion of the title compound decomposed to the unprotected imidazole. Purification on silica gel eluting with ethyl acetate provided the title compound as the less polar product as well as a more polar product which contained the unprotected imidazole.

MS (APCI+) m/z 415 (M+H)+;

EXAMPLE 81C

N-{3-[(E)-1-(1H-imidazol-4-yl)-2-methoxyethenyl]phenyl}ethanesulfonamide

The more polar product from Example 81B was purified again on silica gel eluting with 10% ethanol/ammonia-saturated dichloromethane to provide the title compound.

$^1$H NMR (DMSO-d6) δ 1.19 (t, 3H), 3.05 (q, 2H), 3.67 (s, 3H), 6.65 (d, 1H), 6.85 (bs, 1H), 7.07 (m, 2H), 7.22–7.30 (m, 2H), 7.58 (s, 1H), 9.68 (s, 1H), 11.91 (bs, 1H);

MS (APCI+) m/z 308 (M+H)+;

Anal. calcd for $C_{14}H_{17}N_3O_3S \cdot 0.5\ H_2O$: C, 53.15; H, 5.73; N, 13.28. Found: C, 53.25; H, 5.49; N, 13.28.

In vitro Binding Assays

For purposes of discussing $\alpha_1$ adrenoceptor subtypes, the IUPHAR convention of using lower case letters to define molecular clones and upper case letters to indicate pharmacologically defined adrenoceptors has been followed. Compounds of formula I were evaluated in radioligand binding assays specific for $\alpha_{1A}$ (rat submaxillary gland), $\alpha_{1b}$ (hamster receptor expressed in mouse fibroblasts) and $\alpha_{1d}$ (rat receptor expressed in mouse fibroblasts) using [$^3$H]-prazosin as the radioligand as described in Knepper, et al. J. Pharm. Exp. Ther. (1995), 274, 97–103. The results are shown in Table 1.

TABLE 1

| | Radioligand Binding Ki (nM) | | |
|---|---|---|---|
| Example | $\alpha_{1A}$ (Rat) | $\alpha_{1b}$ (Hamster) | $\alpha_{1d}$ (Rat) |
| 1 | 500 | 1700 | 482 |
| 2 | 36.1 | 2520 | 1260 |
| 3 | 991 | 50400 | 8290 |
| 4 | 24600 | 31600 | 31600 |
| 5 | 136 | 6140 | 1550 |
| 6 | 2080 | 100000 | 16700 |
| 7 | 661 | 100000 | 3780 |
| 8 | 176 | 4620 | 1590 |
| 9 | 91.0 | 2000 | 1910 |
| 10 | 1150 | 10400 | 1690 |
| 11 | 82.2 | 1400 | 311 |
| 12 | 95.9 | 6980 | 1670 |
| 14 | 277 | 2020 | 1040 |
| 15 | 204 | 10000 | 701 |
| 16 | 520 | 10000 | 10000 |
| 17 | 167 | 10000 | 3300 |
| 18 | 1140 | 10000 | 2050 |
| 19 | 475 | 10000 | 1150 |
| 20 | 253 | 10000 | 10000 |
| 21 | 361 | 1270 | 212 |
| 22 | 91.9 | 2030 | 761 |
| 23 | 391 | 10000 | 2670 |
| 24 | 712 | 10000 | 10000 |
| 25 | 2460 | 10000 | 10000 |
| 26 | 1680 | 10000 | 10000 |
| 27 | 531 | 10000 | 2670 |
| 28 | 525 | 10000 | 815 |
| 29 | 258 | 3880 | 678 |
| 30 | 135 | 882 | 279 |
| 31 | 837 | 10000 | 685 |
| 33 | 46.8 | 1300 | 1080 |
| 34 | 1300 | 10000 | 842 |
| 35 | 2180 | 10000 | 10000 |
| 36 | 124 | 10000 | 10000 |
| 37 | 772 | 2280 | 452 |
| 38 | 1360 | 10000 | 2540 |
| 39 | 22.6 | 2010 | 969 |
| 40 | 1340 | 10000 | 10000 |
| 41 | 752 | 1630 | 348 |
| 42 | 359 | 10000 | 2280 |
| 43 | 445 | 10000 | 2860 |
| 44 | 310 | 10000 | 3050 |
| 45 | 565 | 1730 | 971 |
| 46 | 553 | 1140 | 358 |
| 47 | 830 | 10000 | 2140 |
| 55 | 3650 | 10000 | 2340 |
| 56 | 229 | 15.1 | 1.98 |
| 61 | 1560 | 10000 | 10000 |
| 62 | 1910 | 10000 | 10000 |
| 63 | 1720 | 10000 | 10000 |
| 64 | 4150 | 10000 | 10000 |
| 65 | 1160 | 4400 | 5300 |

TABLE 1-continued

Radioligand Binding Ki (nM)

| Example | $\alpha_{1A}$ (Rat) | $\alpha_{1b}$ (Hamster) | $\alpha_{1d}$ (Rat) |
|---|---|---|---|
| 66 | 366 | 1130 | 458 |
| 67 | 901 | 2390 | 3740 |
| 68 | 5280 | | |
| 69 | 4470 | 10000 | 10000 |
| 70 | 430 | 387 | 353 |
| 71 | 1540 | 1050 | 2290 |
| 72 | 1510 | 10000 | 2280 |
| 73 | 1020 | 1190 | 2230 |
| 74 | 5060 | | |
| 75 | 4600 | | |
| 76 | 3210 | | |
| 77 | 650 | 320 | 111 |

In vitro Functional Assays

Compounds of formula I also were evaluated for their ability to stimulate contraction of smooth muscle tissues containing $\alpha_{1A}$ (rat epididymal vas deferens), $\alpha_{1B}$ (rat spleen) and $\alpha_{1D}$ (rat aorta) receptors as described in (Knepper, et al. J. Pharm. Exp. Ther. (1995), 274, 97–103), except that the endothelium was removed from the rat aorta strips. Most of the compounds were tested for $\alpha_{1A}$ functional activity using rabbit urethra as follows. Female New Zealand white rabbits (2.0–3.5 Kg) were sedated with $CO_2$ and decapitated. The entire urethra was removed and immediately placed into Krebs Ringer bicarbonate solution with the following mM concentrations: 120 NaCl, 20 $NaHCO_3$, 11 dextrose, 4.7 KCl, 2.5 $CaCl_2$, 1.5 $MgSO_4$, 1.2 $KH_2PO_4$, 0.01 $K_2EDTA$, equilibrated 5% $CO_2$: 95% $O_2$ (pH=7.4 at 37° C.). Subsequent experimental conditions were as described above for the other tissues. Agonist concentration response curves were cumulative except for the vas deferens assay in which the transient response made such measurements impractical.

The in vitro functional data are shown in Table 2.

TABLE 2

Agonist Tissue Response (pD2)

| Example | $\alpha_{1A}$ (rab ureth) | $\alpha_{1B}$ (rat spleen) | $\alpha_{1D}$ (rat aorta) |
|---|---|---|---|
| 1 | <3.00* | 3.02 | 5.26 |
| 2 | 7.77* | 6.64 | 5.72 |
| 3 | 5.71* | 4.89 | 4.55 |
| 4 | 3.51* | <3.00 | 4.02 |
| 5 | 6.29 | 5.03 | 5.48 |
| 7 | <3.00* | <3.00 | |
| 8 | 6.35 | 5.29 | 4.37 |
| 9 | 6.45 | <3.00 | <3.00 |
| 10 | 4.67 | 4.19 | 4.19 |
| 11 | 6.83 | 5.92 | 6.16 |
| 12 | 6.20 | <3.00 | <3.00 |
| 14 | 5.25 | <3.00 | <3.00 |
| 15 | 6.16 | 5.65 | <3.00 |
| 16 | 5.89 | 4.84 | <3.00 |
| 17 | 6.28 | 5.47 | <3.00 |
| 18 | 5.17 | 4.85 | 4.96 |
| 19 | 6.00 | 5.09 | 5.08 |
| 20 | 5.55 | <3.00 | <3.00 |
| 21 | 5.73 | <3.00 | <3.00 |
| 22 | 6.78 | 5.52 | 5.07 |
| 23 | 4.40 | <3.00 | <3.00 |
| 24 | 4.61 | <3.00 | <3.00 |
| 25 | 4.48 | 3.12 | <3.00 |
| 26 | 4.81 | 4.74 | <3.00 |
| 27 | 5.25 | | |
| 28 | 5.25 | 5.11 | <3.00 |
| 29 | 5.60 | <3.00 | <3.00 |

TABLE 2-continued

Agonist Tissue Response (pD2)

| Example | $\alpha_{1A}$ (rab ureth) | $\alpha_{1B}$ (rat spleen) | $\alpha_{1D}$ (rat aorta) |
|---|---|---|---|
| 30 | 6.22 | 6.16 | <3.00 |
| 31 | 5.38 | <3.00 | <3.00 |
| 33 | 6.77 | 5.42 | <3.00 |
| 34 | 4.55 | <3.00 | <3.00 |
| 35 | 4.09 | <3.00 | <3.00 |
| 36 | 5.73 | <3.00 | <3.00 |
| 37 | 5.27 | | |
| 38 | 4.72 | | |
| 39 | 7.18 | <3.00 | <3.00 |
| 41 | 4.87 | | |
| 42 | <3.00 | | |
| 43 | 4.35 | <3.00 | <3.00 |
| 44 | 5.31 | <3.00 | <3.00 |
| 45 | 5.70 | <3.00 | <3.00 |
| 46 | 4.90 | | |
| 47 | 4.54 | <3.00 | <3.00 |
| 56 | 4.79 | | <3.00 |
| 67 | 3.97 | | |
| 70 | 4.09 | | |
| 73 | 4.75 | | |
| 77 | 4.54 | | |
| 78 | 5.05 | | |

*test performed using rat epididymal vas deferens

In vivo Functional Assays-Assessment of Intrurethral Pressure (IUP) and Mean Arterial Pressure (MAP) in Anesthetized Dogs Female dogs (Marshall Farms, North Rose, N.Y.) greater that 2 years of age and weighing between 12 and 15 kg were used in these studies. At least 2 weeks prior to any agonist dosing, dogs were instrumented for the chronic measurement of arterial blood pressure by implanting a telemetry transducer/transmitter (TA11PA-C40, Data Sciences International, St. Paul, Minn.) into a carotid artery.

On the test day, dogs fasted since the previous afternoon were pre-anesthetized with thiopental sodium 15 mg/kg i.v. (Pentothal™, Abbott) and intubated. Anesthesia was maintained by allowing the dog to spontaneously breathe a mixture of isoflurane (2.5 to 3 volume %) and oxygen delivered by a Narkomed Standard anesthesia system (North American Drager, Telford, Pa.). An Abbocath-T™ i.v. catheter (18-G, Abbott) was inserted into the cephalic vein for the administration of agonists. A telemetry receiver (RA1310, DataSciences) was placed under the head of each dog and was interfaced to a computerized data acquisition system (Modular Instruments Inc.(MI2), Malvern, Pa.) which allowed for the continuous calibrated recording of arterial blood pressure which was electronically filtered to determine its mean value (MAP).

Dogs with chronic telemetry implants anesthetized as described above were placed in dorsal recumbency and a balloon catheter was inserted into the urethral orifice and advanced approximately 15 cm until the tip was well inside the bladder. The balloon was then inflated with 1 ml of room air and the catheter slowly withdrawn until resistance (corresponding to the bladder neck) was evident. The balloon was then deflated and the catheter withdrawn an additional 2 cm. The balloon was then reinflated and its catheter port connected to a Gould Statham P23Dd pressure transducer interfaced to a computerized data acquisition system (Modular Instruments, Inc., Malvern, Pa.) for the measurement of intraurethral pressure. Increasing iv doses of test agonists were administered and the maximum effect of each dose on IUP was recorded. The effect of each dose was allowed to return to baseline before the next dose was given.

From the resulting dose response curve, an $ED_5$ value, for the dose causing a maximum increase in IUP of 5 mm Hg, could be estimated. An $ED_{20}$ value for the dose causing a maximum increase in MAP of 20 mm Hg could also be estimated. A selectivity ratio of MAP $ED_{20}$ vs. IUP $ED_5$ was calculated. The mean of the selectivity ratio of MAP $ED_{20}$ vs. ILuP $ED_5$ is displayed in Table 3.

TABLE 3

IUP $ED_5$ Values for Test Compounds

| Example | Mean IUP $ED_5$ (nmol/kg) | Mean MAP $ED_{20}$ (nmol/kg) | Mean Selectivity Ratio MAP $ED_{20}$/IUP $ED_5$ |
|---|---|---|---|
| 8 | 25.5 | 102 | 4.8 |
| 9 | 20.4 | 48.7 | 4.4 |
| 10 | >300 | >300 | — |
| 12 | 10.7 | 69.3 | 7.6 |
| 14 | >1000 | >1000 | — |
| 15 | 91.9 | 225 | 2.5 |
| 16 | 68.4 | 220 | 3.1 |
| 17 | 187.7 | 216 | 1.1 |
| 19 | 67.1 | 164 | 2.3 |
| 20 | 208.9 | 885 | 6.1 |
| 21 | 22.7 | 52.3 | 2.7 |
| 26 | 653 | 1850 | 2.6 |
| 28 | 77.1 | 158 | 2.1 |
| 29 | 41.1 | 202 | 5.6 |
| 30 | 12.1 | 80.5 | 6.5 |
| 31 | 91.6 | 234 | 3.4 |
| 33 | 10.5 | 34.0 | 3.3 |
| 34 | >1000 | >1000 | — |
| 36 | 156 | 508 | 3.6 |
| 39 | 4.4 | 5.6 | 1.3 |
| 44 | 844 | 632 | 1.0 |
| 45 | 273 | 633 | 2.6 |

Assessment of Urethral Pressure Profile in Anesthetized Dogs

Dogs instrumented and anesthetized as decribed above were placed in left lateral recumbency and a dual pressure sensor catheter (SPC-771, Millar Instruments, Houston, Tex.) was inserted into the urethra and advanced into the bladder. The proximal pressure sensor was interfaced to a MI2 computerized data acquisition system for the measurement of lower urinary tract pressures. At a resting intravesical pressure of approximately 5 cm of $H_2O$, urethral pressure was measured from the sensor as the catheter was withdrawn using a modified syringe pump (Model 22, Harvard Apparatus, South Natick, Mass.) at its maximal rate of 0.83 mm/sec. Measurement from the proximal sensor allowed easy reinsertion as the distal 5 cm of the catheter remains in the urethra after the total profile has been obtained. Three resting urethral pressure profiles were obtained at 5 minute intervals before dosing, then a single profile was initiated 30 sec after each increasing iv dose during the time corresponding to the maximum arterial pressure effects of that dose. The increase in arterial pressure seen after each agonist dose was allowed to return to baseline before the next dose was given.

DESCRIPTION OF DRAWING

FIG. 1 displays the urethral pressure profile for Example 8 from this invention. The Y axis displays the urethral pressure. The X axis displays the distance along the length of the urethra from the proximal to the distal end. FIG. 1 illustrates that increasing concentrations of Example 8 result in corresponding increases in the urethral pressure.

The results from Tables 1 and 2 show that the compounds of the invention bind to, simulate, and show specificity for the $\alpha_{1A}$ adrenoceptor and therefore have utility in the treatment of diseases prevented by or ameliorated with compounds which activate the $\alpha_{1A}$ adrenoceptor. Table 3 illustrates that the compounds of this invention are efficacious in constricting the urethra. Table 3 also illustrates that these compounds are selective for constricting the urethra over increasing the mean arterial pressure. FIG. 1 illustrates that the compounds of this invention are efficacious in constricting the urethra in a manner which is considered to be clinically relevant for the treatment of urinary incontinence.

The data in Table 3 demonstrates that compounds of the invention contract the smooth muscle of the urethra and hence are useful for treating conditions such as retrograde ejaculation that result from deficient smooth muscle tone of the urethra and bladder neck.

Ethanesulfonamide compounds of formula I, wherein $R_3$ and $R_4$ do not form a ring, exhibit suprisingly better in vivo selectivity for increasing intraurethral pressure over arterial pressure than methanesulfonamides. For example, N-(3-(1H-imidazol-4-ylmethyl)phenyl]ethanesulfonamide and N-(3-(1H-imidazol-4-ylmethyl)-2-methylphenyl]ethanesulfonamide show greater than 2.5 and 3 times the selectivity for increasing intraurethral pressure over arterial pressure respectiviely as compared to N-(3-(1H-imidazol-4-ylmethyl)-2-methylphenyl]methanesulfonamide compound.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The present invention provides pharmaceutical compositions which comprise compounds of the present invention formulated together with one or more non-toxic pharmaceutically acceptable carriers. Further included within the scope of the present invention are pharmaceutical compositions comprising one or more of the compounds of formula I–X prepared and formulated in combination with one or more non-toxic pharmaceutically acceptable compositions. The pharmaceutical compositions can be formulated for oral administration in solid or liquid form, for parenteral injection or for rectal administration.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration which include intravenous, intramuscular, intraperitoneal, intrasternal, subcutaneous, intraarticular injection and infusion.

Pharmaceutical compositions of this invention for parenteral injection comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity may be maintained, for example, by the use of a coating such as lecithin, by the maintenance of the required particle size in the case of dispersions, and by the use of surfactants.

These compositions may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

In some cases, in order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Suspensions, in addition to the active compounds, may contain suspending agents, as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the present invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

The active compounds can also be in micro-encapsulated form, if appropriate, with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound can be admixed with at least one inert diluent such as sucrose, lactose, or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of such composition that they release the active ingredient(s) only, or preferentially, in a certain part of the intestinal tract in a delayed manner. Examples of embedding compositions which can be used include polymeric substances and waxes.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of embedding compositions which can be used include polymeric substances and waxes.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention may include ointments, pastes, creams, lotions, gels, powders, solutions, sprays, inhalants or patches. The active component is admixed under sterile conditions with a pharmaceutically acceptable carrier and any needed preservatives or buffers as may be required. It is known that some agents may require special handling in the preparation of transdermal patch formulations. For example, compounds that are volatile in nature may require admixture with special formulating agents or with special packaging materials to assure proper dosage delivery. In addition, compounds which are very rapidly absorbed through the skin may require formulation with absorption-retarding agents or barriers. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention,. excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Compounds of the present invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the present invention, stabilizers, preservatives, excipients, and the like. The preferred lipids are the natural and synthetic phospholipids and phosphatidylcholines (lecithins) used separately or together.

Methods to form liposomes are known in the art. See, for example, Prescott, Ed., *Methods in Cell Biology,* Volume XIV, Academic Press, New York, N.Y., (1976), p 33 et seq.

The term "pharmaceutically acceptable cation," as used herein, refers to a positively-charged inorganic or organic ion that is generally considered suitable for human consumption. Examples of pharmaceutically acceptable cations are hydrogen, alkali metal (lithium, sodium and potassium), magnesium, calcium, ferrous, ferric, ammonium, alkylammonium, dialkylammonium, trialkylanmmonium, tetraalkylammonium, diethanolammmonium, and choline. Cations may be interchanged by methods known in the art, such as ion exchange. Where compounds of the present invention are prepared in the carboxylic acid form, addition of a base (such as a hydroxide or a free amine) will yield the appropriate cationic form.

The term "pharmaceutically acceptable salt, ester, amide, and prodrug," as used herein, refers to carboxylate salts, amino acid addition salts, zwitterions, esters, amides, and prodrugs of compounds of formula I–X which are within the scope of sound medical judgement, suitable for use in contact with the tissues of humans and lower animals without undue toxicity, irritation, allergic response, and the like, are commensurate with a reasonable benefit/risk ratio, and are effective for their intended use.

The compounds of the present invention can be used in the form of pharmaceutically acceptable salts derived from inorganic or organic acids. By "pharmaceutically acceptable salt" is meant those salts which are, within the scope of sound medical judgement, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail *in J. Pharmaceutical Sciences,* 1977, 66: 1 et seq. The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsufonate, digluconate, glycerophosphate, hemisulfate, heptanoate, hexanoate, s fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like. Preferred salts of the compounds of the invention include phosphate, tris and acetate.

The term "pharmaceutically acceptable ester" or "ester," as used herein, refers to esters of compounds of the present invention which hydrolyze in vivo and include those that break down readily in the human body to leave the parent compound or a salt thereof. Examples of pharmaceutically acceptable, non-toxic esters of the present invention include $C_1$-to-$C_6$ alkyl esters and $C_5$-to-$C_7$ cycloalkyl esters, although $C_1$-to-$C_4$ alkyl esters are preferred. Esters of the compounds of formula I–X may be prepared according to conventional methods.

The term "pharmaceutically acceptable amide" or "amide," as used herein, refers to non-toxic amides of the present invention derived from ammonia, primary $C_1$-to-$C_6$ alkyl amines and secondary $C_1$-to-$C_6$ dialkyl amines. In the case of secondary amines, the amine may also be in the form of a 5- or 6-membered heterocycle containing one nitrogen atom. Amides derived from ammonia, $C_1$-to-$C_3$ alkyl primary amides and $C_1$-to-$C_2$ dialkyl secondary amides are preferred. Amides of the compounds of formula I–X may be prepared according to conventional methods.

The term "pharmaceutically acceptable prodrug" or "prodrug," as used herein, represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use. Prodrugs of the present invention may be rapidly transformed in vivo to the parent compound of the above formula, for example, by hydrolysis in blood. A thorough discussion is provided in T. Higuchi and V. Stella, *Pro-drugs as Novel Delivery Systems*, V. 14 of the A.C.S. Symposium Series, and in Edward B. Roche, ed., *Bioreversible Carriers in Drug Design*, American Pharmaceutical Association and Pergamon Press (1987), hereby incorporated by reference.

The term "prodrug ester group," as used herein refers, to any of several ester-forming groups that are hydrolyzed under physiological conditions. Examples of prodrug ester groups include pivoyloxymethyl, acetoxymethyl, phthalidyl, indanyl and methoxymethyl, as well as other such groups known in the art. Other examples of prodrug ester groups can be found in the book "Pro-drugs as Novel Delivery Systems," by Higuchi and Stella, cited above.

The present invention contemplates pharmaceutically active metabolites formed by in vivo biotransformation of compounds of formula I–X. The term pharmaceutically active metabolite, as used herein, refers to a compound formed by the in vivo biotransformation of compounds of formula I–X. The present invention contemplates compounds of formula I–X and metabolites thereof. A thorough discussion of biotransformation is provided in Goodman and Gilman's, *The Pharmacological Basis of Therapeutics,* seventh edition, hereby incorporated by reference.

The compounds of the invention, including but not limited to those specified in the examples, are $\alpha_{1A}$ adrenergic agonists. As $\alpha_{1A}$ agonists, the compounds of the present invention are useful for the treatment and prevention of diseases such as urinary incontinence and ejaculatory dysfunction such as retrograde ejaculation.

The ability of the compounds of the invention to treat urinary incontinence can be demonstrated according to the methods described (Testa, R. Eur. J. Pharmacol. (1993), 249, 307–315) and (Cummings, J. M. Drugs of Today (1996), 32, 609–614).

Aqueous liquid compositions of the present invention are particularly useful for the treatment and prevention of urinary incontinence and ejaculatory dysfunction.

When used in the above or other treatments, a therapeutically effective amount of one of the compounds of the present invention can be employed in pure form or, where such forms exist, in pharmaceutically acceptable salt, ester, amide or prodrug form. Alternatively, the compound can be administered as a pharmaceutical composition containing the compound of interest in combination with one or more pharmaceutically acceptable excipients. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal may range from about 0.003 to about 10 mg/kg/day. For purposes of oral administration, more preferable doses can be in the range of from about 0.01 to about 5 mg/kg/day. If desired, the effective daily dose can be divided into multiple doses for purposes of administration; consequently, single dose compositions may contain such amounts or submultiples thereof to make up the daily dose.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

What is claimed is:

1. A compound selected from the group consisting of: N-(3-(1H-imidazol-4-ylmethyl)2-methylphenyl) ethanesulfonamide and N-(3-(1H-imidazol-4-ylmethyl) phenyl)ethanesulfonamide and pharmaceutically acceptable salts thereof.

2. A pharmaceutical composition comprising a therapeutically effective amount of a compound of claim 1 in combination with a pharmaceutically acceptable carrier.

3. A method of activating A1 adrenoceptors in a host mammal in need of such treatment comprising administering a therapeutically effective amount of a compound of claim 1.

4. A method of treating a disease in a host mammal in need of such treatment comprising administering a therapeutically effective amount of a compound of claim 1.

5. The method of claim 4 wherein the disease is urinary incontinence.

6. The method of claim 4 wherein the disease is retrograde ejaculation.

* * * * *